US012806142B2

(12) United States Patent
Wang et al.

(10) Patent No.: US 12,806,142 B2

(45) Date of Patent: Nov. 24, 2026

(54) LIPOCOACERVATES AND METHODS OF MAKING AND USING SAME

(71) Applicant: Cornell University, Ithaca, NY (US)

(72) Inventors: Yadong Wang, Ithaca, NY (US); Chia-Wei Yeh, Ithaca, NY (US)

(73) Assignee: Cornell University, Ithaca, NY (US)

( * ) Notice: Subject to any disclaimer, the term of this patent is extended or adjusted under 35 U.S.C. 154(b) by 53 days.

(21) Appl. No.: 18/674,264

(22) Filed: May 24, 2024

(65) Prior Publication Data

US 2024/0390281 A1 Nov. 28, 2024

Related U.S. Application Data

(60) Provisional application No. 63/468,678, filed on May 24, 2023.

(51) Int. Cl.

*A61K 9/127* (2025.01)
*A61K 9/1271* (2025.01)
*A61K 38/18* (2006.01)
*A61K 38/20* (2006.01)

(52) U.S. Cl.

CPC ............ *A61K 9/1271* (2013.01); *A61K 38/18* (2013.01); *A61K 38/20* (2013.01)

(58) Field of Classification Search

None

See application file for complete search history.

(56) References Cited

U.S. PATENT DOCUMENTS

2008/0089927 A1* 4/2008 Malinin ................ A61K 9/127 514/36

OTHER PUBLICATIONS

Aumiller, et al., "RNA-Based Coacervates as a Model for Membraneless Organelles: Formation, Properties, and Interfacial Liposome Assembly," Langmuir, vol. 32, pp. 10042-10053 (2016).

Awada, et al., "Dual Delivery of Vascular Endothelial Growth Factor and Hepatocyte Growth Factor Coacervate Displays Strong Angiogenic Effects," Macromol. Biosci., vol. 14, pp. 679-686 (2014).

Awada, et al., "Sequential delivery of angiogenic growth factors improves revascularization and heart function after myocardial infarction," Journal of Controlled Release, vol. 207, pp. 7-17 (Jun. 10, 2015).

Awada, et al., "A Single Injection of Protein-loaded Coacervate-Gel Significantly Improves Cardiac Function Post Infarction," Biomaterials, vol. 125, pp. 65-80 (May 2017).

Booth, et al., "Spatial Positioning and Chemical Coupling in Coacervate-in-Proteinosome Protocells," Angew. Chem. Int. Ed., vol. 58, pp. 9120-9124 (2019).

Cakmak, et al., "Lipid Vesicle-Coated Complex Coacervates," Langmuir, vol. 35, No. 24, pp. 7830-7840 (Jun. 18, 2019).

Cakmak, et al., "Phospholipid Membrane Formation Templated by Coacervate Droplets," Langmuir, vol. 37, pp. 10366-10375 (2021).

Cao, et al., "Collaborative interplay between FGF-2 and VEGF-C promotes lymphangiogenesis and metastasis," PNAS, vol. 109, No. 39, pp. 15894-15899 (Sep. 25, 2012).

Chakraborty, et al., "How cholesterol stiffens unsaturated lipid membranes," PNAS, vol. 117, No. 36, pp. 21896-21905 (Sep. 8, 2020).

Chen, et al., "Controlled Dual Delivery of Fibroblast Growth Factor-2 and Interleukin-10 by Heparin-based Coacervate Synergistically Enhances Ischemic Heart Repair," Biomaterials, vol. 72, pp. 138-151 (Dec. 2015).

Cho, et al., "Dual delivery of stem cells and insulin-like growth factor-1 in coacervate-embedded composite hydrogels for enhanced cartilage regeneration in osteochondral defects," Journal of Controlled Release, vol. 327, pp. 284-295 (2020).

Chu, et al., "A [polycation: heparin] complex releases growth factors with enhanced bioactivity," Journal of Controlled Release, vol. 150, pp. 157-163 (2011).

Chu, et al., "Injectable fibroblast growth factor-2 coacervate for persistent angiogenesis," PNAS, vol. 108, No. 33, pp. 13444-13449 (Aug. 16, 2011).

Chu, et al., "The effect of a heparin-based coacervate of fibroblast growth factor-2 on scarring in the infarcted myocardium," Biomaterials, vol. 34, pp. 1747-1756 (2013).

Deng, et al., "Microfluidic Formation of Monodisperse Coacervate Organelles in Liposomes," Angew. Chem. Int. Ed., vol. 56, pp. 9736-9740 (2017).

Deng, et al., "Macromolecularly Crowded Protocells from Reversibly Shrinking Monodisperse Liposomes," J. Am. Chem. Soc., vol. 140, pp. 7399-7402 (2018).

Deshpande, et al., "Spatiotemporal control of coacervate formation within liposomes," Nature Communications, 10:1800, https://doi.org/10.1038/s41467-019-0955-x (2019).

Ding, et al., "Scale-up synthesis of a polymer designed for protein therapy," European Polymer Journal, vol. 117, pp. 353-362 (2019).

Gao, et al., "Membranized Coacervate Microdroplets: from Versatile Protocell Models to Cytomimetic Materials," Acc. Chem. Res., vol. 56, pp. 297-307 (2023).

(Continued)

*Primary Examiner* — Brian Gulledge

(74) *Attorney, Agent, or Firm* — Young Basile Hanlon & MacFarlane, P.C.

(57) ABSTRACT

Lipocoacervates and compositions comprising lipocoacervates, methods of making and using same. A lipocoacervate comprises a coacervate phase and a lipid or lipids, where the lipid(s) is/are disposed on at least a portion of an exterior surface of the coacervate phase, and optionally, one or more biomolecules. In various examples, a coacervate phase comprises cationic component(s), such as, for example, polycations, such as, for example, chitosan, spermine, spermidine, positively-charged polymers, positively-charged proteins, and any combination thereof, and anionic component(s), such as, for example, polyanions, such as, for example, glycosaminoglycans, nucleic acids, negatively-charged proteins, and any combination thereof. In various examples, an anionic component is a biomolecule. In various examples, a lipocoacervate is made by contacting a coacervate composition with a lipid composition, where lipocoacervate(s) or a lipocoacervate composition is/are formed. In various examples, lipocoacervates or lipocoacervate composition(s) is/are used to intracellularly deliver a biomolecule or biomolecules to an individual.

35 Claims, 28 Drawing Sheets
(16 of 28 Drawing Sheet(s) Filed in Color)

(56) References Cited

OTHER PUBLICATIONS

Hwang, et al., "Single injection of IL-12 coacervate as an effective therapy against B16-F10 melanoma in mice," Journal of Controlled Release, vol. 318, pp. 270-278 (2020).
Jeon, et al., "In situ forming growth factor-loaded coacervate microparticle-embedded hydrogel for directing encapsulated stem cell fate," Adv Mater., vol. 27, No. 13, pp. 2216-2223 (Apr. 2015).
Jo, et al., "Development of Polymer Coacersome Structure with Enhanced Colloidal Stability for Therapeutic Protein Delivery," Macromol. Biosci., vol. 19, 1900207, pp. 1-11 (2019).
Johnson, et al., "Controlled Delivery of Heparin-Binding EGF-Like Growth Factor Yields Fast and Comprehensive Wound Healing," Journal of Controlled Release, vol. 166, No. 2, pp. 124-129 (Mar. 10, 2013).
Johnson, et al., "Coacervate Delivery of Growth Factors Combined with a Degradable Hydrogel Preserves Heart Function after Myocardial Infarction," ACS Biomater. Sci. Eng., vol. 1, pp. 753-759 (2015).
Johnson, et al., "Coacervate delivery of HB-EGF accelerates healing of type 2 diabetic wounds," Wound Repair Regen. vol. 23, No. 4, pp. 591-600 (2015).
Kim, et al., "Enhanced Skull Bone Regeneration by Sustained Release of BMP-2 in Interpenetrating Composite Hydrogels," Biomacromolecules, vol. 19, pp. 4239-4249 (2018).
Last, et al., "pH-Controlled Coacervate—Membrane Interactions within Liposomes," ACS Nano, vol. 14, pp. 4487-4498 (2020).
Lee, et al., "Growth factor delivery-based tissue engineering: general approaches and a review of recent developments," J. R. Soc. Interface, vol. 8, pp. 153-170 (2011).
Li, et al., "Sustained Release of Bone Morphogenetic Protein 2 via Coacervate Improves the Osteogenic Potential of Muscle-Derived Stem Cells," Stem Cells Translational Medicine, vol. 2, pp. 667-677 (2013).
Li, et al., "Combinatorial engineering of bulk-assembled monodisperse coacervate droplets towards logically integrated protocells," bioRxiv preprint, https://doi.org/10.1101/2021.02.19.432011 (Feb. 19, 2021).
Liu, et al., "Enzyme-mediated nitric oxide production in vasoactive erythrocyte membrane-enclosed coacervate protocells," Nature Chemistry, vol. 12, pp. 1165-1173 (Dec. 2020).
Liu, et al., "Signal processing and generation of bioactive nitric oxide in a model prototissue," Nature Communications, No. 13, 5254, pp. 1-11 (2022).
Long, et al., "Controlled Delivery of Platelet-Derived Proteins Enhances Porcine Wound Healing," Journal of Controlled Release, No. 253, pp. 73-81 (May 10, 2017).
Love, et al., "Reversible pH-Responsive Coacervate Formation in Lipid Vesicles Activates Dormant Enzymatic Reactions," Angew. Chem. Int. Ed., vol. 59, pp. 5950-5957 (2020).
Mansurov, et al., "A controlled release system for simultaneous delivery of three human perivascular stem cell-derived factors for tissue repair and regeneration," J. Tissue Eng. Regen. Med., vol. 12, pp. e1164-e1172 (2018).
Matsuo, et al., "Proliferating coacervate droplets as the missing link between chemistry and biology in the origins of life," Nature Communications, vol. 12, 5487, pp. 1-13 (2021).
Rauck, et al., "Biocompatibility of a Coacervate-Based Controlled Release System for Protein Delivery to the Injured Spinal Cord," Acta Biomater., vol. 11, pp. 204-211 (Jan. 1, 2015).
Ren, et al., "Growth Factor Engineering Strategies for Regenerative Medicine Applications," Frontiers in Bioengineering and Biotechnology, vol. 7, 469, pp. 1-9 (Jan. 2020).
Spector, et al., "Membrane lipid composition and cellular function," Journal of Lipid Research, vol. 26, pp. 1015-1035 (1985).
Tang, et al., "Fatty acid membrane assembly on coacervate microdroplets as a step towards a hybrid protocell model," Nature Chemistry, vol. 6, pp. 527-533 (Jun. 2014).
Van Meer, et al., "Membrane lipids: where they are and how they behave," Nat. Rev. Mol. Cell Biol., vol. 9, No. 2, pp. 112-124 (Feb. 2008).
Wang, et al., "Fibroblast Growth Factor-1 Released from a Heparin Coacervate Improves Cardiac Function in a Mouse Myocardial Infarction Model," ACS Biomater. Sci. Eng., vol. 3, pp. 1988-1999 (2017).
Zhang, et al., "Cholesterol provides nonsacrificial protection of membrane lipids from chemical damage at air-water interface," PNAS, vol. 115, No. 13, pp. 3255-3260 (Mar. 27, 2018).
Zhang, et al., "Giant Coacervate Vesicles As an Integrated Approach to Cytomimetic Modeling," J. Am. Chem. Soc., vol. 143, pp. 2866-2874 (2021).

* cited by examiner

LIPOCOACERVATES AND METHODS OF MAKING AND USING SAME

CROSS REFERENCE TO RELATED APPLICATIONS

This application claims the benefit of U.S. Provisional Application No. 63/468,678, filed May 24, 2023; the contents of the above-identified application are hereby fully incorporated herein by reference in their entirety.

STATEMENT REGARDING FEDERALLY SPONSORED RESEARCH

This invention was made with government support under W81XWH-21-1-0527 awarded by the Defense Health Agency, Medical Research and Development Branch. The government has certain rights in the invention.

BACKGROUND OF THE DISCLOSURE

Controlled delivery of proteins and other biologics is a growing medium of therapy for diseases previously untreatable. Growth factors (GFs) are powerful signaling molecules for many biological activities including cell proliferation, differentiation, and migration. However, due to the short half-life in the plasma, multiple and usually high dosage administrations are typically required to achieve effective concentration of GFs at the target site, resulting in adverse side effects. An effective controlled-release vehicle is therefore necessary for GF therapy.

Complex coacervates, electrostatically bound complexes formed between cationic and anionic polyelectrolytes, is a type of liquid-liquid phase separation. It assembles by the same interactions between glycosaminoglycans like heparin sequester growth factors such as fibroblast growth factor-2 (FGF-2) in the extracellular matrix. The resultant complex forms a stable reservoir that modulates growth factor signaling pathways. Due to this mechanism, heparin-based coacervates have emerged as promising candidates for drug delivery systems in biomedical and tissue engineering contexts.

Micro and nano particle delivery of coacervate has become a topic of great interest with the popularization of antibody and biological therapies in recent years. The SARS-COV-2 pandemic only heightened interest in such delivery methods with the success of the mRNA-based vaccines. Within the realm of nanoparticles, the ability to functionalize and incorporate a great range of proteins, including potent growth factors and cytokines, promises many potential therapies. Caldorera-Moore et al. showed the ability to deliver IFN-α using nanoparticles as an oral chemotherapeutic agent capable of passing through tight junctions. Huang et al. used nanoparticles for the treatment of tumors but with an dual immunotherapeutic system. The use of liposome for delivery is important with much work for the delivery of nucleic acids for a variety of diseases. There are successful examples in all approaches of polymeric, inorganic, or liposomal particle delivery. However, issues limiting the translation to clinical use arise for many factors in all these modalities. Impurities and contaminants absorbed to the surfaces during preparation can greatly impact the safety profiles of the nanoparticles because of its high surface area to volume ratio. Liposomes have difficulty loading or generating stable particles without loss of delicate proteins and nucleic acids due to toxic solvents. Coacervates offer a solution through encapsulation of biologics into a droplets without use of toxic solvents and with high loading efficiency. However, coacervates also display issues problematic for delivery such as aggregation over time or stability.

Macromolecularly crowded coacervate is useful in protein delivery for tissue engineering and regenerative medicine. However, coacervate tends to aggregate easily, which impedes their application. Charge interaction between a natural polyanion, heparin, and a synthesized polycation, poly (ethylene argininylaspartate diglyceride) (PEAD) to form a complex coacervate has been shown. Heparin can bind over 300 proteins and peptides in the body. The combination between the protein-heparin complex and PEAD results in a liquid-liquid phase separation with a polymer-rich phase (coacervate) and a polymer-poor phase (supernatant). This PEAD/heparin coacervate system can protect and sustainably release the loaded growth factors, including fibroblast growth factor-2 (FGF-2), vascular endothelial growth factor (VEGF), interleukin (IL)-10 and IL-12. FGF-2 and IL-10 loaded coacervate effectively reduce infarcted region and restore cardiac function in a rat myocardial infarction (MI) model. Furthermore, in a murine melanoma model, IL-12 loaded coacervate significantly reduced tumor growth. The use of PEAD/heparin complex coacervate to load and release growth factors with enhanced bioactivity was first reported by Chu et al. in 2011. They synthesized a biocompatible polycation PEAD and demonstrated two heparin-binding growth factors, FGF-2 and neural growth factor (NGF), was separately loaded into PEAD/heparin coacervate complex with high efficiency. The bioactivity of FGF-2 and NGF were maintained and increased in coacervate group relative to bolus delivery on human aortic endothelial cells and PC-12 cells, respectively. Later, growth factors loaded PEAD/heparin coacervate complexes were extensively studied on various models, including angiogenesis, bone formation, myocardial infarction, wound healing, repair of spinal cord injury, stem cell stimulation, and treatment of skin cancer. Nevertheless, as with all coacervates, due to the highly hydrophobic nature, vesicle-vesicle charge interaction, and inter-molecular hydrogen bonding, coacervates easily aggregate after self-assembly in aqueous solutions. It is worth noting that many of the previous studies utilized hydrogel to deliver growth factors loaded PEAD/heparin coacervate to the target site. Using hydrogel could effectively deliver coacervate to the target site, also temporarily keep the distance between each individual coacervate to prevent the aggregation. To deliver multiple growth factors simultaneously, hydrogel could serve as additional platform to load and release growth factors. As for systemic delivery, it is difficult to deliver coacervate with hydrogel. In general, coacervate is sensitive to environmental factors, including ionic strength and pH. These factors hinder practical use of coacervates.

Lipid-based drug delivery systems (LBDDS) have emerged as a significant area of research and development in the pharmaceutical field. LBDDS contains various entities such as liposomes, micelles, lipid nanoparticles, and extracellular vesicles, among others. These systems consist of lipid-based nano- or micro-structures serving as carriers for therapeutic cargos.

The dogma of liposome literature is that long circulating liposome should be in the nanometer range and should employ PEGylated lipids. Furthermore, all known lipid assemblies stable in an aqueous environment have lipid bilayers. For sufficient mass transfer, the drug carrier must have long contact time with the endothelium. Therefore, microparticles sized similarly to erythrocytes are superior to nanoparticles, which stay midstream of the flow and pass through rapidly.

It has been reported that various factors influence the circulation longevity of colloidal drug carriers, including carrier size, shape, surface properties, and material deformability. Moreover, the adsorption of serum protein opsonins (opsonization) onto the carrier surface through hydrophobic interactions, electrical attraction, and hydrogen bonding may trigger phagocytosis by cells in the mononuclear phagocyte system (MPS). Specifically, predominant phagocytosis by hepatic macrophages (Kupffer cells) leads to a shortened circulation time of these carriers to a few minutes. This phenomenon results in inadequate accumulation or distribution of therapeutic agents within target tissues. Additionally, aggregation is a factor contributing to the short circulation time of colloidal drug carriers. In the presence of high ionic strength in the blood, the surface charge on the carrier may be neutralized by counterions, leading to a loss of repulsion between similarly charged carriers and resulting in aggregation. These aggregated carriers are prone to occlusion of the pulmonary capillary bed, thereby contributing to their elimination from the bloodstream.

SUMMARY OF THE DISCLOSURE

The present disclosure provides, inter alia, lipocoacervates. The present disclosure also provides methods of making and using lipocoacervates.

In an aspect, the present disclosure provides lipocoacervates (LipCos). In various examples, a lipocoacervate is made by a method of the present disclosure. In various examples, a lipocoacervate (LipCo) (e.g., a LipCo droplet, a LipCo vesicle, or the like) comprises a coacervate phase (e.g., a droplet, a vesicle, or the like); and one or more lipid(s). In various examples, the lipid(s) is/are disposed on at least a portion of an exterior surface (or substantially all or all of the exterior surfaces) of the coacervate phase. In various examples, the coacervate phase is a simple coacervate, a complex coacervate, or the like. In various examples, the complex coacervate or the like comprises: one or more cationic component(s); and one or more anionic component(s). In various examples, the lipocoacervate further comprises a biomolecule or two or more different (e.g., compositionally different, structurally different, or functionally different, or any combination thereof) biomolecules. In various examples, the biomolecule(s) is/are independently a therapeutic agent, a bioactive agent, a biofunctional agent, or the like. In various examples, the lipocoacervate is a fluorescent lipocoacervate. In various examples, the coacervate phase and/or the lipocoacervate comprises substantially spherical shape (e.g., spherical) or the like. In various examples, the lipocoacervate comprises or exhibits a size of about 100 nanometers (nm) to about 20 micrometers (microns).

In an aspect, the present disclosure provides compositions. In various examples, a composition comprises a plurality of lipocoacervates of the present disclosure. In various examples, a composition is a pharmaceutical composition. In various examples, a composition is made by a method of the present disclosure.

In various examples, the composition comprises substantially the same or the same lipocoacervates. In various examples, the composition comprises a plurality of (e.g., two or more, three or more, etc.) different (e.g., compositionally different, structurally different, or functionally different, or any combination thereof) lipocoacervates. In various examples, at least a portion of, substantially all, or all the lipocoacervates in a composition comprise independently comprise one or more biomolecule(s). In various examples, at least a portion, substantially all, or all the lipocoacervates in the composition comprise or exhibit an average size of about 100 nm to about 20 microns. In various examples, a composition is a solution or the like. In various examples, the composition is an aqueous dispersion, or the like. In various examples, the composition (or the lipocoacervates of the composition) comprise(s) or exhibit(s) an average zeta potential of about-5 mV to about +5 mV. In various examples, the composition (or the lipocoacervates of the composition) comprise(s) or exhibit(s) an average zeta potential of about-0 mV. In various examples, a composition is stable (e.g., the composition does not exhibit substantial or any lipocoacervate aggregation, a substantial change or any change in lipocoacervate size for at least one-week or more at a temperature of about 4 degrees Celsius (C), or both.

In an aspect, the present disclosure provides methods of making lipocoacervates. In various examples, a method makes a lipocoacervate or a composition of the present disclosure.

In various examples, a method of making lipocoacervates (or a lipocoacervate composition) comprises providing a coacervate composition (e.g., a coacervate solution or the like); and contacting the coacervate composition with a lipid composition, where the lipocoacervates are (or a lipocoacervate composition is) formed. In various other examples, a method of making lipocoacervates (or a lipocoacervate composition) comprises contacting a coacervate composition with a lipid composition, where the lipocoacervates are or the lipocoacervate composition is formed. In various examples, the coacervate composition is formed using an aqueous solution of or comprising one or more single component(s) and/or one or more cationic component(s) and one or more anionic component(s) and, optionally, one or more biomolecule(s).

In an aspect, the present disclosure provides uses of a lipocoacervate or a composition of the present disclosure. In various examples, a lipocoacervate or lipocoacervates of the present disclosure or a composition or compositions of the present disclosure is used in biomolecule delivery methods, which may be intracellular biomolecule delivery methods. In various examples, a method of biomolecule delivery comprises contacting a population of cells, an individual, or the like, with one or more or a plurality of lipocoacervate(s) and/or one or more composition(s), where at least a portion of or all of the lipocoacervate(s) (or biomolecule(s) is/are delivered to the population of cells, the individual, or the like. In various examples, the delivery is intracellular delivery or the like. In various examples, a lipocoacervate or lipocoacervates are used in treatment methods.

In various examples a method comprises treating, preventing, or the like, or any combination thereof, a current or potential disease, disease state, condition, disorder, side effect, or the like, or any combination thereof, in an individual. In various examples, a treatment method comprises delivery (such as, for example, intracellular delivery) of a lipocoacervate or lipocoacervates and/or or one or more biomolecule(s) of a lipocoacervate or lipocoacervates or administration (which may be an effective amount thereof) of a lipocoacervate or lipocoacervates and/or or one or more biomolecule(s) of a lipocoacervate or lipocoacervates and/or one or more composition(s) to an individual. In various examples, an individual is diagnosed with and/or is in need of treatment for a disease, disease state, or the like, and the disease, the disease state, or the like is treatable, preventable, or the like, by one or more or all the biomolecule(s).

In an aspect, the present disclosure provides kits. In various examples, a kit comprises a lipocoacervate or lipocoacervates and/or composition(s) of the present disclosure.

In various examples, the kit comprises a lipocoacervate or lipocoacervates and/or composition(s) of the present disclosure and/or one or more starting material(s) for any of same. In various examples, the kit includes a closed or sealed package that comprises the lipocoacervate or lipocoacervates and/or the composition(s). In various examples, the sealed package comprises one or more closed or sealed vials, bottles, blister (bubble) packs, or any other suitable packaging for the sale, distribution, or use of the lipocoacervate(s) and/or the composition(s) and/or starting material(s). In various examples, the kit includes a label describing the contents of the kit and providing indications and/or instructions regarding use of the contents of the kit to treat an individual.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a fuller understanding of the nature and objects of the disclosure, reference should be made to the following detailed description taken in conjunction with the accompanying figures.

DETAILED DESCRIPTION OF THE DISCLOSURE

Figure 1:
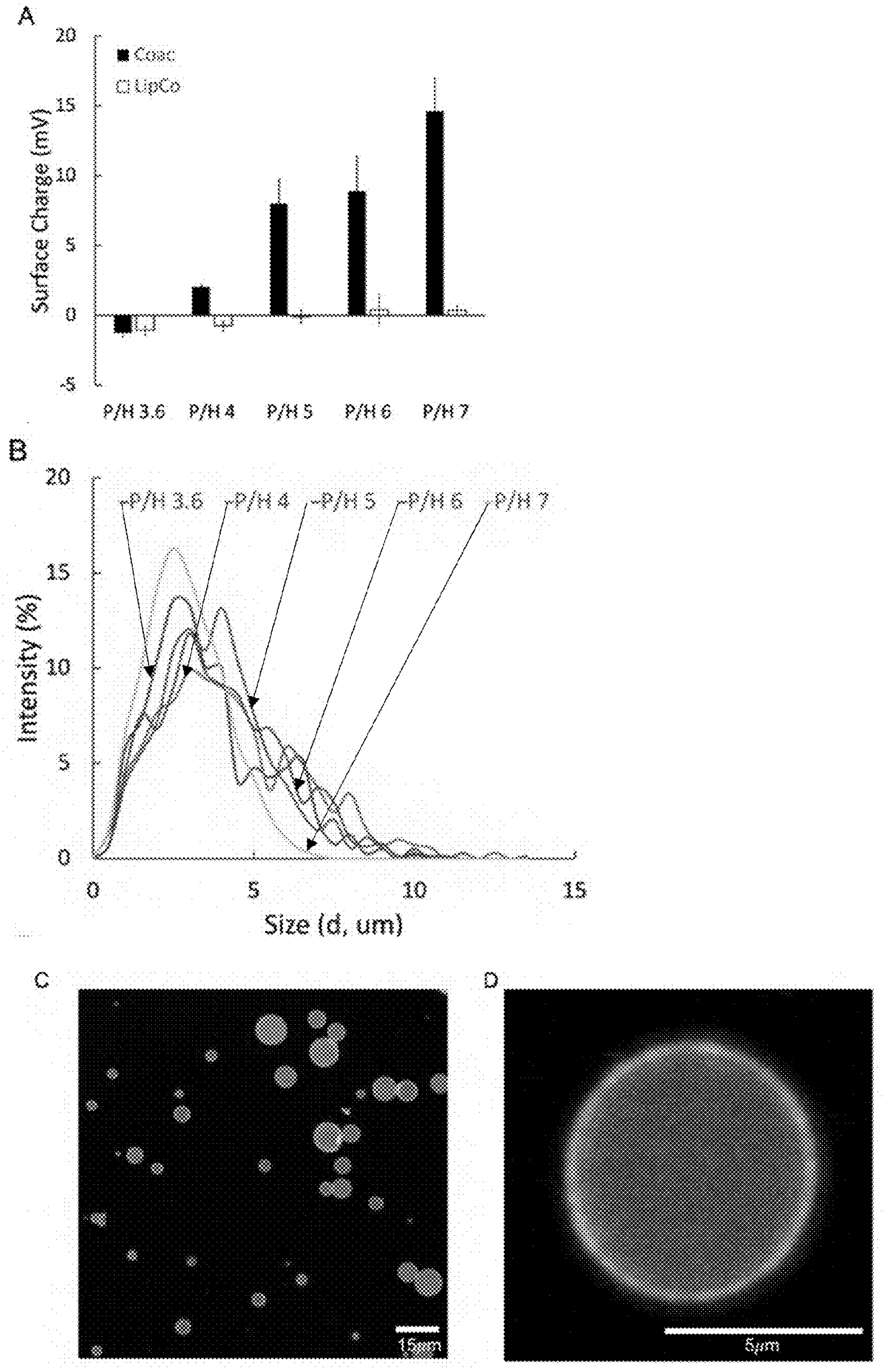
FIG. 1 shows characterization and confocal images of LipCo. A-Surface charge measurement of an aqueous dispersion of PEAD/heparin coacervate (Coac) and after the addition of DOPC/DSPG/cholesterol lipid mixture (LipCo) showing the charge reduction. B-LipCo size (in diameter) distribution with various PEAD to heparin mass ratios. C-Confocal microscopy image of LipCo showing the formed LipCo were discrete spheres. Scale bar: 15 μm. D-A high magnification image of LipCo. The green fluorescent interior of FITC-BSA loaded PEAD/heparin coacervate was enclosed via red fluorescent DOPC/DSPG/cholesterol lipid layer. Scale bar: 5 μm.

Although claimed subject matter will be described in terms of certain examples, other examples, including examples that do not provide all of the benefits and features set forth herein, are also within the scope of this disclosure. Various structural, logical, and process step changes may be made without departing from the scope of the disclosure.

As used herein, unless otherwise indicated, "about", "substantially", or "the like", when used in connection with a measurable variable (such as, for example, a parameter, an amount, a temporal duration, or the like) or a list of alternatives, is meant to encompass variations of and from the specified value including, but not limited to, those within experimental error (which can be determined by, e.g., a given data set, an art accepted standard, etc. and/or with, e.g., a given confidence interval (e.g. 90%, 95%, or more confidence interval from the mean), such as, for example, variations of +/−10% or less, +/−5% or less, +/−1% or less, and +/−0.1% or less of and from the specified value), insofar such variations in a variable and/or variations in the alternatives are appropriate to perform in the instant disclosure. As used herein, the term "about" may mean that the amount or value in question is the exact value or a value that provides equivalent results or effects as recited in the claims or taught herein. That is, it is understood that amounts, sizes, compositions, parameters, and other quantities and characteristics are not and need not be exact, but may be approximate and/or larger or smaller, as desired, reflecting tolerances, conversion factors, rounding off, measurement error, or the like, or other factors known to those of skill in the art such that equivalent results or effects are obtained. In general, an amount, size, composition, parameter, or other quantity or characteristic, or alternative is "about" or "the like," whether or not expressly stated to be such. It is understood that where "about," is used before a quantitative value, the parameter also includes the specific quantitative value itself, unless specifically stated otherwise.

Ranges of values are disclosed herein. The ranges set out a lower limit value and an upper limit value. Unless otherwise stated, the ranges include the lower limit value, the upper limit value, and all values between the lower limit value and the upper limit value, including, but not limited to, all values to the magnitude of the smallest value (either the lower limit value or the upper limit value) of a range. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "0.1% to 5%" should be interpreted to include not only the explicitly recited values of 0.1% to 5%, but also, unless otherwise stated, include individual values (e.g., 1%, 2%, 3%, and 4%) and the sub-ranges (e.g., 0.5% to 1.1%; 0.5% to 2.4%; 0.5% to 3.2%, and 0.5% to 4.4%, and other possible sub-ranges) within the indicated range. It is also understood (as presented above) that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further disclosure. For example, if the value "about 10" is disclosed, then "10" is also disclosed.

As used herein, unless otherwise stated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent and multivalent, such as, for example, divalent radicals, trivalent radicals, and the like). Illustrative, non-limiting examples of groups include:

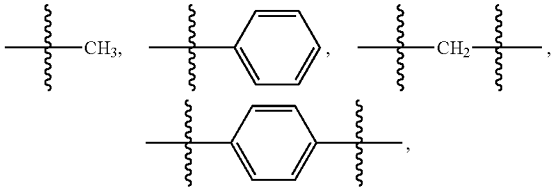

and the like.

As used herein, unless otherwise stated, the term "structural analog" refers to any compound that can be envisioned to arise from an original compound (e.g., component, biomolecule, or the like) if one atom or group of atoms, functional groups, or substructures is replaced with another atom or group of atoms, functional groups, substructures, or the like. In various examples, the term "structural analog" refers to any group that is derived from an original compound (e.g., component, biomolecule, or the like) by a chemical reaction, where the compound is modified or partially substituted such that at least one structural feature of the compound or group is retained.

The present disclosure provides, inter alia, lipocoacervates. The present disclosure also provides methods of making and using lipocoacervates.

In an aspect, the present disclosure provides lipocoacervates (LipCos). In various examples, as a condensation product of liquid-liquid phase separation comprising lipids disposed on at least a portion of the exterior surface of the condensation product. Non-limiting examples of lipocoacervates include lipocoacervates comprising lipid structures at least partially, substantially, or complete enclosing a coacervate, macromolecular condensates, biomolecular condensates, and the like. In various examples, a lipocoacervate is made by a method of the present disclosure. Non-limiting examples of lipocoacervates are described herein.

In various examples, a lipocoacervate (LipCo) (e.g., a LipCo droplet, a LipCo vesicle, or the like) comprises a coacervate phase (e.g., a droplet, a vesicle, or the like); and one or more lipid(s). In various examples, the lipid(s) is/are disposed on at least a portion of an exterior surface (or substantially all or all of the exterior surfaces) of the coacervate phase.

A lipocoacervate can comprise various coacervate phases. In various examples, a coacervate phase comprises (or is formed through) charge interactions or other weak bonds, or any combination thereof. In various examples, a coacervate phase is a simple coacervate, a complex coacervate, or the like. In various examples, a simple coacervate or the like comprises a single component (such as, for example, a multidomain polymer comprising two or more differently (e.g., oppositely) charged domains or the like). Non-limiting examples of multidomain polymers comprising two or more differently (e.g., oppositely) charged domains include elastin-like peptides and the like and any combination thereof. In various examples, a complex coacervate or the like comprises: one or more cationic component(s); and one or more anionic component(s). In various examples, a coacervate phase comprises two or more components (which may be single components, cationic component(s), anionic component(s), or any combination thereof).

In various examples, a coacervate phase is hydrophobic. In various examples, a coacervate, one or more or substantially all or all of the coacervate component(s) (such as, for example, a single component(s), a cationic component(s), anionic component(s), biomolecule(s), or the like or any combination thereof) are hydrophobic.

A lipocoacervate or a coacervate phase (such as, for example, a complex coacervate phase) can comprise various cationic components. In various examples, a coacervate phase comprises a single cationic component or a plurality of (e.g., two or more, three or more, etc.) different (e.g., compositionally different, structurally different, or functionally different, or any combination thereof) cationic components. In various examples, a cationic component is a polycation or the like. In various examples, one or more or all cationic component(s) (such as, for example, a polycation or polycations or the like) is/are endogenous. In various examples, a cationic component is a non-naturally-occurring polycation (e.g., synthetic polycation or the like) or the like. In various examples, a cationic component is a naturally-occurring polycation (such as, for example, chitosan, spermine, spermidine, or the like) or the like. Non-limiting examples of polycations include positively-charged polymers, positively-charged proteins, structural analogs thereof, and the like, and any combination thereof. Non-limiting examples of positively-charged polymers include polymers comprising one or more cationic amino acid(s), such as, for example, poly (ethylene argininylaspartate diglceride) and the like, polyamines (such as for example, spermine, spermidine, and the like), polysaccharides (such as, for example, chitosan and the like), structural analogs thereof, and the like, and any combination thereof. Non-limiting examples of positively-charged proteins include cationic gelatins, structural analogs thereof, and the like, and any combination thereof.

A lipocoacervate or a coacervate phase (such as, for example, a complex coacervate phase) can comprise various anionic components. In various examples, a coacervate phase comprises a single anionic component or a plurality of (e.g., two or more, three or more, etc.) different (e.g., compositionally different, structurally different, or functionally different, or any combination thereof) anionic components. In various examples, an anionic component is a polyanion the like. In various examples, an anionic component is a naturally-occurring polyanion or the like. In various examples, one or more or substantially all or all anionic component(s) is/are a biomolecule or biomolecules or the like. In various examples, an anionic component, which may be a biomolecule, is a therapeutic agent, a bioactive agent, a biofunctional agent, or the like, or any combination thereof. Non-limiting examples of anionic components include polyanions and the like, and any combination thereof. Non-limiting examples of polyanions include glycosaminoglycans (e.g., heparin, hyaluronic acid and the like), nucleic acids (e.g., RNAs, DNAs, and the like), negatively-charged proteins (e.g., anionic gelatins and the like), structural analogs thereof, and the like, and any combination thereof. In various examples, cationic component(s) and/or anionic component(s) is/are not polyelectrolytes or the like.

A lipocoacervate or a coacervate phase can comprise various amounts of cationic component(s) and/or anionic component(s). In various examples, the mass ratio of cationic component(s) to anionic component(s) is about 4 to about 1, including all 0.1 mass ratio values and ranges therebetween. In various examples, the mass ratio of cationic component(s) to anionic component(s) is chosen such that the lipocoacervate exhibits a desirable charge, which may be a surface charge or the like. In various examples, the mass ratio of cationic component(s) to anionic component(s) is chosen such that the lipocoacervate exhibits a charge of about +10 mV to about −10 mV, including all 0.1 mV values and ranges therebetween (e.g., +5 mV to about-5 mV), which may be a surface charge or the like. In various examples, the mass ratio of cationic component(s) to anionic component(s) is chosen such that the lipocoacervate exhibits a slightly positive charge (e.g., about +10 mV to about 0 mV, including all 0.1 mV values and ranges there between (e.g., about +5 mV to about 0 mV or about +1 mV to about 0 mV), which may be a positive surface charge or the like, or a slightly negative charge (e.g., about-10 mV to about 0 mV, including all 0.1 mV values and ranges therebetween (e.g., about-5 mV to about 0 mV or about-1 mV to about 0 mV), which may be a positive surface charge or the like.

A lipocoacervate can comprise various lipids. In various examples, a lipocoacervate comprises a single lipid or two or more (e.g., two or more, three or more, etc.) different (e.g., compositionally different, structurally different, or functionally different, or any combination thereof) lipids. The lipid components may be chosen to promote a desired vesicle rigidity, surface charge, or other properties, or any combination thereof, of the lipocoacervate. In various examples, a lipocoacervate comprises a shell (or a membrane or lipid membrane) comprising the lipid(s) disposed on (such as, for example, presented on or the like) at least a portion of, substantially all, or all of an exterior surface (or at least a portion of, substantially all, or all the exterior surfaces) of the coacervate phase. In various examples, a lipocoacervate comprises a shell (or a membrane or lipid membrane) comprising one or more unsaturated lipid(s), one or more saturated lipid(s), or the like or any combination thereof. In various examples, the shell comprising the lipid(s) (such as, for example, the phospholipid(s) or the like) substantially encapsulates, encapsulates, or the like the coacervate phase.

Non-limiting examples of lipids include fats, oils, waxes, vitamins (such as, for example, vitamin A, vitamin D, vitamin E, vitamin K, and the like), hormones, phospholipids (such as, for example, phosphatidylglycerols (PGs) (e.g., 18:0 PG, 17:0 PG, 16:0 PG, 18:2 PG, 20:4 PG and the like), phosphatidylserines (PSs) (e.g., 1,2-di-(9Z-octadecenoyl)-sn-glycero-3-phospho-L-serine (DOPS), 18:2 PS, 22:6 PS, 18:0 PS, 17:0 PS, and the like), phosphatidic acids (PAS) (e.g., 18:0 PA, 18:1 PA, 18:2 PA, 17:0 PA, 16:0 PA, and the like), and the like), glycerolipids, glycerophospholipids (such as, for example, phosphatidylethanolamines (PEs) (e.g., 18:0 PE, 17:0 PE, 10:0 PE, 16:1 PE, 18:2 PE, and the like), phosphatidylcholines (PCs) (e.g., 06:0 PC (1,2-dihexanoyl-sn-glycero-3-phosphocholine (DHPC), 2:0 PC (1,2-dilauroyl-sn-glycero-3-phosphocholine (DLPC), 6:0 PC (1,2-dipalmitoyl-sn-glycero-3-phosphocholine (DPPC), 14:0 PC (1,2-dimyristoyl-sn-glycero-3-phosphocholine (DMPC), 18:0 PC (1,2-distearoyl-sn-glycero-3-phosphocholine (DSPC), 8:1 (49-Cis) PC (1,2-dioleoyl-sn-glycero-3-phosphocholine (DOPC), 34:1 PC (1-palmitoyl-2-oleoyl-glycero-3-phosphocholine (POPC), and the like)), sphingolipids (such as, for example, sphingomyelin, ceramides, and the like), sterols (such as, for example, cholesterol, or the like), glycolipids, gangliosides (such as, for example, total ganglioside extract and the like), salts thereof (where appropriate), such as, for example, sodium salts and the like, structural analogs thereof, and the like, and any combination thereof. Non-limiting examples of phospholipids include anionic phospholipids structural analogs thereof, and the like. In various examples, one or more or substantially all or all the lipid(s) are polar lipid(s) or the like. In various examples, the lipid(s) comprise(s) dioleoylphosphatidylcholine (DOPC), 1,2-Distearoyl-sn-glycero-3-phospho-rac-glycerol (DSPG), dipalmitoylphosphatidylcholine (DPPC), structural analogs thereof, or a salt thereof, or the like, or any combination thereof. In various examples, a lipid is not a PEGylated lipid (a lipid comprising a poly(ethylene glycol) group) or the like.

In various examples, a lipocoacervate (or a lipocoacervate shell, such as, for example, a shell comprising one or more lipid(s)) comprises cholesterol, or a structural analog thereof, or the like. Without intending to be bound by any particular theory, it is considered cholesterol provides an increase in the of lipid packing, stabilizing the lipid shell (e.g., against structural damage or the like), or both.

A lipocoacervate can comprise various amounts of coacervate phase (such as, for example, single component(s), cationic component(s), cationic component(s) or any combination thereof) and lipid(s). In various examples, a lipocoacervate comprises a coacervate phase to lipid(s) mass ratio of about 95:5 to about 99.9997:0.0003, including all 0.0001 mass ratio values and ranges therebetween (e.g., about 98:2 to about 99.9997:0.0003, about 99:1 to about 99.9997:0.0003, about 99.9:0.1 to about 99.9997:0003, about 99.99:0.01 to about 99.9997:0.0003, 98:2 to about 99.9995:0.0005, about 99:1 to about 99.9995:0.0005, about 99.9:0.1 to about 99.9995:0.0005, about 99.99:0.01 to about 99.9995:0.0005, 98:2 to about 99.999:0.001, about 99:1 to about 99.999:0.001, about 99.9:0.1 to about 99.999:0.001, or about 99.99:0.01 to about 99.999:0.001).

A lipocoacervate may further comprise a biomolecule or two or more different (e.g., compositionally different, structurally different, or functionally different, or any combination thereof) biomolecules. In various examples, a biomolecule comprises as a net neutral charge, a net positive charge, or a net negative charge. In various examples, biomolecule or biomolecule(s) (such as, for example, therapeutic agent(s), bioactive agent(s), biofunctional agent(s), or the like, or any combination thereof) is/are at least partially or completely sequestered or at least partially or completely encapsulated within, or the like in the coacervate phase. In various examples, a biomolecule is loaded into (or interacts with one or more coacervate component(s) of) a coacervate phase by one or more weak bond(s) (such as, for example, charge interaction(s), hydrogen bonding, Van der Waals forces, molecular entanglement, or the like).

In various examples, a biomolecule is a therapeutic agent, a bioactive agent, a biofunctional agent, or the like, or any combination thereof. In various examples, a coacervate phase comprises one or more biomolecule(s), where the biomolecule(s) is/are, independently, a therapeutic agent, a bioactive agent, a biofunctional agent, or the like. Non-limiting examples of therapeutic agents include small molecule drugs, nucleic acids (such as, for example, RNAs (e.g., single-stranded RNA, double-stranded RNA, microRNA, and the like), DNAs (e.g., single-stranded DNA, double-stranded DNA, plasmid DNA, and the like), and the like), proteins, and structural analogs thereof, therapeutic morpholinos, morphogens (such as, for example, Sonic Hedgehog (Shh), and the like, and any combination thereof. In various examples, a bioactive agent exhibits signaling behavior and/or participates in signaling, analogous to a small molecule drug, a hormone, or the like, and/or is soluble and/or diffusible. In various examples, a biofunctional agent exhibits and/or participates lock-key enzymatic activity, which may be soluble or insoluble (such as, for example, ECM-integrin binding where both partners anchored, not dissolved, or the like) and/or is soluble or insoluble. Non-limiting examples of biofunctional agents include hemoglobin, and the like, and any combination thereof. Non-limiting examples of biomolecules include proteins and the like and any combination thereof. In various examples, a biomolecule is a protein or the like. Non-limiting examples of proteins include growth factors (such as, for example, vascular endothelial growth factors (VEGFs), fibroblast growth factors (FGFs), and the like, any combination thereof), cytokines, interleukins (IL-2, IL-4, IL-6, IL-10, IL-12, and the like), and the like, and any combination thereof. In various examples, a biomolecule is heparin, bovine serum albumin (BSA), adenosine triphosphate (ATP), and the like, and any combination thereof.

A lipocoacervate may comprise various amounts of biomolecule(s). In various examples, a biomolecule or biomolecules is/are present at about 1 weight percent (wt. %) to about 60 wt. % (based on the total weight of the biomolecule(s) and coacervate phase), including all 0.1 weight percent values and ranges therebetween (e.g., about 20 wt. % to about 60 wt. %).

In various examples, a lipocoacervate is a fluorescent lipocoacervate. In various examples, a component (e.g., a cationic component, an anionic component, a biomolecule, or the like) comprises one or more fluorescent group(s). In various examples, a component (e.g., a cationic component, an anionic component, a biomolecule, or the like) comprises one or more fluorescent group(s) conjugated to the component, is inherently fluorescent, or the like. Non-limiting examples of fluorescent groups include fluorescent dye groups (e.g., groups formed from fluorescent dyes or the like), fluorescent proteins (e.g., groups formed from fluorescent proteins or the like), or the like. In various examples, a lipocoacervate further comprises a localization tag. A localization tag can be used to determine the location of a lipocoacervate (such as, for example, the location of a lipocoacervate in a cell, a plurality of cells, or an individual). In various examples, a localization tag is a fluorescent tag (comprising one or more fluorophore(s) or the like) or the like.

In various examples, coacervate phase and/or a lipocoacervate comprises substantially spherical shape (e.g., spherical) or the like. In various examples, a lipocoacervate comprises or exhibits a size (e.g., a longest linear dimension (such as, for example, a diameter or the like) or the like) of about 100 nanometers (nm) to about 20 micrometers (microns), including all 0.1 nanometer values and ranges therebetween. In various examples, the lipocoacervate size (e.g., longest linear dimension or the like) is determined by optical microscopy, electron microscopy, light scattering, or the like, or any combination thereof.

In various examples, a lipocoacervate exhibits (or does not exhibit (e.g., exhibits a neutral net surface charge)) a net surface charge (such as, for example, a positive net surface charge or a net negative surface charge). In various examples, a coacervate phase exhibits (or does not exhibit (e.g., exhibits a neutral net surface charge)) a net surface charge (such as, for example, a slightly positive or positive net surface charge or a slightly negative or negative net surface charge). In various examples, the lipid(s) exhibit/exhibits (or does not exhibit (e.g., exhibits a neutral net charge)) a net charge (such as, for example, a slightly positive or positive net charge or a slightly negative or negative net charge).

A lipocoacervate can comprise a desirable surface charge. In various examples, a lipocoacervate comprises or exhibits a zeta potential of from about-5 millivolts (mV) to about +5 mV, including all 0.1 mV values and ranges therebetween (e.g., −4 mV to about +0.5 mV). In various examples, a lipocoacervate comprises or exhibits a zeta potential of about 0 mV.

In various examples, a lipocoacervate is stable. In various examples, a stable lipocoacervate does not exhibit substantial or any aggregation (such as, for example, observable aggregation (e.g., observable by optical microscopy, electron microscopy, light scattering, or the like, or any combination thereof) or the like), a substantial change or any change (such as, for example, an observable change (e.g., by optical microscopy, electron microscopy, light scattering, or the like, or any combination thereof)) in size (such as, for example, a longest linear dimension (such as, for example, a diameter or the like)) for at least one-week or more (e.g., at least two-weeks or more, at least three-weeks or more, at least four-weeks or more) at a temperature of about 4 degrees Celsius (° C.), or both.

A lipocoacervate or lipocoacervates can exhibit desirable circulation time, controlled biomolecule release, or both. In various examples, a lipocoacervate or lipocoacervates exhibit(s) a circulation time of at least one day, at least three days, at least one week, or more. In various examples, a lipocoacervate or lipocoacervates exhibit(s) a half life (e.g., a circulation half life or the like) of 2 hours or more, 5 hours or more, or 10 hours or more, one day or more, or 5 days or more. In various examples, a lipocoacervate or lipocoacervates exhibits release of 10% or less of the biomolecules (e.g., in an individual) in one week.

In an aspect, the present disclosure provides compositions. In various examples, a composition comprises a plurality of lipocoacervates of the present disclosure. In various examples, a composition is a pharmaceutical composition. In various examples, a composition is made by a method of the present disclosure. Non-limiting examples of compositions are described herein.

In various examples, a composition comprises substantially the same or the same lipocoacervates. In various examples, all the lipocoacervates in a composition comprise substantially the same composition and/or substantially the same size. In various examples, one or more or all the lipocoacervate(s) in a composition comprise a different composition and/or size than the other lipocoacervates of the composition. In various examples, a composition comprises a plurality of (e.g., two or more, three or more, etc.) different (e.g., compositionally different, structurally different, or functionally different, or any combination thereof) lipocoacervates. In various examples, at least a portion of, substantially all, or all the lipocoacervates in a composition comprise independently comprise one or more biomolecule(s).

In various examples, at least a portion, substantially all, or all the lipocoacervates in a composition comprise or exhibit an average size (e.g., an average longest linear dimension (such as, for example, an average diameter or the like) or the like of about 100 nm to about 20 microns, including all 0.1 nm values and ranges therebetween. In various examples, about 90% or more, about 95% or more, about 98% or more, about 99% or more, about 99.9% or more, or about 100% of the lipocoacervates in a composition comprise or exhibit an average size (e.g., an average longest linear dimension (such as, for example, an average diameter or the like) or the like of about 100 nm to about 20 microns, including all 0.1 nm values and ranges therebetween. In various examples, the average size (such as, for example, the longest linear dimension or the like) is determined by optical microscopy, electron microscopy, light scattering, or the like, or any combination thereof.

A composition can comprise various amounts of lipocoacervates. In various examples, lipocoacervates are present in a composition at about 1 wt. % to about 80 wt. % (based on the total weight of the composition), including all 0.1 values and ranges therebetween (e.g., about 1 wt. % to about 75 wt. %, or about 5 wt. % to about 60 wt. %).

In various examples, a composition (which may be a pharmaceutical composition) further comprises one or more additional component(s), one or more or all of which may be pharmaceutically acceptable components. Non-limiting examples of compositions are described herein.

As used herein, unless otherwise indicated, the term "pharmaceutically acceptable" refers to those components and dosage forms that are, within the scope of sound medical judgment, suitable for use in contact with the tissues of humans or animals without undesirable or excessive toxicity, irritation, or other problem or complication, which may be commensurate with a reasonable benefit/risk ratio.

Some non-limiting examples of materials which can be used as additional component(s) in a composition include sugars, such as, for example, lactose, glucose, sucrose, and the like; starches, such as, for example, corn starch, potato starch, and the like; cellulose, and its derivatives, such as, for example, sodium carboxymethyl cellulose, ethyl cellulose, cellulose acetate, and the like; powdered tragacanth; malt; gelatin; talc; excipients, such as, for example, cocoa butter, suppository waxes, and the like; oils, such as, for example, peanut oil, cottonseed oil, safflower oil, sesame oil, olive oil, corn oil, soybean oil, and the like; glycols, such as, for example, propylene glycol and the like; polyols, such as, for example, glycerin, sorbitol, mannitol, polyethylene glycol, and the like; esters, such as, for example, ethyl oleate, ethyl laurate, and the like; agar; buffering agents, such as, for example, magnesium hydroxide, aluminum hydroxide, and the like; alginic acid; pyrogen-free water; isotonic saline; Ringer's solution; ethyl alcohol; phosphate buffer solutions; and other non-toxic compatible substances employed in pharmaceutical formulations. (See, e.g., REMINGTON'S PHARM. SCI., 15th Ed. (Mack Publ. Co., Easton (1975) and Remington: The Science and Practice of Pharmacy (2012) 22nd Edition, Philadelphia, PA. Lippincott Williams & Wilkins.

In various examples, a composition is a solution (such as, for example, a saline solution or the like). In various examples, a composition is an aqueous dispersion, or the like. In various examples, a composition does not comprise a hydrogel or the like.

A composition (or the lipocoacervates of a composition) can comprise a desirable surface charge or average surface charge. In various examples, a composition (or the lipocoacervates of a composition) comprise(s) or exhibit(s) an average zeta potential of about-5 millivolts (mV) to about +5 mV, including all 0.1 mV values and ranges therebetween (e.g., −4 mV to about +4 mV). In various examples, a composition (or the lipocoacervates of a composition) comprise(s) or exhibit(s) an average zeta potential of about 0 mV.

In various examples, a composition is stable. In various examples, a stable composition does not exhibit substantial or any lipocoacervate aggregation (observable aggregation (e.g., by optical microscopy, electron microscopy, light scattering, or the like, or any combination thereof) or the like), a substantial change or any change (observable change (e.g., by optical microscopy, electron microscopy, light scattering, or the like, or any combination thereof) in lipocoacervate size (such as, for example, average lipocoacervate size) (such as, for example, a longest linear dimension (such as, for example, a diameter or the like)) for at least one-week or more (e.g., at least two-weeks or more, at least three-weeks or more, at least four-weeks or more) at a temperature of about 4 degrees Celsius (° C.), or both. In various examples, a stable composition does not exhibit a change (observable change (e.g., by optical microscopy, electron microscopy, light scattering, or the like, or any combination thereof) in lipocoacervate size (such as, for example, average lipocoacervate size) (such as, for example, a longest linear dimension (such as, for example, a diameter or the like)) of greater than about 5%, greater than about 4%, greater than about 3%, greater than about 2%, greater than about 1%, greater than about 0.5%, or greater than about 0.1%, or greater, 2% or greater, of the lipocoacervate for at least one-week or more (e.g., at least two-weeks or more, at least three-weeks or more, at least four-weeks or more) at a temperature of about 4 degrees Celsius (° C.), or both.

In an aspect, the present disclosure provides methods of making lipocoacervates. In various examples, a method makes a lipocoacervate or a composition of the present disclosure. Non-limiting examples of methods of making a lipocoacervate or a composition of the present disclosures of the present disclosure are described herein.

In various examples, a method of making lipocoacervates (or a lipocoacervate composition) comprises providing a coacervate composition (e.g., a coacervate solution or the like); and contacting the coacervate composition with a lipid composition, where the lipocoacervates are (or a lipocoacervate composition is) formed. In various other examples, a method of making lipocoacervates (or a lipocoacervate composition) comprises contacting a coacervate composition with a lipid composition, where the lipocoacervates are or the lipocoacervate composition is formed.

Various coacervate compositions can be used. In various examples, a coacervate composition forms or is a coacervate phase described herein.

In various examples, a coacervate composition comprises coacervate domains comprising a surface charge (such as, for example, a positive surface charge or the like) and/or the lipids comprise a negative charge. Without intending to be bound by any particular theory it is considered the surface charge state of the coacervate domains and opposite lipid charge results in formation of lipocoacervates or a lipocoacervate composition.

In various examples, a coacervate composition comprises one or more hydrophobic material(s) or the like. In various examples, a coacervate composition comprises one or more single component(s) (such as, for example, a multidomain polymer(s), each independently comprising two or more differently (e.g., oppositely) charged domains or the like). In various examples, a coacervate composition comprises one or more cationic material(s) (e.g., cationic component(s), such as, for example, cationic components described herein) or the like. In various examples, a coacervate composition comprises one or more cationic material(s) and one or more anionic material(s) (e.g., anionic component(s), such as, for example, anionic components described herein) or the like. In various examples, one or more or all the anionic component(s) is/are a biomolecule or biomolecules, such as for example, therapeutic agent(s), bioactive agent(s), biofunctional agent(s), or the like. In various examples, the mass ratio of cationic component(s) to anionic component(s) is about 4 to about 1, including all 0.1 mass ratio values and ranges therebetween.

In various examples, a coacervate composition is also contacted with two or more lipid compositions, where each lipid composition comprises one or more different lipid(s) than the other lipid composition(s). In various examples, the coacervate composition is contacted with the lipid compositions in any order (such as, for example, at the same time, sequentially, or the like) and/or at any time interval.

In various examples, the coacervate material(s) to lipid(s) mass ratio is about 95:5 to about 99.999:0.0003, including all 0.0001 mass ratio values and ranges therebetween (e.g., about 98:2 to about 99.9997:0.0003, about 99:1 to about 99.9997:0.0003, about 99.9:0.1 to about 99.9997:0003, about 99.99:0.01 to about 99.9997:0.0003, 98:2 to about 99.9995:0.0005, about 99:1 to about 99.9995:0.0005, about 99.9:0.1 to about 99.9995:0.0005, about 99.99:0.01 to about 99.9995:0.0005, 98:2 to about 99.999:0.001, about 99:1 to about 99.999:0.001, about 99.9:0.1 to about 99.999:0.001, or about 99.99:0.01 to about 99.999:0.001). In various examples, the lipid(s) is/are present at a slight molar excess relative to the coacervate materials(s) (such as, for example, about a 1% molar excess or about a 2% molar excess).

In various examples, a coacervate composition is formed by forming a solution, which may be an aqueous solution or the like, of two or more materials (e.g., by mixing or the like), and optionally, one or more biomolecule(s). In various examples, a coacervate composition is formed by forming an aqueous solution of or comprising one or more hydrophobic material(s) or the like, and optionally, one or more biomolecule(s). In various examples, a coacervate composition is formed by forming or contacting (e.g., mixing or the like) an aqueous solution of or comprising one or more single component(s) and/or one or more cationic component(s) and one or more anionic component(s) and, optionally, one or more biomolecule(s).

In various examples, a coacervate composition and/or lipid composition is/are a solution or solutions (such as, for example, a saline solution or saline solutions, or the like). In various examples, a lipid composition is/are an organic solvent(s) solution or the like. In various examples, a coacervate composition and/or a lipid composition comprises about 1 wt. % to about 40 wt. % (e.g., based on the total weight of the composition), including all 0.1 wt. % values and ranges therebetween (e.g., about 1 wt. % to about 20 wt. % or about 1 wt. % to about 30 wt. %). In various examples, a lipid composition comprises about 100 wt. % lipid(s). In various examples, a lipid composition further comprises one or more alcohol(s) (such as, for example, ethanol or the like).

A reaction (e.g., individual contacting) can be performed under various reaction conditions. A reaction can comprise one or more step(s) and each step can be performed under the same or different reaction conditions as other steps. A reaction can be carried out at various temperatures. In various examples, a reaction is carried out at room temperature (e.g., from about 20° C. to about 22° C., including all 0.1° C. values and ranges therebetween), below room temperature (e.g., at a temperature above the freezing point of any of the reaction components), above room temperature (e.g., at a temperature up to or about a lowest degradation temperature (e.g., denature temperature, if applicable) of any of the reaction components (e.g., at about 40° C. or lower) (e.g., where each step is performed at the same or different temperature as the other steps).

A reaction (e.g., individual contacting) can be carried out at various pressures. In various examples, a reaction is carried out at about atmospheric pressure (e.g., about 1 standard atmosphere (atm) at sea level) (e.g., where each step is performed at the same or different pressure as the other steps).

A reaction (e.g., individual contacting) can be carried out for various times. The reaction time can depend on factors such as, for example, one or more or all of (if applicable) temperature, pressure, presence and/or intensity of an applied energy source, stirring/mixing, or the like. In various examples, reaction times range from about seconds (e.g., two seconds) to about 8 hours, including all integer second values and ranges therebetween (e.g., from about 1 minute to about 1 hour or from about 1 minute to about 4 hours) (e.g., where each step is performed at the same or different time as the other steps).

In various examples, a method further comprises isolating the lipocoacervates. In various examples, the lipocoacervates are isolated by centrifugation, filtration (such as, ultrafiltration) dialysis, or the like.

In an aspect, the present disclosure provides uses of a lipocoacervate or a composition of the present disclosure. Non-limiting examples of uses of a lipocoacervate or a composition of the present disclosure are described herein.

In various examples, a lipocoacervate or lipocoacervates of the present disclosure or a composition or compositions of the present disclosure is used in biomolecule delivery methods, which may be intracellular biomolecule delivery methods. In various examples, a method of biomolecule delivery comprises contacting a population of cells, an individual, or the like, with one or more or a plurality of lipocoacervate(s) and/or one or more composition(s), where at least a portion of or all of the lipocoacervate(s) (or biomolecule(s) is/are delivered to the population of cells, the individual, or the like. In various examples, the delivery is intracellular delivery or the like.

In various examples, a method comprises delivery (e.g., in vivo delivery, in vitro delivery, or the like) of a lipocoacervate or lipocoacervates and/or or one or more biomolecule(s) (such as, for example, a protein, proteins, or the like) of a lipocoacervate or lipocoacervates to a cell or a population of cells, or the like. In various examples, a method comprises delivery of a lipocoacervate or lipocoacervates and/or or one or more biomolecule(s) (such as, for example, a protein, proteins, or the like) of a lipocoacervate or lipocoacervates (which may be an effective amount thereof) to an individual. In various examples, a method comprises intracellular delivery of a lipocoacervate or lipocoacervates and/or or one or more biomolecule(s) (such as, for example, a protein, proteins, or the like) of a lipocoacervate or lipocoacervates.

In various examples, a lipocoacervate or lipocoacervates are used in treatment methods. In various examples a method comprises treating, preventing, or the like, or any combination thereof, a current or potential disease, disease state, condition, disorder, side effect, or the like, or any combination thereof, in an individual.

In various examples, a treatment method comprises delivery (such as, for example, intracellular delivery) of a lipocoacervate or lipocoacervates and/or or one or more biomolecule(s) of a lipocoacervate or lipocoacervates or administration (which may be an effective amount thereof) of a lipocoacervate or lipocoacervates and/or or one or more biomolecule(s) of a lipocoacervate or lipocoacervates and/or one or more composition(s) to an individual. An individual (e.g., an individual in need of treatment or the like) may be a human or other animal (which may be a non-human mammal). In various examples, an individual is a mammal. Non-limiting examples of non-human animals (which may be mammals) include cows, pigs, mice, rats, rabbits, and other agricultural animals, pets (such as, for example, dogs, cats, and the like), service animals, and the like. In various examples, an individual is diagnosed with and/or is in need of treatment for a disease, disease state, or the like, and the disease, the disease state, or the like is treatable, preventable, or the like, by one or more or all the biomolecule(s).

In various examples, a method comprises targeting, diagnosing, treating, preventing, or the like, or any combination thereof, a current or potential disease, disease state, condition, disorder, side effect, or the like, or any combination thereof, in an individual by administration of a lipocoacervate or lipocoacervates and/or or one or more biomolecule(s) of a lipocoacervate or lipocoacervates and/or one or more composition(s) to the individual. In various examples, the current or potential disease, disease state, condition, disorder, side effect, or the like, or any combination thereof, is chosen from infections, cancers, neurological conditions/diseases, neurodegenerative diseases, psychological conditions/diseases, inflammatory conditions/diseases, cardiovascular diseases, autoimmune conditions/diseases, and the like, and any combination thereof. In various examples, it is considered the current or potential disease, disease state, condition, disorder, side effect, or the like, or any combination thereof, is any current or potential disease, disease state, condition, disorder, side effect, or the like, or any combination thereof, that is targetable, diagnosable, treatable, preventable, or the like, or any combination thereof, by one or more biomolecule(s) of a lipocoacervate or lipocoacervates. Without intending to be bound by any particular theory, it is considered lipocoacervate(s) can be used, in various examples, to alter and/or control the immune system of an individual, to treat autoimmune diseases, cancer (such as, for example, tumors and the like), and the like. In various examples, therapeutic agent(s) (such as, for example, therapeutic molecules and the like) can be delivered by lipocoacervate(s) to treat inflammatory diseases, such as, for example, arthrosclerosis, ischemic diseases, such as, for example, stroke, myocardial infarction, and the like. In various examples, a method is used to treat diabetes or the like. As used herein, “treatment” of diabetes is not limited to treatment, but encompasses alleviation of one or more or all of the symptom(s) of the disease, the disease state, or the like.

“Treating” or “treatment” of any disease or disorder refers, in various examples, to ameliorating (e.g., arresting, reversing, alleviating, or the like) the disease, disease state, condition, disorder, side effect, or the like, or a combination thereof the disease, disease state, condition, disorder, side effect, or the like, or a combination thereof, or reducing the manifestation, extent or severity of one or more clinical symptom(s) thereof, or the like). In various other examples, “treating” or “treatment” refers to ameliorating (e.g., arresting, reversing, alleviating, or the like) one or more physical parameter(s), which, independently, may or may not be discernible by the individual. In yet other examples, “treating” or “treatment” refers to modulating disease, disease state, condition, disorder, side effect, or the like, or a combination thereof, either physically (e.g., stabilization of one or more discernible symptom(s), or the like), physiologically (e.g., stabilization of one or more physical parameter(s), or the like), or both. In yet other examples, treating” or “treatment” relates to slowing the progression of the disease, disease state, condition, disorder, side effect, or the like, or a combination thereof.

As used herein, unless otherwise indicated, the term “effective amount” means that amount of lipocoacervate(s) and/or biomolecule(s) that will (or is expected to) elicit the biological or medical response of an individual (or a tissue, system, or the like, thereof) that is being sought, for instance, by a researcher, clinician, or the like. An effective amount may be a therapeutically effective amount. The term “therapeutically effective amount” includes any amount which, as compared to a corresponding individual who has not received such amount, results in improved treatment, healing, prevention, or amelioration (e.g., arresting, reversing, alleviating, or the like) of a disease, disease state, condition, disorder, side effect, or the like or a decrease in the rate of advancement of a disease, disease state, condition, disorder, or the like, or the like. The term also includes within its scope amounts effective to enhance normal physiological function. In various examples, the individual is considered effectively treated if the treated individual is not thereafter diagnosed with the disease or disease state, or one or more symptom(s), one or more indication(s), or the like of condition, disorder, disease, or disease state, or the like is at least partially or completely prevented, inhibited, alleviated, or the like).

In various examples, an effective amount results in prophylaxis or the like of a disease, disease state, condition, disorder, side effect, or the like. The term “prophylaxis” includes prevention and refers to a measure or procedure which is to prevent rather than cure or treat a disease. Preventing may refer to a reduction in risk of acquiring or developing a disease, disease state, condition, disorder, side effect, or the like causing one or more clinical symptom(s) the disease, disease state, condition, disorder, side effect, or the like not to develop in an individual that may be exposed to a disease causing agent or an individual predisposed to the disease in advance of disease outset.

A physician or veterinarian having ordinary skill in the art can readily determine and prescribe the effective amount of the lipocoacervate(s) and/or biomolecule(s) and/or composition(s) required. A selected dosage level can depend upon a variety of factors including, but not limited to, the activity of the particular composition employed, the time of administration, the rate of excretion or metabolism of the particular composition being employed, the rate and extent of absorption, the duration of the treatment, other drugs, compounds and/or materials used in combination with the particular composition employed, the age, sex, weight, condition, general health and prior medical history of the patient being treated, and like factors well known in the medical arts. For example, a physician or veterinarian could start doses of a lipocoacervate or lipocoacervates and/or a composition or compositions employed at levels lower than that required in order to achieve the desired therapeutic effect and gradually increase the dosage until the desired effect is achieved.

In various examples, a lipocoacervate or lipocoacervates and/or a composition or compositions is suitable for (or the administration is) intravenous, subcutaneous, intramuscular, intra-joint, parenteral, intra-arteriole, intradermal, intraventricular, intraocular, intracranial, intraperitoneal, intralesional, intranasal, intracardiac, intraarticular, intracavernous, intrathecal, intravireal, intracerebral, and intracerebroventricular, intratympanic, intracochlear, interstitial, intra-abdominal, intra-amniotic, intra-arterial, intraarticular, intracardiac, intracartilaginous, intracaudal, intracavernous, intracavitary, intracerebral, intracisternal, intracorneal, intracoronal (dental), intracoronary, intracorporus cavernosum, intraductal, intraduodenal, intradural, intraepidermal, intraesophageal, intragastric, intraileal, intralesional, intraluminal, intralymphatic, intramedullary, intrameningeal, intraovarian, intrapericardial, intrapleural, intraprostatic, intrapulmonary, intrasinal, intraspinal, intrasynovial, intratesticular, subarachnoid, subconjunctival, sublingual, submucosal, transplacental, or transtympanic administration, or the like, or any combination thereof administration. In various examples, a lipocoacervate or lipocoacervates and/or a composition or compositions is suitable for delivery using a catheter or the like or the administration is via catheter.

In various examples, contacting comprises administration of the plurality of lipocoacervates to an individual. In various examples, administration of the lipocoacervate(s) (such as, for example, administration of the biomolecule(s) or the like) results in treating, preventing, or the like, or any combination thereof, a current or potential disease, disease state, condition, disorder, side effect, or the like, or any combination thereof, in the individual. In various examples, the lipocoacervate(s) is/are taken up by a cell or cells of the population of cells or the individual, and lipocoacervate(s) is/are is released within the cell or cells. In various examples, at least a portion or all of the lipocoacervates comprises one or more biomolecule(s) (such as, for example, protein(s) or the like, or any combination thereof) and the biomolecule(s) (such as, for example, protein(s) or the like, or any combination thereof) retain/retains (e.g., after delivery) substantially all (or all) structural features and/or 50% or more, 70% or more, 90% or more, or 95% or more biological activity compared with the native biomolecule(s) (such as, for example, native protein(s) or the like, or any combination thereof) delivered without use of a lipocoacervate/lipocoacervates.

In various examples, one or more lipocoacervate(s) and/or one or more compositions of the present disclosure are used the preparation of a medicament. In various examples, a medicament is suitable for treatment for a disease, disease state, or the like, and the disease, the disease state, or the like is treatable, preventable, or the like, by the biomolecule(s). In various examples, a medicament is suitable for administration to an individual diagnosed with and/or is in need of treatment for a disease, disease state, or the like, and the disease, the disease state, or the like is treatable, preventable, or the like, by the biomolecule(s).

In an aspect, the present disclosure provides kits. In various examples, a kit comprises a lipocoacervate or lipocoacervates and/or composition(s) of the present disclosure. Non-limiting examples of kits are provided herein.

In various examples, a kit comprises a lipocoacervate or lipocoacervates and/or composition(s) of the present disclosure and/or one or more starting material(s) for any of same. In various examples, a kit includes a closed or sealed package that comprises the lipocoacervate or lipocoacervates and/or the composition(s). In various examples, the package comprises one or more closed or sealed vials, bottles, blister (bubble) packs, or any other suitable packaging for the sale, distribution, or use of the lipocoacervate(s) and/or the composition(s) and/or starting material(s). The printed material may include printed information. The printed information may be provided on a label, on a paper insert, printed on a packaging material, or the like. The printed information may include information that identifies the lipocoacervate(s) and/or the composition(s) and/or starting material(s) in the package, the amounts and types of other active and/or inactive ingredients in the lipocoacervate(s) and/or the composition(s) and/or starting material(s), and instructions for taking (e.g., administration or the like) the lipocoacervate(s) and/or the composition(s) and/or starting material(s). The instructions may include information, such as, for example, the number of doses to take over a given period of time, and/or information directed to a pharmacist and/or another health care provider, such as, for example, a physician or the like, or a patient. The printed material may include an indication or indications that the lipocoacervate(s) and/or the composition(s) and/or starting material(s) and/or any other agent provided therein is for treatment of an individual. In various examples, the kit includes a label describing the contents of the kit and providing indications and/or instructions regarding use of the contents of the kit to treat an individual.

The following Statements describe various examples of lipocoacervates, compositions, methods of making lipocoacervates, and uses of coacervates of the present disclosure and are not intended to be in any way limiting:

Statement 1. A lipocoacervate (LipCo) (e.g., a LipCo droplet, a LipCo vesicle, or the like) comprising: a coacervate phase (e.g., a droplet, a vesicle, or the like); and one or more lipid(s), where the lipid(s) is/are disposed on at least a portion of an exterior surface (or substantially all or all of the exterior surfaces) of the coacervate phase.

Statement 2. A LipCo according to Statement 1, where the coacervate phase (e.g., a simple coacervate or the like) comprises a single component (such as, for example, a multidomain polymer comprising two or more differently (e.g., oppositely) charged domains or the like).

Statement 3. A LipCo according to Statement 1, where the coacervate phase (e.g., a complex coacervate or the like) comprises: one or more cationic component(s); and one or more anionic component(s).

Statement 4. A LipCo according to Statement 3, where the cationic component is chosen from polycations (such as, for example, poly(ethylene argininylaspartate diglceride), chitosan, spermine, spermidine, positively-charged proteins, and the like, and any combination thereof), and the like, or any combination thereof.

Statement 5. A LipCo according to Statement 3 or 4, where the anionic component is chosen from polyanions (such as, for example, glycosaminoglycans (e.g., heparin, hyaluronic acid, and the like), nucleic acids (such, as for example, RNAs, DNAs, and the like), negatively-charged proteins, and the like, and any combination thereof), and the like, and any combination thereof.

Statement 6. A LipCo according to any one of Statements 3-5, where the mass ratio of cationic component(s) to anionic component(s) is about 4 to about 1, including all 0.1 mass ratio values and ranges therebetween.

Statement 7. A LipCo according to any one of the preceding Statements, where the lipid(s) is/are chosen from fats, oils, waxes, vitamins (such as, for example, vitamin A, vitamin D, vitamin E, vitamin K, and the like), hormones, phospholipids (Phosphatidylglycerol (PG) including 18:0 PG, 17:0 PG, 16:0 PG, 18:2 PG, 20:4 PG, etc., Phosphatidylserine (PS) including DOPS, 18:2 PS, 22:6 PS, 18:0 PS, 17:0 PS, etc., Phosphatidic acid (PA) including 18:0 PA, 18:1 PA, 18:2 PA, 17:0 PA, 16:0 PA, etc.), glycerolipids, glycerophospholipids (Phosphatidylethanolamine (PE) including 18:0 PE, 17:0 PE, 10:0 PE, 16:1 PE, 18:2 PE etc. phosphatidylcholine (PC) including DHPC, DLPC, DPPC DMPC, DSPC, DOPC etc.), sphingolipids (such as, for example, sphingomyelin, ceramides, and the like), sterols (such as, for example, cholesterol, or the like), and the like, and any combination thereof.

Statement 8. A LipCo according to Statement 7, where in the lipid(s) comprise(s) dioleoylphosphatidylcholine (DOPC), 1,2-Distearoyl-sn-glycero-3-phospho-rac-glycerol (DSPG), dipalmitoylphosphatidylcholine (DPPC), or the like, or a salt thereof, or any combination thereof.

Statement 9. A LipCo according to any one of the preceding Statements, where the LipCo further comprises one or more biomolecule(s) or the like.

Statement 10. A LipCo according to Statement 9, where the biomolecule(s) is/are independently chosen from proteins and the like.

Statement 11. A LipCo according to any one of the preceding Statements, where the LipCo comprises or exhibits a longest linear dimension (such as, for example, a diameter or the like) of about 100 nanometers (nm) to about 20 micrometers (microns), including all 0.1 nanometer values and ranges therebetween.

Statement 12. A LipCo according to any one of the preceding Statements, where the LipCo comprises or exhibits a zeta potential of from about-4 millivolts (mV) to about +0.5 mV, including all 0.1 mV values and ranges therebetween.

Statement 13. A LipCo according to any one of the preceding Statements, where the LipCo is stable.

Statement 14. A composition comprising a plurality of LipCos of the present disclosure (such as, for example, LipCo(s) according to any one of the preceding Statements).

Statement 15. A composition according to Statement 14, where the LipCos comprise or exhibit an average longest linear dimension (such as, for example, an average diameter or the like) of about 100 nm to about 20 microns, including all 0.1 nm values and ranges therebetween.

Statement 16. A composition according to Statement 14 or 15, where the LipCos comprise or exhibit an average zeta potential of about-4 mV to about +4 mV, including all 0.1 mV values and ranges therebetween.

Statement 17. A composition according to any one of Statements 14-16, where the composition comprises one or more pharmaceutical excipient(s) or the like.

Statement 18. A composition according to any one of Statements 14-17, where the composition is stable.

Statement 19. A method of making lipocoacervates (LipCos) (or a LipCo composition) comprising: providing a coacervate composition (e.g., a coacervate solution or the like); and contacting the coacervate composition with a lipid composition, where the LipCos is (or the LipCo composition are) formed.

Statement 20. A method according to Statement 19, where the coacervate is formed by forming an aqueous solution of one or more hydrophobic material(s) or the like.

Statement 21. A method according to Statement 19, where the coacervate is formed by forming an aqueous solution of one or more cationic component(s) and one or more anionic component(s).

Statement 22. A method according to Statement 21, where the mass ratio of cationic component(s) to anionic component(s) is about 4 to about 1, including all 0.1 mass ratio values and ranges therebetween.

Statement 23. A method according to any one of Statements 19-22, where the lipid(s) is/are chosen from fats, oils, waxes, vitamins (such as, for example, vitamin A, vitamin D, vitamin E, vitamin K, and the like), hormones, phospholipids (Phosphatidylglycerol (PG) including 18:0 PG, 17:0 PG, 16:0 PG, 18:2 PG, 20:4 PG, etc., Phosphatidylserine (PS) including DOPS, 18:2 PS, 22:6 PS, 18:0 PS, 17:0 PS etc., Phosphatidic acid (PA) including 18:0 PA, 18:1 PA, 18:2 PA, 17:0 PA, 16:0 PA, etc.), glycerolipids, glycerophospholipids (Phosphatidylethanolamine (PE) including 18:0 PE, 17:0 PE, 10:0 PE, 16:1 PE, 18:2 PE etc. phosphatidylcholine (PC) including DHPC, DLPC, DPPC DMPC, DSPC, DOPC etc.), sphingolipids (such as, for example, sphingomyelin, ceramides, and the like), sterols (such as, for example, cholesterol, or the like), and the like, and any combination thereof.

Statement 24. A method according to any one of Statements 19-22, the method further comprises isolating the LipCo(s).

Statement 25. A method of biomolecule delivery comprising: contacting a population of cells, an individual, or the like, with one or more LipCo(s) and/or one or more composition(s), each composition comprising a plurality of LipCos (e.g., as disclosed herein, such as, for example, LipCo(s) according to any one of Statements 1-13, composition(s) according to any one of Statements 14-18, prepared by a method according to any one of Statements 19-24, or any combination thereof), where at least a portion or all of the LipCos independently comprise one or more biomolecule(s), where at least a portion of or all of the LipCo(s) (or biomolecule(s) is/are delivered to the population of cells, the individual, or the like.

Statement 26. A method according to Statement 25, where the contacting comprises administration of the plurality of LipCos to an individual.

Statement 27. A method according to Statement 25 or 26, where the LipCo(s) is/are taken up by a cell or cells of the population of cells or the individual, and LipCo(s) is/are is released within the cell or cells.

Statement 28. A method according to any one of Statements 25-27, where at least a portion or all of the LipCos comprises one or more biomolecule(s) and the biomolecule(s) retain/retains (e.g., after delivery) substantially all (or all) structural features and/or 50% or more, 70% or more, 90% or more, or 95% or more biological activity compared with the native protein or the protein delivered without use of a LipCo(s).

Statement 29. A method according to any one of Statements 25-27, where the individual is diagnosed with and/or is in need of treatment for a disease, disease state, or the like, and the disease, the disease state, or the like is treatable, preventable, or the like, by the biomolecule(s).

The steps of the method described in the various examples disclosed herein are sufficient to carry out the methods of the present disclosure. Thus, in various examples, a method consists essentially of a combination of the steps of the methods disclosed herein. In various other examples, a method consists of such steps.

The following examples are presented to illustrate the present disclosure. They are not intended to be limiting in any manner.

Example 1

This example describes lipocoacervates of the present disclosure, and methods of making and using same.

Described is a method to prepare coacervate with enhanced stability. Phospholipids were assembled on the surface of a coacervate to form lipocoacervate (LipCo). The resultant LipCo possessed a discrete spherical structure with a coacervate interior and phospholipid outer shell. The size of LipCo did not change over the four-week observation window, whereas coacervate coalesced into one bulk phase within 30 minutes. Vascular endothelial growth factor-C (VEGF-C) and fibroblast growth factor-2 (FGF-2) were used as examples to test LipCo's ability to maintain protein bioactivity. The in vitro lymphangiogenesis assay demonstrated that human dermal lymphatic endothelial cells (LECs) formed an increased network of cord in VEGF-C and FGF-2 loaded LipCo group compared to free proteins and proteins loaded in coacervate. Overall, LipCo could serve as a protein delivery vehicle with improved colloidal stability.

One strategy to overcome these hurdles is to enclose a coacervate with a phospholipid membrane as a way to increase the colloidal stability of complex coacervates. By adjusting the ratio between the polycation and polyanion in coacervate, it is easy to control the overall charge of coacervate. The charge in turn can be used to increase affinity with charged phospholipid. Zhang et al. showed that polar and charge interaction between phospholipid and coacervate anchored the 1,2-dipalmitoyl-sn-glycero-3-phosphocholine (DPPC) membrane to the encapsulated diethylaminoethyl dextran/dsDNA coacervate. The resultant giant coacervate vesicles possessed increased permeability compared to naked coacervate or empty giant unilamellar vesicles. Liu et al. reported that via complexing the negatively charged erythrocyte membrane with positively charged diethylaminoethyl dextran/dsDNA coacervate, the formed erythrocyte-membrane-encapsulated coacervate protocells demonstrate prolonged blood circulation time and improved hemocompatibility in rabbits. Taken together, the lipid membrane assembled at the surface of the coacervate stabilizes the coacervate and provides a protective barrier for the coacervate from the surrounding environment.

A 1,2-dioleoyl-sn-glycero-3-phosphocholine (DOPC)/1,2-distearoyl-sn-glycero-3-phospho-(1'-rac-glycerol) (DSPG)/cholesterol lipid membrane enclosed-PEAD/heparin coacervate as a protein delivery vehicle is described. By complexing a negatively charged lipid mixture with a slightly positively charged PEAD/heparin coacervate, lipids assemble at the surface of the coacervate. The surface charge and size of LipCo, growth factor loading efficiency and release, and network formation of LECs were investigated in order to understand the potential of LipCo as a protein delivery vehicle. Data indicate that LipCo possesses improved colloidal stability and the capability to deliver growth factors.

Materials and Methods. Materials. PEAD was synthesized as previously described. Clinical-grade sodium heparin was a gift from Scientific Protein Labs. Fluorescein conjugated bovine serum albumin (FITC-BSA) was purchased from Sigma-Aldrich. Bovine serum albumin was purchased from VWR Chemicals. Recombinant human FGF-2, recombinant human VEGF-C, human FGF-2 DuoSet ELISA kit, human VEGF-C DuoSet ELISA kit, and DuoSet ELISA Ancillary Reagent Kit 2 were purchased from R&D Systems. EGM-2 MV BulleKit was purchased from Lonza. DOPC, DSPG, 1,2-dioleoyl-sn-glycero-3-phosphoethanolamine-N-(lissamine rhodamine B sulfonyl) (Liss Rhod PE), and cholesterol were purchased from Avanti Polar Lipids. 0.9% normal saline was purchased from Growcells. Tissue culture treated 24 wells cell culture plate was purchased from Corning. Human dermal lymphatic endothelial cells were kindly provided by Professor Esak Lee at Cornell University, Ithaca New York, originally obtained and characterized by Dr. Young K. Hong from Keck School of Medicine, University of South California, Los Angeles, California. Rabbit anti-human LYVE-1 antibody was purchased from Abcam. Mouse anti-human VE-cadherin antibody was purchased from Santa Cruz Biotechnology. Molecular Probe Alexa Fluor-488 Phalloidin and DAPI were purchased from Thermo Fisher Scientific. Secondary antibodies were purchased from Invitrogen.

Preparation of LipCo. 10 mg/ml each of PEAD and heparin solutions were prepared in 0.9% normal saline. Various mass ratios between PEAD and heparin (P/H ratios) were used to form coacervate. Typically, 40 μl of heparin solution was mixed with 160 μl of PEAD solution to form positively charged coacervates. After 5 minutes of static coacervation, 10 μl of DOPC/DSPG/cholesterol (molar ratio=5:1:4) and 2 μl of rhodamine-PE ethanol solution were added into coacervate suspension to achieve final weight ratio of 5% (lipid: coacervate, w/w). After 1 hour of gentle shaking on an orbital sharker at 50 rpm, LipCo suspension was obtained. To remove the excessive ethanol, LipCo suspension was centrifuged at 300×g for 5 minutes. The resultant supernatant was discarded, and the LipCo pellets were resuspended in 0.9% normal saline. As for FITC-BSA loaded LipCo, 4 μl of FITC-BSA stock solution (10 mg/ml) was complexed with 40 μl of heparin solution for 5 minutes prior to adding 160 μl of PEAD solution, and all other procedures were as described above.

Confocal Microscopy. Confocal microscopy images were obtained using a Leica SP8 confocal microscope with a 60× objective.

Size and size distribution measurement. LipCos with various P/H ratios was prepared as described above. Microscopic images were obtained using a Nikon ECLIPSE Ti2 microscope with a 10× objective. For each sample, 5 random images were taken, and LipCo size was quantified using Image J.

Zeta potential measurement. Coacervate and LipCo were prepared as described above. 1 ml of each sample suspension was transferred to a polystyrene cuvette for zeta potential measurement (Malvern Zetasizer Nano ZS90). The measurement was repeated three times for each sample.

Resistance against coalescence. The stability of LipCo was examined by monitoring the LipCo size over time. After initial formation, LipCo suspension was stored at 4° C. Samples were imaged every week using a Nikon ECLIPSE Ti2 microscope with a 10× objective. For each sample, 5 random images were obtained, and LipCo size was quantified using image J. To access the effect of lipid on preventing vesicle aggregation and coalescence, coacervate and LipCo were centrifuged at 300×g for 5 minutes, and supernatant was discarded. The pellets were then resuspended with 0.9% normal saline and imaged.

Growth factors loading and in vitro release. FGF-2 and VEGF-C loaded coacervate and LipCo were prepared as described above. Each sample contained 500 ng of FGF-2 and 500 ng of VEGF-C. 1% bovine serum albumin in 0.9% normal saline was used as release buffer solution. After initial formation, protein loaded coacervate and LipCo were immediately centrifuged at 12100×g for 10 minutes, and the supernatant was collected and analyzed via ELISA to indirectly access growth factor loading efficiency. Coacervate and LipCo pellets were gently resuspended with release buffer solution and incubated at 37° C. for subsequent time points. For each time point, samples were spun down and supernatants were collected and stored at −20° C. until analysis via ELISA.

LEC network formation. Human dermal lymphatic endothelial cells were kindly provided by Professor Esak Lee at Cornell University, Ithaca New York, originally obtained and characterized by Dr. Young K. Hong from Keck School of Medicine, University of South California, Los Angeles, California. Briefly, LECs were seeded in 24 wells plate with cell density of 50,000 cells/well. Four different groups were tested: EBM-2 basal medium with 0.5% FBS, free VEGF-C (400 ng) and FGF-2 (200 ng), VEGF-C (400 ng) and FGF-2 (200 ng) loaded coacervate and LipCo. Tissue culture inserts (pore size: 3 μm, Greiner Bio-One) were used to separate coacervate and LipCo from cells for better observation. After 24 hours of incubation, cells were fixed and stained with primary and secondary antibodies to visualize any network that formed. The images were analyzed via NIH Image J plugin Angiogenesis Analyzer. Five different images were acquired in each group to quantify the number of cords, total branch number, and total cord length.

Immunocytochemistry. Cells were fixed with 4% (w/v) paraformaldehyde in EBM-2 basal medium at room temperature for 20 minutes and subsequently washed in PBS, followed by permeation with 3% (v/v) Triton X 100 in PBS at room temperature for 20 minutes and subsequently washed in PBS, and then blocked by 3% (w/v) BSA in PBS at room temperature for 45 minutes. Primary antibody was then diluted with 3% (w/v) BSA in PBS and incubated with cells overnight at 4° C. Cells were then washed with PBS, followed by incubating with secondary antibody diluted in 3% (w/v) BSA in PBS at room temperature in the dark for 20 minutes and washed in PBS. DAPI and phalloidin counterstaining was performed and washed in PBS. The antibody dilution factors were: primary anti-LYVE-1 antibody, 1:120; primary anti-VE-cadherin antibody, 1:100; secondary goat anti-rabbit Alexa Fluor 594 antibody, 1:1000; secondary goat anti-mouse Alexa Fluor 594 antibody, 1:400. DAPI counterstaining, 1:500. Phalloidin counterstaining, 1:200. Immunofluorescence images were captured on a Nikon ECLIPSE Ti2 microscope.

Statistics. Data are presented as mean±standard deviation (S.D.). The statistical significance was determined by Student's/test.

Results. Preparation and characterization of LipCo. LipCo were formed in two steps: coacervation of PEAD and heparin and lipid assembly on the coacervate. Various PEAD to heparin (P/H) mass ratios were used to prepare coacervate, resulting in slightly negatively charged coacervate (−1.25 mV, P/H=3.6) to positively charged coacervate (+14.6 mV, P/H=7) (FIG. 1A). DOPC/DSPG/cholesterol ethanol solution was then added to the freshly prepared coacervate solution to form LipCo. The electrostatically mediated adsorption of the negative DOPC/DSPG/cholesterol on the coacervate surface reduced the surface charge to approximately-0.74 m V with P/H=4. (FIG. 1A). The average size of LipCo was 3.46±1.78 μm in diameter, and the size distribution indicated that most of the formed LipCo ranged from 2 to 6 μm in diameter. (FIG. 1B). Confocal microscopy images showed that LipCo were discrete spherical vesicles with a bright red fluorescent outer shell (Liss Rhod PE) and a green fluorescence interior (FITC-BSA) (FIG. 1C-D).

Figure 2:
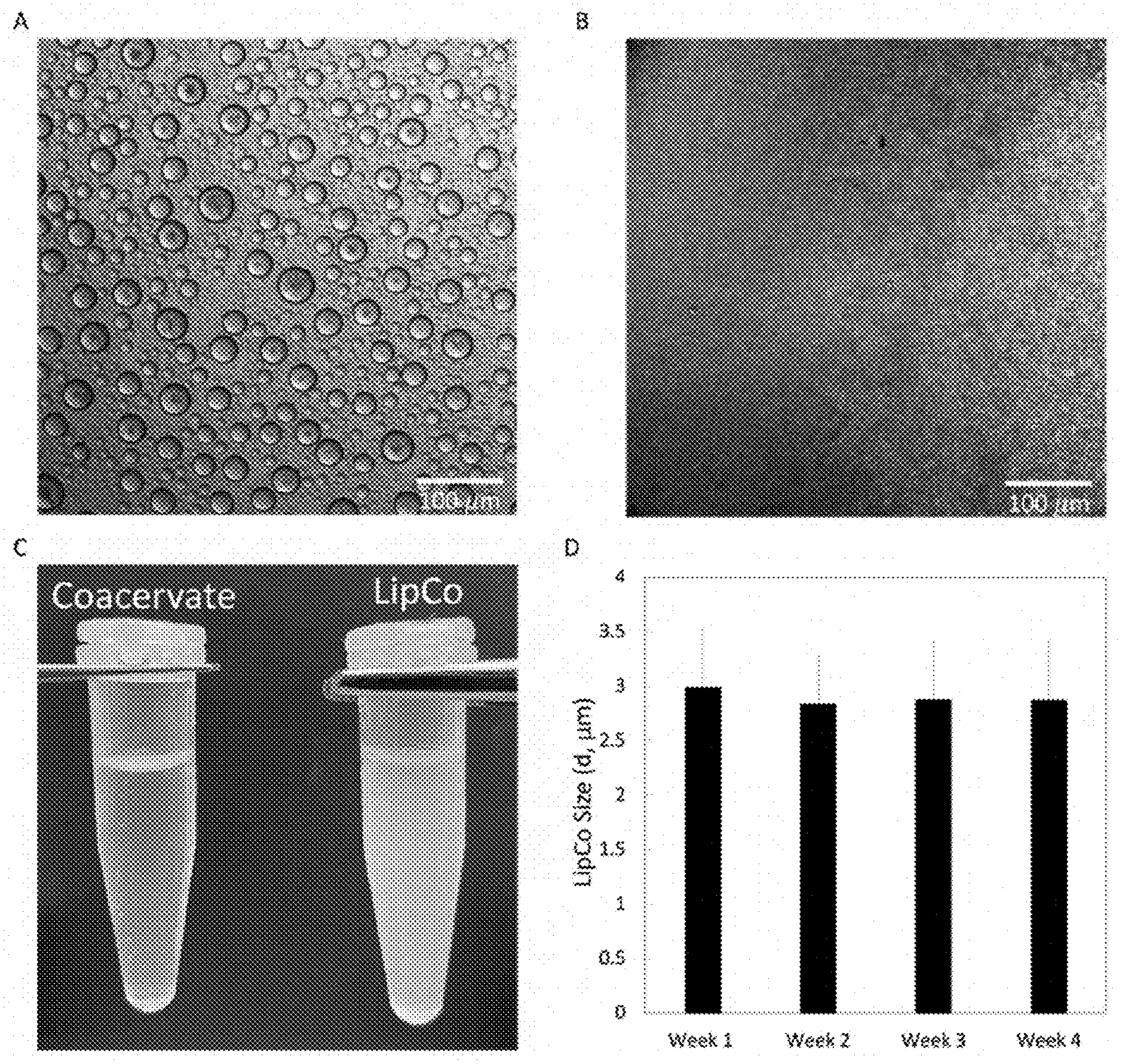
FIG. 2 shows colloidal stability of PEAD/heparin coacervate and LipCo at different times. A,B—Bright-field microscopic image of PEAD/heparin coacervate and LipCo, 15 minutes after initial formation. Scale bar: 100 μm. C-Resuspension of centrifuged coacervate and LipCo. D—Diameter of LipCo stored over 4 weeks in 4° C. Data are presented as mean±standard deviation (n=3). The difference in size is not statistically significant.

Lipid assembly enhanced coacervate colloidal stability. The lipid membrane on the surface of LipCo prevented coacervate to coalesce. 15 minutes post preparation, coacervate formed large spheres (FIG. 2A) compared to LipCo, which remained as small individual vesicles (FIG. 2B). The coalesced coacervate could not be resuspended and formed a viscous bulk liquid phase at the bottom of the tube (FIG. 2C, left). Compared to coacervate, LipCo could be easily resuspended and dispersed well (FIG. 2C, right). The vesicle size over time was further examined. Because the coacervate tended to aggregate immediately after the initial formation and coalesce, he experiments to determine their size over time could not be performed. The size of LipCo did not have statistically significant change over 4 weeks with an average diameter of 2.90±0.5 μm (FIG. 2F). Overall, the colloidal stability of LipCo was much higher than that of the coacervate.

Figure 3:
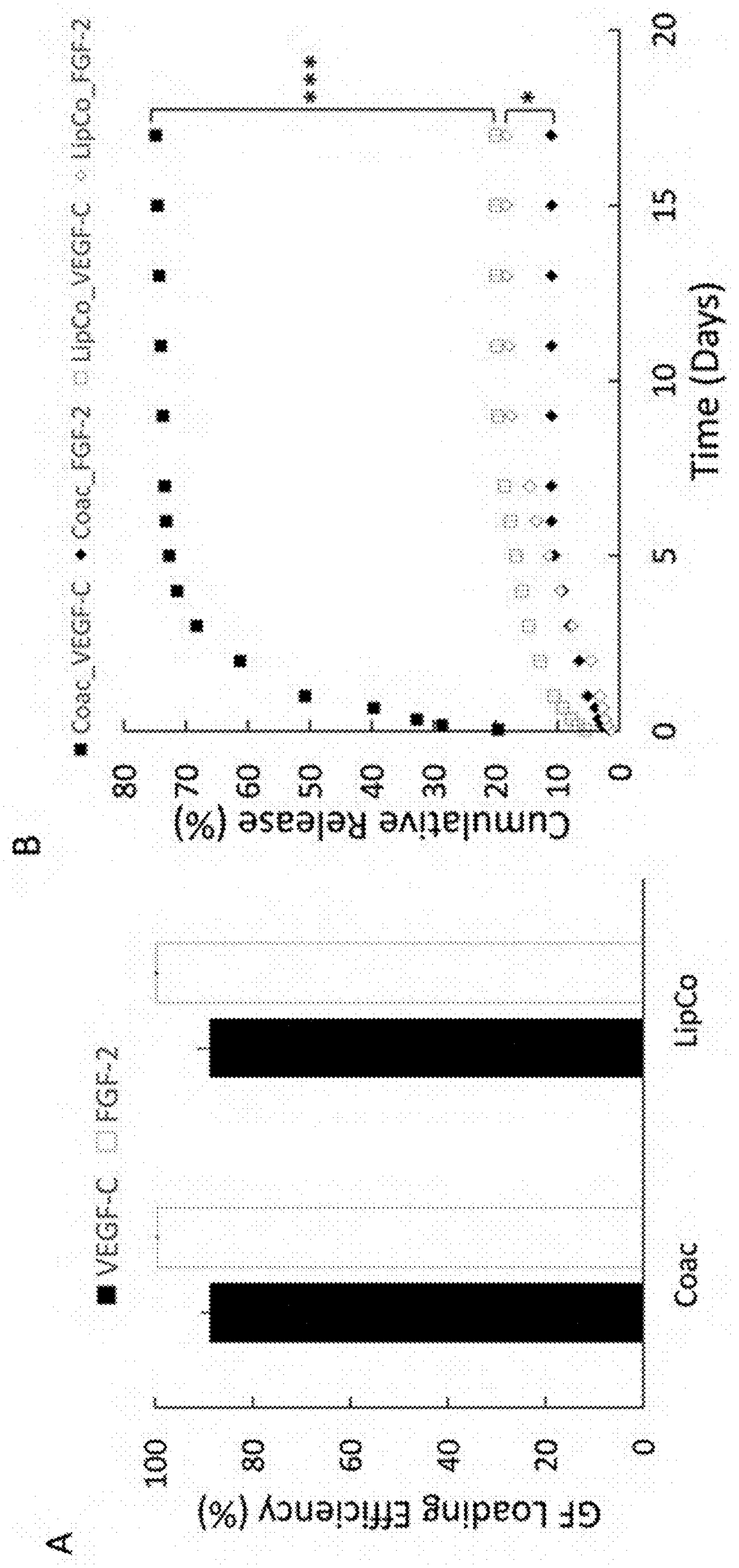
FIG. 3 shows loading efficiency and release profiles of growth factors. A-Loading efficiency of VEGF-C and FGF-2 in coacervate and LipCo. Data are presented as mean±standard deviation (n=3). The VEGF-C and FGF-2 loading efficiency in coacervate and LipCo are not statistically significant. B—In vitro cumulative release of VEGF-C (square) and FGF-2 (diamond) from coacervate and LipCo in 0.9% saline with 1% BSA. Data are presented as mean±standard deviation (n=3), *: $p<0.05$, and ***: $p<0.001$.
Figure 4:
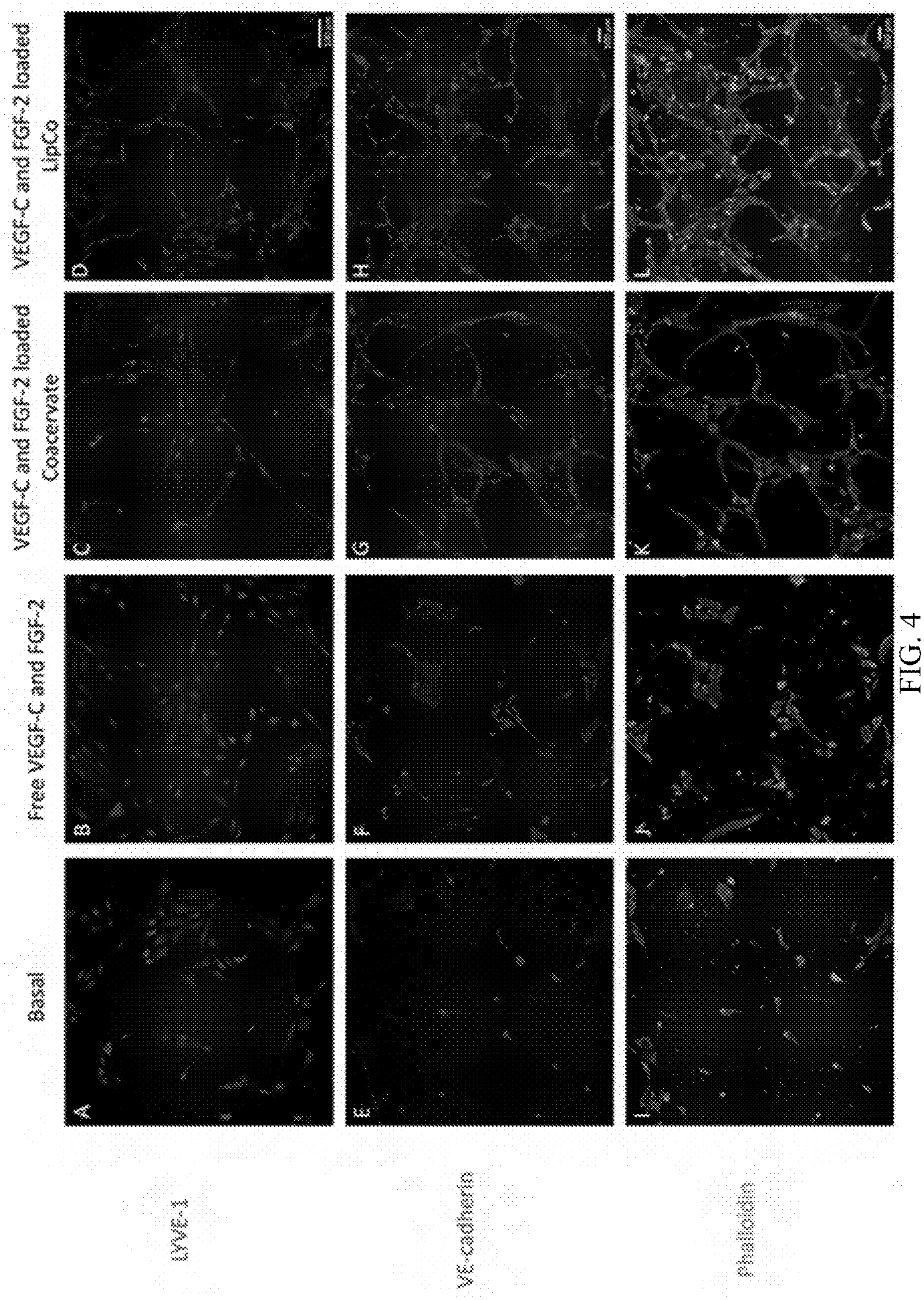
FIG. 4 shows VEGF-C and FGF-2 induced network formation on LECs. LYVE-1 staining (red) on LECs with A—basal medium+5% FBS, B—free VEGF-C and FGF-2, C—VEGF-C and FGF-2 loaded coacervate, and D—VEGF-C and FGF-2 loaded LipCo. Scale bar: 100 μm. VE-cadherin staining (red) on LECs with E—basal medium+5% FBS, F-free VEGF-C and FGF-2, G—VEGF-C and FGF-2 loaded coacervate, and H—VEGF-C and FGF-2 loaded LipCo. Scale bar: 100 μm. Phalloidin (green) staining on LECs with I—basal medium+5% FBS, J—free VEGF-C and FGF-2, K-VEGF-C and FGF-2 loaded coacervate, and L—VEGF-C and FGF-2 loaded LipCo. Scale bar: 100 μm.

Loading and controlled release of growth factors. The growth factors (GFs) loading efficiency and release capability were tested by loading both VEGF-C and FGF-2 into coacervate or LipCo. The loading efficiency was 89% for VEGF-C and 99% for FGF-2 (FIG. 3A). For coacervate, approximately 35% of loaded VEGF-C and less than 10% of loaded FGF-2 were released at day 1 (FIG. 3B). It has been shown that FGF-2 has high binding affinity to heparin, resulting in sustained release rate in heparin-based protein delivery system. By one week, 79% of VEGF-C and 10% of FGF-2 were released. Thus, coacervate yielded faster release of VEGF-C and retained FGF-2 longer. Interestingly, a delayed release of VEGF-C in LipCo (FIG. 3B) was observed. By day 1, less than 10% of loaded VEGF-C was released, which was significantly lower than coacervate. This difference was attributed to the lipid membrane acting as an additional barrier to slow down the release. Furthermore, the release of FGF-2 in LipCo after one week was higher than coacervate (p=0.032). The faster release of FGF-2 in LipCo could be a result of competition. Compared to coacervate, the released and free VEGF-C would remain in the interior of LipCo, which competes with FGF-2 to bind heparin, thereby accelerating the release of FGF-2. In short, LipCo was able to release the loaded GFs in a controlled manner.

Figure 5:
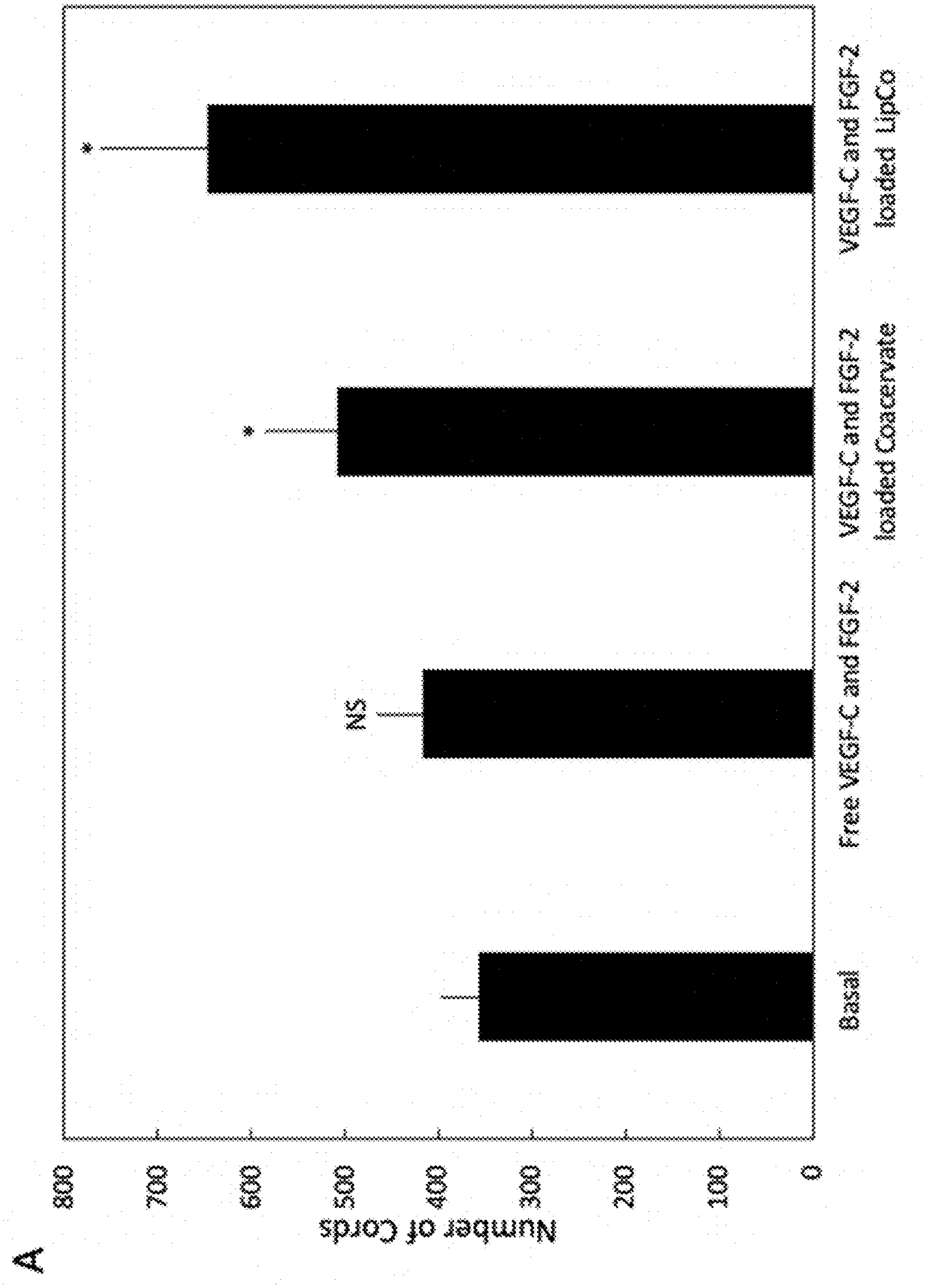
FIG. 5 shows Statistical measurement of A—number of cords, B—number of branch points, and C—total cord length. Data are presented as mean±standard deviation (n=5). NS: non-significant, *: $p<0.05$, : $p<0.01$, and *: $p<0.001$.
Figure 5:
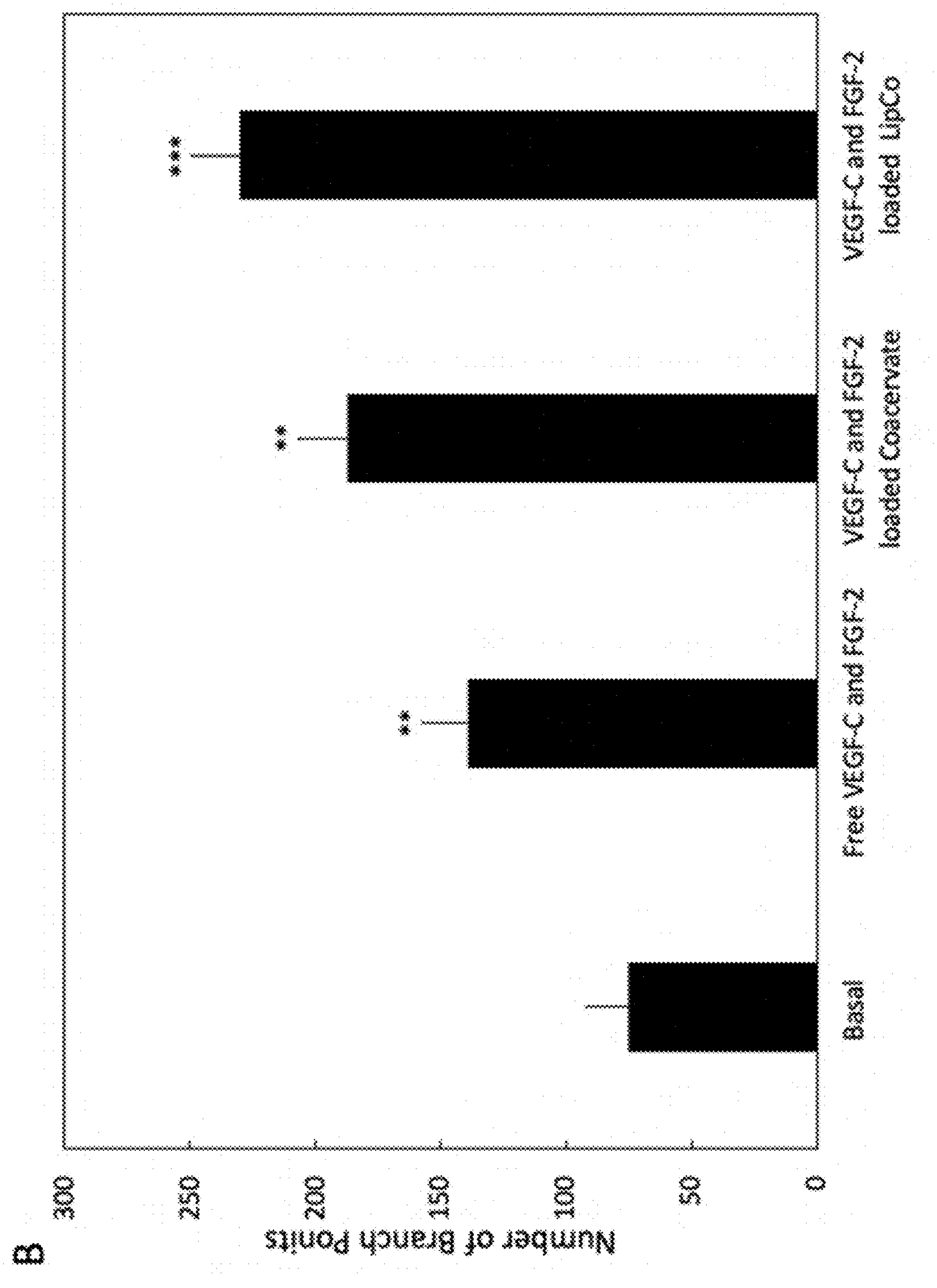
Figure 5:
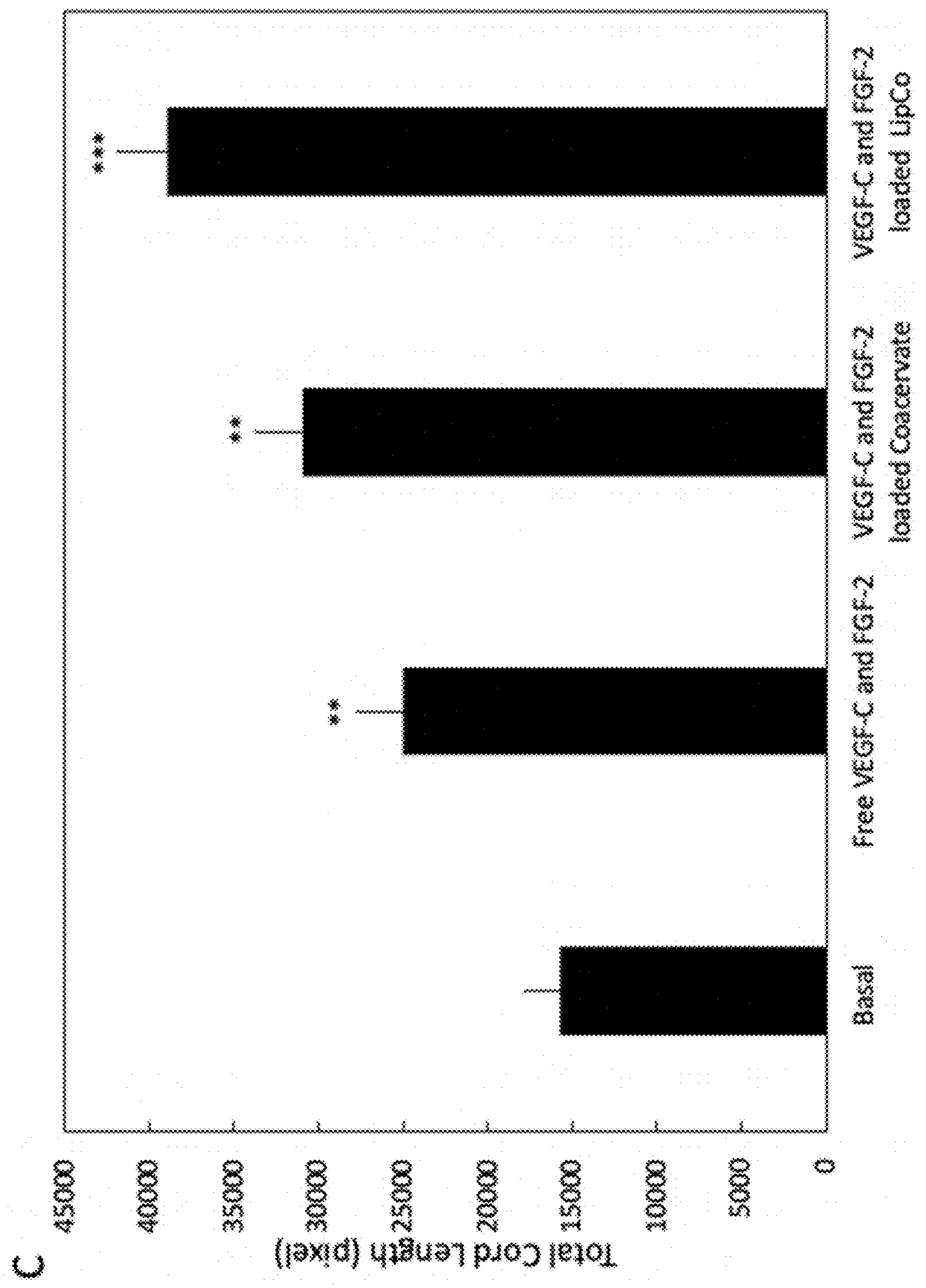

VEGF-C and FGF-2 loaded LipCo stimulated LECs to form extensive networks. To examine the bioactivities of the growth factors released from LipCo, two lymphangiogenic factors, VEGF-C and FGF-2 were chosen as the target proteins. It has been reported that VEGF-C and FGF-2 have additive effects on lymphangiogenesis. VEGF-C and FGF-2 were loaded into LipCo and induced network formation on LECs. LYVE-1 staining showed that VEGF-C and FGF-2 induced lymphangiogenic response (FIG. 4A-D). VE-cadherin (FIG. 4E-H) and phalloidin staining (FIG. 4I-L) outlined the formed network. Compared to other groups, GFs loaded LipCo stimulated LECs to form extensive cord structures and networks after 24 hours (FIGS. 4H and 4L) with highest number of cords, branch points, and total cord length (FIG. 5A-C). In the GFs loaded coacervate group (FIGS. 4G and 4K), a smaller area was covered via LECs compared to the GFs loaded LipCo group. Free GFs group (FIGS. 4F and 4J) was also able to form cords but to a lesser extent than GFs loaded coacervate and LipCo due to the short half-life time. Taken together, VEGF-C and FGF-2 loaded LipCo robustly stimulated network formation on LECs.

Discussion With the incorporation of lipid membrane on the surface of PEAD/heparin complex coacervate, LipCo as a protein delivery vehicle for systemic administration was demonstrated.

To prepare LipCo, lipid membrane formed by DOPC/DSPG/cholesterol on the coacervate surface is used in this study. DOPC is the most abundant phospholipid in biological membranes with high fluidity at body temperature. Therefore, DOPC was chosen as the main component of the lipid membrane. Protein released from LipCo with saturated lipid such as DPPC in the membrane may be impeded due to the increased rigidity. Cholesterol is present at up to 40 mol % in eukaryotic plasma membranes to increase the order of lipid packing and stabilize membrane against structural damage. Thus, 40 mol % of cholesterol was used to stabilize the lipid membrane in LipCo. The main driving force of LipCo formation is the electrostatically mediated adsorption of the negative DOPC/DSPG/cholesterol on the slightly positive coacervate surface. Unsaturated anionic lipid such as 1,2-dioleoyl-sn-glycero-3-phospho-(1'-rac-glycerol) (DOPG) is avoided because it causes too much instability of the lipid membrane. Also, it was found that 10 mol % of DSPG in the lipid formulation can effectively alter the surface charge to approximately-0.74 mV after lipid assembly on the coacervate surface. The slightly negatively charged surface provided repulsive force between each LipCo, further preventing LipCo coalescence. Overall, this lipid formulation improved the colloidal stability of the coacervate.

Self-assembly process readily makes lipid membrane enclosed PEAD/heparin complex coacervate. The size of LipCo stays the same over a four-week observation window at 4° C., demonstrating the potential for long term storage. To the best of our knowledge, the present study is the first to report long term stability of coacervate-filled lipid vesicles. The growth factors released from LipCo are bioactive and are more potent at inducing lymphangiogenic response than free proteins or protein coacervate. Lipid vesicles enclosing PEAD/heparin complex coacervate provides a foundation for a stable coacervate formulation. Future studies on pharmacokinetics and biodistribution of LipCo are warranted to assess its therapeutic potential for protein delivery.

Example 2

This example describes lipocoacervates of the present disclosure, and methods of making and using same.

Described is a self-assembling, tunable vesicle for the controlled delivery of growth factors and cytokines. Coacervate made of heparin and a biocompatible polycation, PEAD, forms the core of the vesicle; lipids form the membrane of the vesicle. This vesicle was termed lipocoacervate (LipCo), which has a high affinity for growth factors and cytokines due to heparin. LipCo has a tunable size, displays the ability to interact with other vesicles post formation, and release active therapeutics. Described are principles of LipCo assembly and its utility for protein therapies.

To leverage the natural and favorable characteristics of PEAD/heparin complex coacervate for protein delivery, a coacervate-filled lipid vesicle, lipocoacervate (LipCo), was developed. The lipid mixtures enclosed PEAD/heparin complex coacervate through self-assembly process. LipCo has shown to be colloidal stable over a four-week observation window at 4° C., compared to naked coacervate that forms an irreversible aggregate. The released FGF-2 and vascular endothelial growth factor-C are bioactive and synergistic at inducing lymphangiogenic response on human lymphatic endothelial cells than free growth factors or coacervate of growth factors. Ongoing studies are in progress to analyze the pharmacokinetics and biodistribution of LipCo to further investigate the therapeutic potential for protein delivery.

As a potential protein delivery platform, LipCo exhibits adaptable properties suitable for a diverse range of applications. In this study, the tunable characteristics of LipCo including size in relation to concentration, salinity, and incubation time post-formation were explored. Additionally, LipCo was prepared with different lipid mixtures, and findings revealed loaded proteins were exchanged between the various LipCos. Moreover, the list of growth factors deliverable by LipCo was expanded to include Granulocyte-macrophage colony-stimulating factor (GMCSF) that stimulates proliferation of TF-1 erythroblasts.

Materials and Methods. Materials. PEAD was synthesized as previously described. Clinical-grade sodium heparin was gifted by Scientific Protein Labs. 1,2-dioleoyl-sn-glycero-3-phosphocholine (DOPC), 1,2-dipalmitoyl-sn-glycerol-3-phosphocholine (DPPC), 1,2-distearoyl-sn-glycero-3-phospho-(1'-rac-glycerol) (sodium salt) (DSPG), and cholesterol were purchased from Avanti Polar Lipids. FITC-Bovine serum albumin (BSA), Texas-Red BSA, and rhodamine-BSA were purchased from Thermo Fisher Scientific. 0.9% normal saline was purchased from Growcells. TF-1 cells were gifted from Noah Johnson at University of Colorado School of Medicine. RPMI-1640 Medium was purchased from American Type Culture Collection, and CCK8 Proliferation Kit from Tocris. All reagents were purchased and used without further purification.

Preparation of LipCo. LipCo was prepared as previously described. Briefly, 10 mg/ml each of PEAD and heparin solutions were prepared in 0.9% normal saline. 40 μl of heparin solution was mixed with 160 μl of PEAD solution to form positively charged coacervates. After 5 minutes of static coacervation, 10 μl of DOPC/DSPG/cholesterol (molar ratio=5:1:4) or DPPC/DSPG/cholesterol (molar ratio=5:1:4) was added into coacervate suspension to achieve final weight ratio of 5% (lipid: coacervate, w/w). After 1 hour of gentle shaking on an orbital sharker at 50 rpm, LipCo suspension was obtained. To remove the excessive ethanol, LipCo suspension was centrifuged at 300×g for 5 minutes. The resultant supernatant was discarded, and the LipCo pellets were resuspended in 0.9%. LipCo was also prepared using 50 mg/ml, 10 mg/ml, 5 mg/ml, 1 mg/ml, and 0.1 mg/ml solutions of PEAD and heparin. Solutions of PEAD and heparin were also prepared with various salt concentrations from 10 mM to 1000 mM at 10 mg/ml.

LipCo size and size distribution measurement. LipCo with various concentration and salt concentration were prepared as described above. 1 ml of each sample suspension was transferred to a polystyrene cuvette for size distribution measurement (Malvern Zetasizer Nano ZS90). The measurement was repeated three times for each sample. Microscopic images were obtained using a Nikon ECLIPSE Ti2 microscope with a 20× objective. Samples were prepared then placed on a glass slide within a 8 mm punch out of silicon to hold liquid.

Preparation of fluorescent proteins loaded LipCo. LipCo was prepared as mentioned above. Briefly, 10 mg/ml each of PEAD and heparin was prepared in 0.9% saline solution. To prepare fluorescent protein loaded LipCo, 80 μl of heparin solution was complexed with either 10 μl of 10 mg/ml Texas Red-bovine serum albumin (BSA) or 10 μl of 10 mg/ml FITC-BSA for 10 minutes. 320 μl of 10 mg/ml PEAD solution was then mixed with each BSA/heparin complex solution for 5 minutes. For the lipid assembly, 20 μl ethanolic solution of DOPC/DSPG/cholesterol (molar ratio: 5/1/4) was mixed with the coacervate suspension. After 1 hour of gentle shaking on an orbital shaker in the dark at 50 rpm, the fluorescent protein loaded LipCo was obtained. To prepare the mixing environment, 25 μl each of Texas Red-BSA loaded LipCo and FITC-BSA loaded LipCo were mixed. The mixed LipCo suspension was either allowed to rest at 37° C. in an incubator or shaken on an orbital shaker at 50 rpm at 37° C. The suspension was then diluted with 450 μl of 0.9% saline solution. The fluorescence images were captured with an inverted Nikon ECLIPSE Ti2 microscope.

Fluorescence Resonance Energy Transfer (FRET). LipCo was prepared as mentioned above. For the FRFT pairs, FITC-BSA and rhodamine-BSA were chosen and separately loaded into LipCo. In addition to DOPC/DSPG/cholesterol lipid solution, DPPC/DSPG/cholesterol lipid mixtures were used to prepare DPPC LipCo. To create mixing environment, 100 μl of FITC-BSA loaded DOPC LipCo was mixed with 100 μl of rhodamine-BSA loaded DOPC LipCo. Similarly, 100 μl of FITC-BSA loaded DPPC LipCo was mixed with 100 μl of rhodamine-BSA loaded DPPC LipCo. The mixed LipCo suspensions were rested at room temperature for 1, 6, 24, 48 and 72 hours. For shorter mixing times, the mixed LipCo suspensions were rested at room temperature for 1, 5, 10, 20, and 30 minutes. At each time point, samples were collected and stored at −20° C. until analysis. To obtain FRET signal, mixed LipCo samples were spun down at 300 g for 5 minutes. The supernatant was discarded to remove the free fluorescent proteins in the solution, and LipCo vesicles were resuspended with 200 μl of 0.9% saline solution. The resultant LipCo suspensions were then excited at 491 nm in a microplate reader, and the emission was measured over a spectrum sweep from wavelength of 520 nm to 600 nm at 10 nm intervals.

FRET analysis. FRET signal was calculated as previously described using the equation: FRET signal=IA (λD)/ID (λD)+Y where Y=ID (λA)/ID(λD). I is the intensity as a function of the wavelength of the acceptor (A) or donor (D). Here, FITC is the donor with emission peak λD=520 nm and rhodamine is the acceptor with excitation peak λA=580 nm. IA, the intensity of the acceptor, is calculated as the intensity of FITC (donor)—the intensity of mixed LipCo (donor and acceptor).

Cell culture. TF-1 cells, an erythroblast cell line, were maintained in ATCC-formulated RPMI-1640 Medium (Catalog No. 30-2001), supplemented with 2 ng/ml of human GM-CSF, 10% fetal bovine serum, and 1% penicillin/streptomycin. Cells were grown in 37° C., 5% carbon dioxide, and 95% humidity.

Bioactivity assay. TF-1 cells were washed with basal RPMI media and seeded at 2000 cells in a total of 100 μL of RPMI media with no GM-CSF in each well of a 96 well plate. Cells were treated after 24 hours with specified GM-CSF concentrations with unloaded/loaded LipCo, coacervate, and native GM-CSF as a positive control. Treatments were prepared at 2× concentrations in 100 microliter RPMI media with no GM-CSF. After 72 hours of incubation, cell proliferation was measured using Cell Counting Kit 8 assay at 460 nm optical density after three hours. Statistical analysis was done using Student's t-Test.

Figure 6:
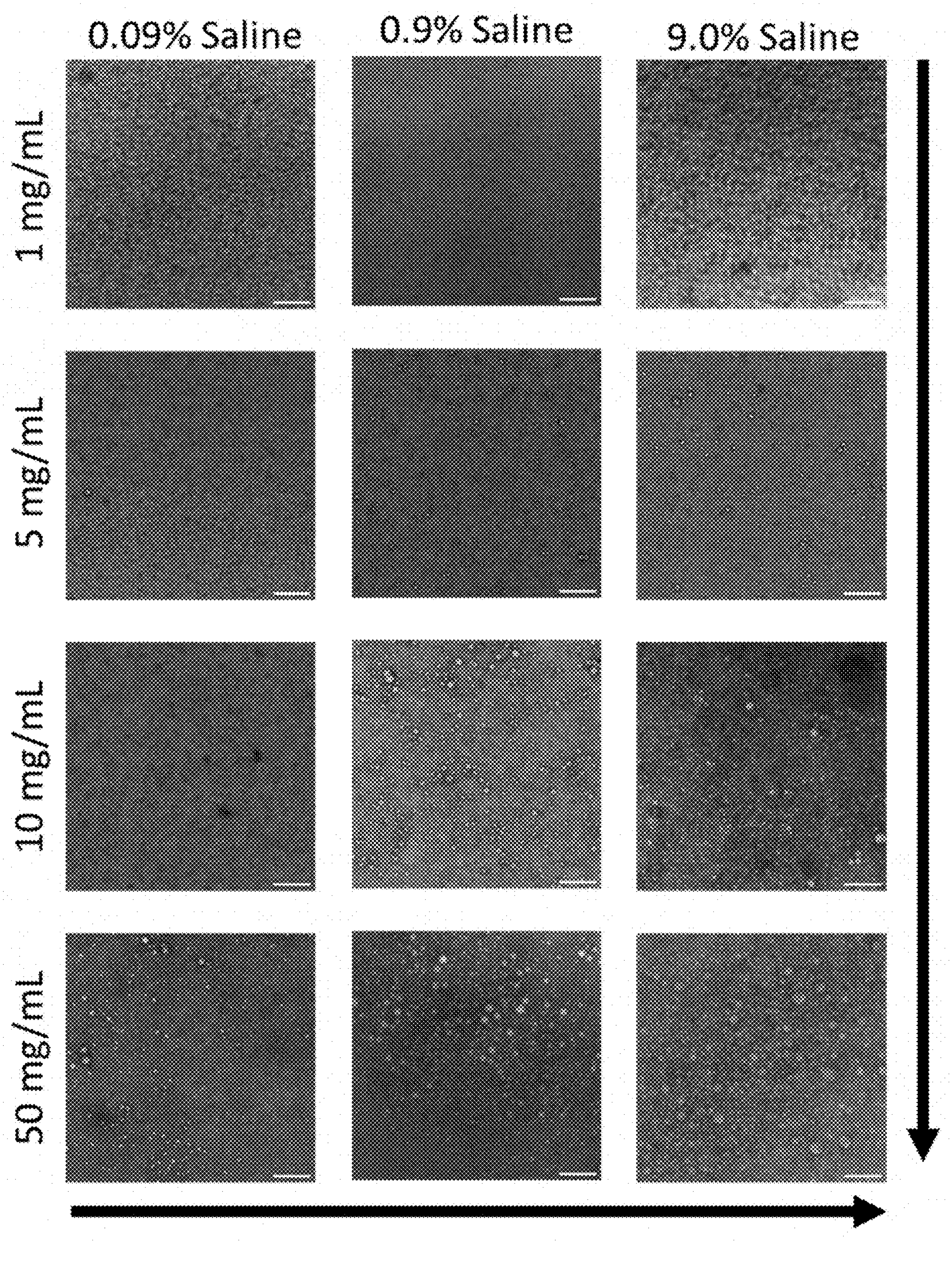
FIG. 6 shows LipCo size is dependent on concentration. As polymer concentration or salinity increases so does the size of LipCo. This allows for adaptation to user needs. Scale bar: 100 μm.

Results. Lipocoacervate size is polymer and salt concentration dependent. The formation of coacervate is driven by the electrostatic charge interactions and the entropically favorable neutralization of the charges. Known factors such as concentration, salinity, and polymer charge have been shown to impact the properties and characteristics of coacervates. As LipCo involves a coacervate core, it was sought to define the size of these vesicles. LipCo size was found to be dependent on concentration, and salinity. As the concentration of LipCo components increases, size also increases (FIG. 6). LipCo size also increases as saline concentration increases from 0.09% to 9.0%.

Figure 7:
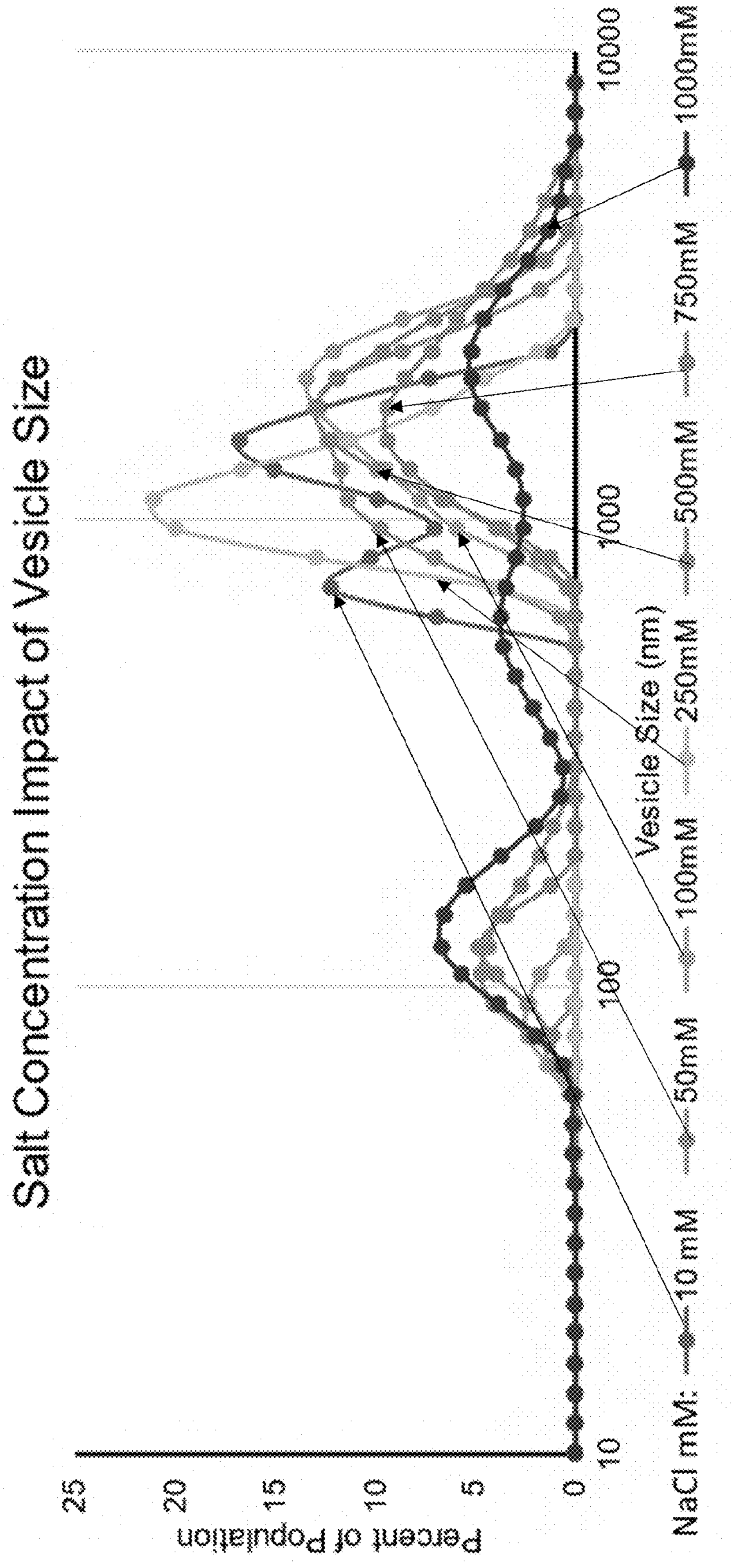
FIG. 7 shows how salt concentration affects the heterogeneity and distribution of the LipCo size. Higher salinity shifts the vesicles to larger sizes as observed with DIC imaging, smaller vesicles are also generated. A possible explanation for the phenomenon of more peaks appearing with higher salinity is that the salt helps to stabilize LipCo vesicle of all sizes, thus results in a larger range of sizes.

The impact of salt concentration was also explored as images suggested a heterogeneous particle populations were generated at high salt concentrations. Using 10 mg/mL polymer solutions, the impact of varying salt concentrations was observed using a Malvern Zetasizer Nano ZS90. This revealed populations that are undetectable in brightfield images with vesicles that are larger than the detection limit of DLS. The heterogeneity of the LipCo sizes increases with salt concentration up to a 1.0 M NaCl solution used in LipCo formation (FIG. 7).

Figure 8:
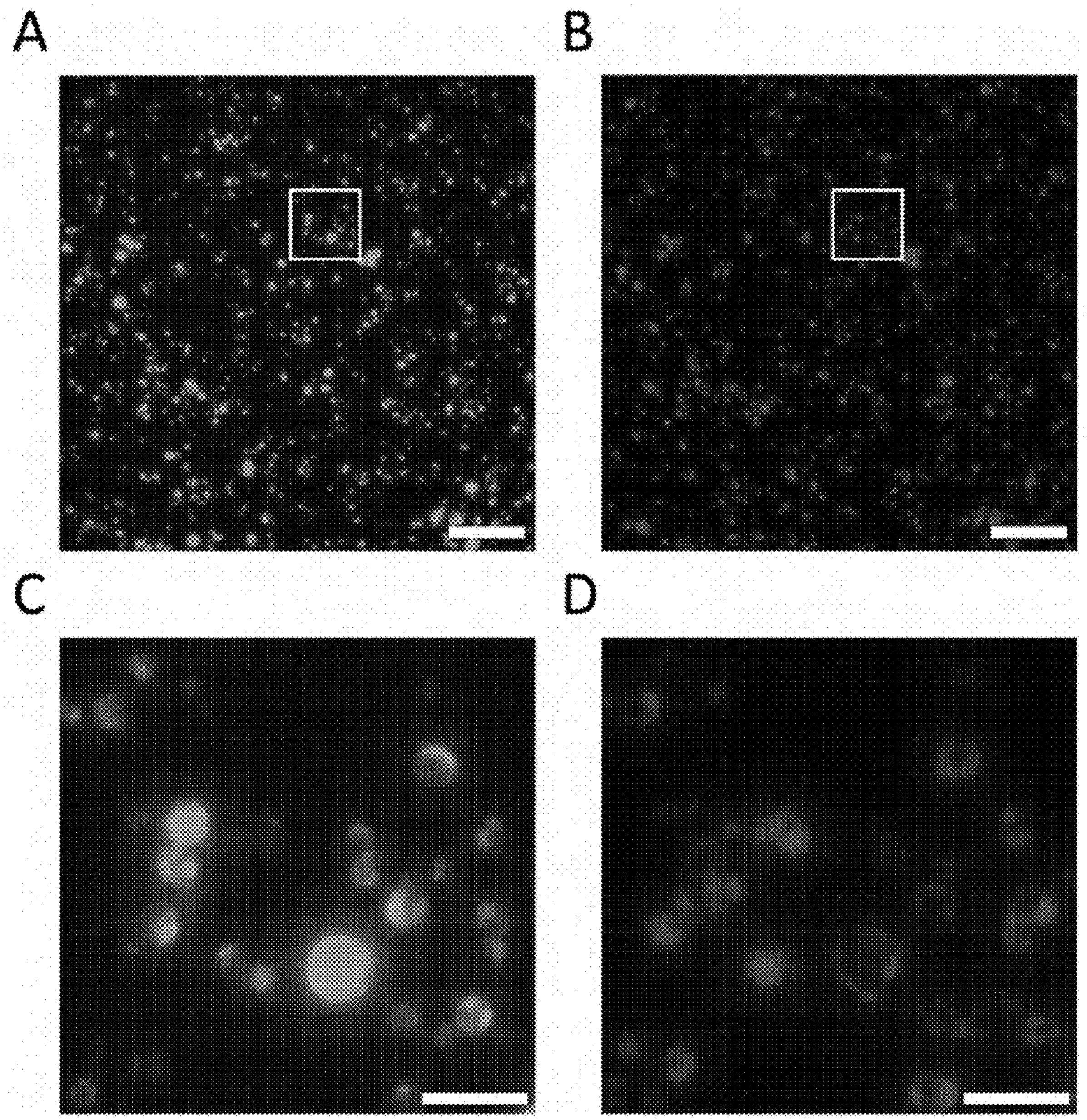
FIG. 8 shows florescent images of mixed DOPC LipCo after 24 h. The same filed of view were observed in green A, C—and red channels B, D—sequentially. A-DOPC LipCo with FITC-BSA and B—DOPC LipCo with Texas Red-BSA. Scale bar=100 μm. White squares: represented area and enlarged in C and D. Scale bar=20 μm.

Diffusion of proteins in LipCo. To examine the material exchange among LipCo vesicles, fluorescent images were obtained on an inverted Nikon ECLIPSE Ti2 microscope. After 24 h (h=hour(s)), LipCo contained both Texas Red-BSA and FITC-BSA were observed (FIG. 8).

The fluorescence resonance energy transfer (FRET) occurs when the donor fluorophores are close enough (typically less than few nanometer) to the acceptor fluorophores for the excitation energy transfer, leading to a change in fluorescence emission. In this study, FITC-BSA and rhodamine-BSA as the FRET pair were selected and loaded the proteins into LipCo separately. Once the fluorescent proteins diffuse out of the original LipCo and pass through the lipid membrane into another LipCo with different fluorescent protein, the fluorescence emission change should be observed.

Figure 9:
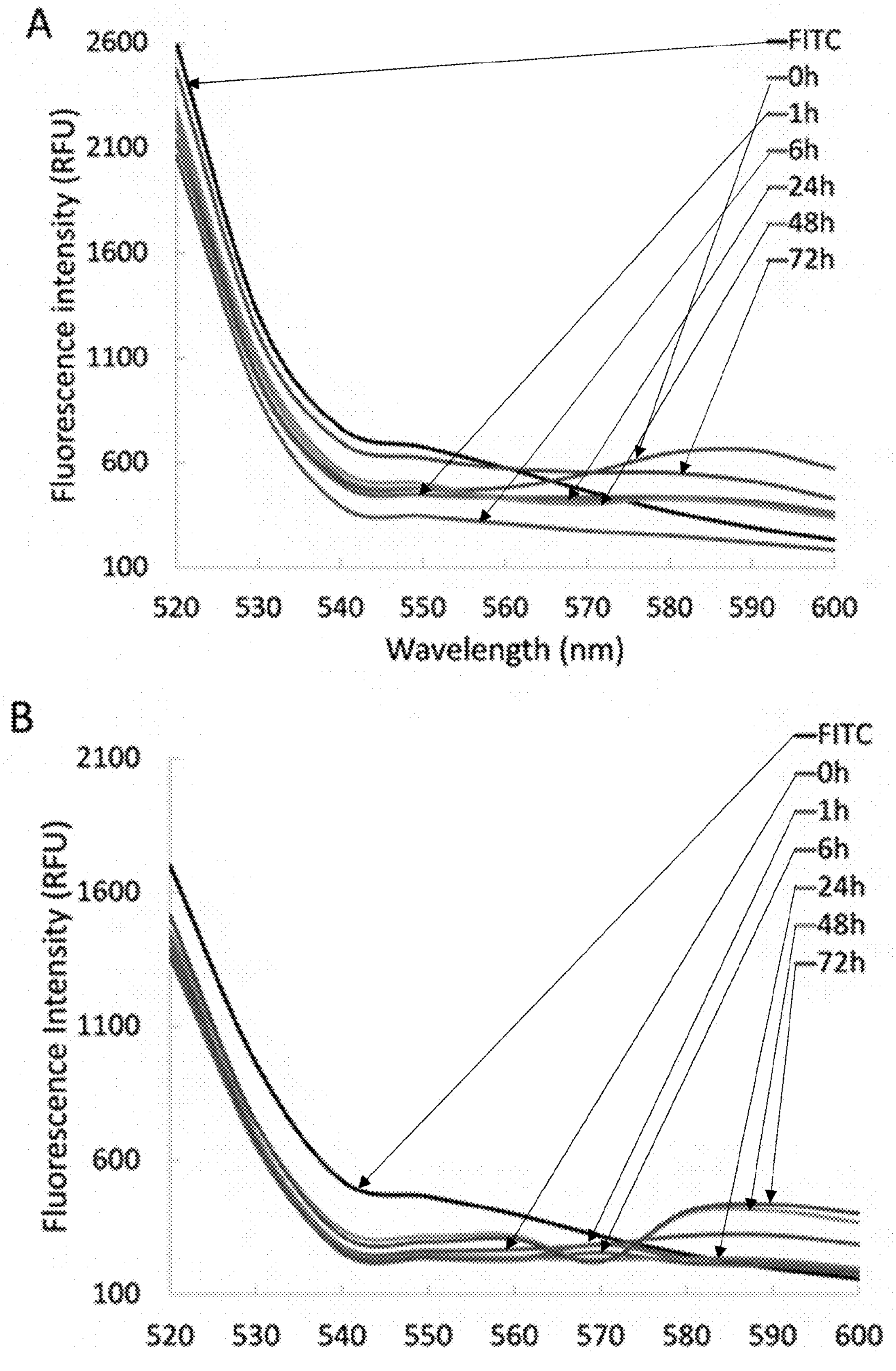
FIG. 9 shows fluorescence emission spectrum and FRET signal analysis from the mixed DOPC LipCo and DPPC LipCo. Changes in the emission spectrum from A—the mixed DOPC LipCo and B—the mixed DPPC LipCo were observed across different mixing times. Excitation wavelength: 491 nm. FITC-only LipCo is represented in black, initial mixing in red, mixing after 1 h in blue, 6 h in purple, 24 h in green, 48 h in gray, and 72 h in brown. FRET signal analysis from C—the mixed DOPC LipCo and D—the mixed DPPC LipCo across shorter mixing times. There is no significant difference between DOPC LipCo and DPPC LipCo. Data are presented as mean±standard deviation (n=3).
Figure 9:
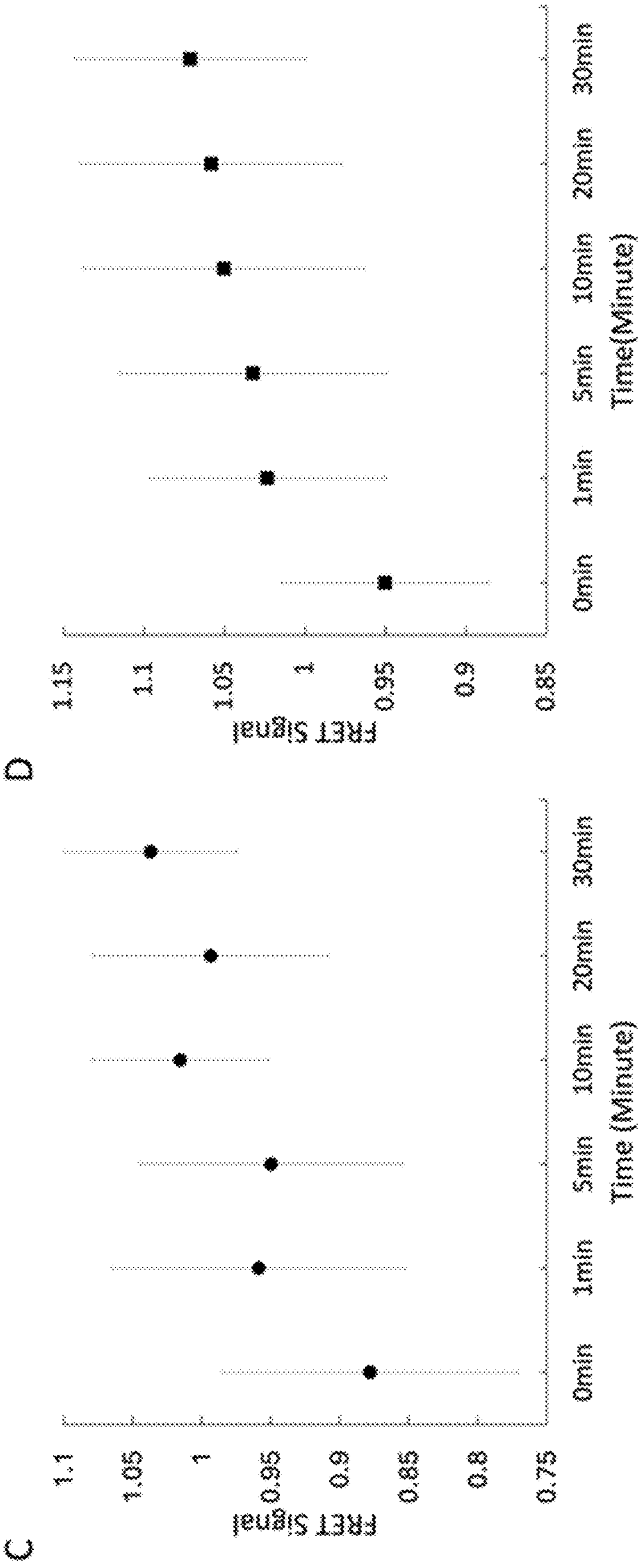

The change in fluorescence emission spectrum from the mixed DOPC LipCo and DPPC LipCo were analyzed (FIGS. 9A and B). After initial mixing, both DOPC LipCo and DPPC LipCo exhibited the higher relative fluorescence intensity at 580 nm (red line), corresponding to rhodamine's maximum emission, compared to FITC-only LipCo (black), suggesting immediate proteins transfer upon mixing. The fluorescence emission in DPPC LipCo surpassed the FITC-only LipCo at initial mixing, 24 h, and 72 h, whereas DOPC LipCo showed multiple emission change at initial mixing, 1 h, 24 h, 48 h, and 72 h. It was also observed DOPC LipCo exhibited higher emission at 580 nm compared to DPPC LipCo, specifically at 0 h ($p<0.01$), 1 h ($p<0.01$), 24 h ($p<0.05$), and 72 h ($p<0.05$) (FIG. 9), suggesting slower diffusion of protein out of DPPC LipCo. FRET signal was analyzed by comparing the fluorescence emission of mixed LipCo at 580 nm with FITC-only LipCo at 520 nm. Similar to the fluorescence emission change spectrum, protein transfer was observed immediately upon mixing (FIGS. 9C and D) in both the mixed DOPC LipCo and DPPC LipCo. There was an increase in extent of FRET signal in both DOPC LipCo and DPPC LipCo in a 30-minutes observation window and reached equilibrium state. No direct evidence suggested a correlation between longer mixing times and increased protein mixing extent (data not shown). Thus, adjusting the concentration of saturated lipid (in this case, DPPC) should provide a way to control the diffusion of proteins out of LipCo.

Figure 10:
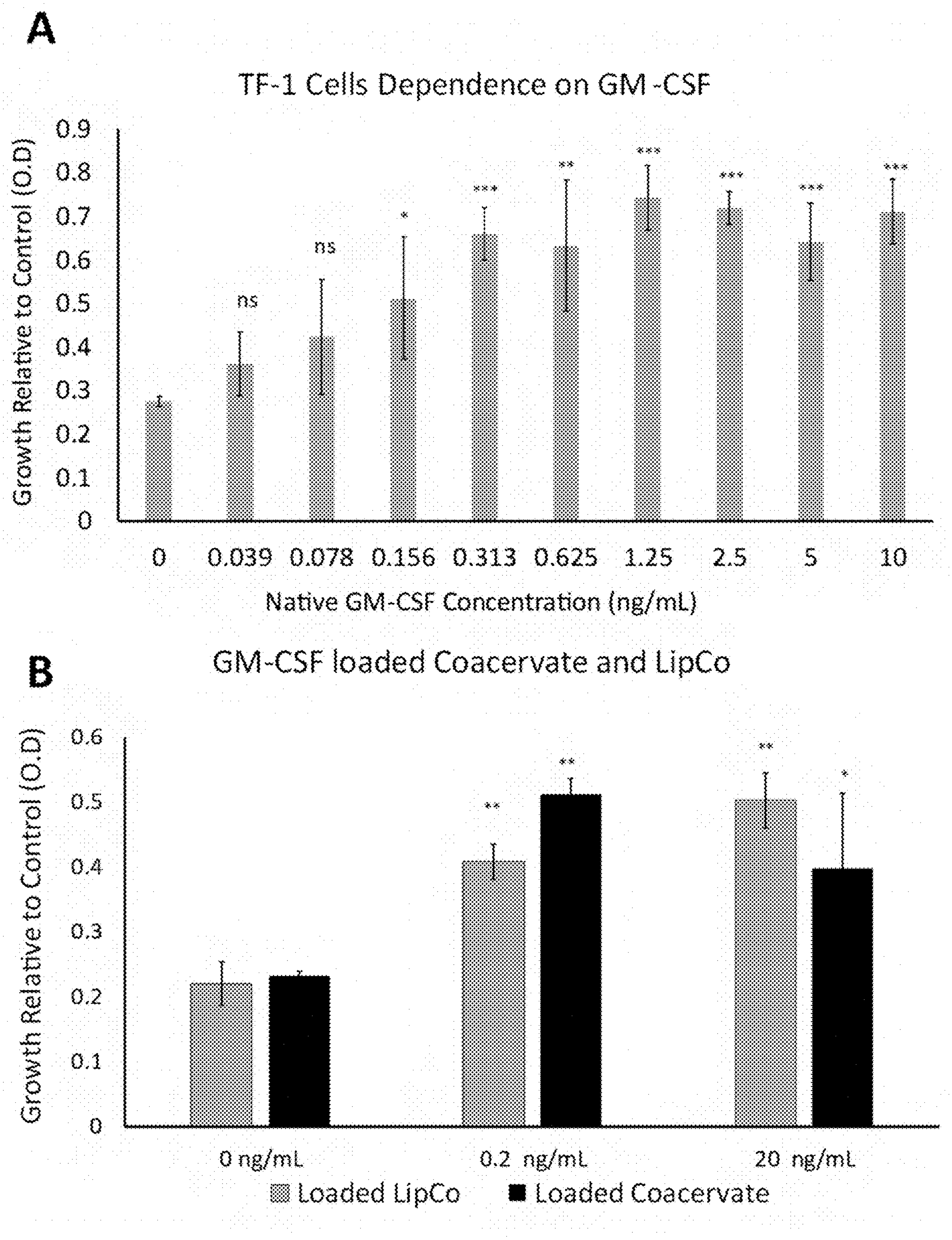
FIG. 10 shows bioactivity of GM-CSF released from LipCo and coacervate. (A) TF-1 cells are a GM-CSF dependent cell line with a dose response seen prior to reaching maximal effect at 1.25 ng/mL. *$p<0.05$, $p<0.01$, *$p<0.001$. (B) GM-CSF loaded coacervate and LipCo induces cell proliferation and is significantly higher than unloaded controls. *$p<0.05$, ** $p<0.01$.

In vitro delivery of GM-CSF to TF-1 cells with LipCo. TF-1 cells were treated with free GM-CSF with concentrations ranging from 0-10 ng/mL, and it was observed that TF-1 cells display a gradual increase in proliferation in response to GM-CSF (FIG. 10A). GM-CSF loaded into LipCo and coacervate at concentrations from 0-20 ng/mL were treated directly onto TF-1 cells. FIG. 10B depicts TF-1 cells proliferating in response to GM-CSF loaded coacervate and LipCo. These results display the ability to successfully deliver GM-CSF from LipCo and coacervate inducing the proliferation of TF-1 cells in vitro.

Discussion Described is the use of a lipid covered coacervate (LipCo) for the successful delivery of GM-CSF with a way to control its size distribution. It was shown that through modulation of concentration and salinity of solutions during coacervate preparation, the size distribution of LipCo can be controlled. With increasing polymer concentration larger vesicles are formed. The charge density of a polymer can also modulate the size of the vesicles.

Due to DPPC's high transition temperature of 41° C. and the gel-like behavior, the lipid structures within DPPC LipCo are more rigid and less mobile compared to those in DOPC LipCo. Consequently, the protein transfer process took a longer time to complete in DPPC LipCo. The ability to exchange and interact with surrounding medium and neighboring droplets is a known property of coacervate. The FRET experiment demonstrates that the same can happen with LipCo. Furthermore, LipCo offers control of exchange rate that is not available in coacervate. This should enable controlled loading of cargos post formation. This could be advantageous for performing surface modification on the LipCo without subjecting loaded cytokines or growth factors to potentially damaging materials used for surface functionalization. LipCo preserved the properties of coacervate to deliver growth factors while maintaining bioactivity. The proliferation rate of TF-1 cells was lower for GM-CSF loaded LipCo and coacervate than observed with free protein. This is likely due to the immediate availability of all the GM-CSF in the free protein group vs. a gradual release, thus smaller concentration of the protein in controlled delivery groups.

LipCos offer a new way to control the delivery of highly unstable growth factors and cytokines. LipCo holds advantages that could be very useful for biologics, such as an organic solvent-free processing, high loading efficiency, and a high degree of tunability.

Example 3

This example describes lipocoacervates of the present disclosure, and methods of making and using same.

Coacervate-filled lipid vesicles (lipocoacervate, LipCo) represent a promising system for enhanced colloidal stability and versatile binding of various growth factors for protein delivery. Vesicle adaptability is crucial to diverse applications. Described are two distinct LipCo formulations with different lipid compositions. Our findings reveal that the vesicle morphology, relative membrane mobility, and subsequent protein release kinetics are characteristics directly influenced by lipid properties. Utilizing two-photon excited fluorescence (2PEF) imaging and intravital imaging, the in vivo circulating behaviors of vesicles in mouse brain capillaries was examined. Both LipCo formulations demonstrate reduced slow-moving and stalled events compared to naked coacervate. Overall, LipCo exhibits remarkable adaptability and holds promise for intravenous administration of therapeutic agents.

LipCo properties with different lipid compositions were characterized, revealing distinct vesicle morphology, membrane mobility, and protein release kinetics. Moreover, the in vivo behaviors of both LipCo formulations were investigated, elucidating their circulation events within mouse brain capillaries. The data indicate the potential of coacervate with lipid assembly as an effective vehicle for the intravenous administration of therapeutic agents.

Materials and Methods. Materials. PEAD was synthesized as previously described. Clinical-grade sodium heparin was a gift from Scientific Protein Labs. Cyanine 5-heparin (Cy-5 heparin) was purchased from Ruixibio. DOPC, DPPC, 1,2-distearoyl-sn-glycero-3-phospho-(1'-rac-glycerol) (sodium salt) (DSPG), 1,2-dioleoyl-sn-glycero-3-phosphoethanolamine-N-(carboxyfluorescein) (ammonium salt) (FITC-PE), 1,2-dioleoyl-sn-glycero-3-phosphoethanolamine-N-(lissamine rhodamine B sulfonyl) (Liss Rhod-PE) and cholesterol were purchased from Avanti Polar Lipids. Fluorescein conjugated bovine serum albumin (FITC-BSA) was purchased from Thermo Fisher Scientific. Recombinant human vascular endothelial growth factor C (VEGF-C), human VEGF-C DuoSet ELISA kit, and Duoset ELISA Ancillary Reagent Kit 2 were purchased from R&D Systems. Bovine serum albumin (BSA) was purchased from VWR Chemicals. 0.9% normal saline was purchased from Growcells. A membrane fluidity kit was purchased from Abcam. All reagents were purchased and used without further purification.

LipCo preparation. LipCo was prepared as previously described. Briefly, 10 mg/ml of PEAD and heparin solution were dissolved in 0.9% normal saline. 40 μl of heparin was complexed with 160 μl of PEAD to form coacervate with PEAD to heparin mass ratios of 4 (P/H=4). 10 μl of DOPC/DSPG/cholesterol (molar ratio=5:1:4) or DPPC/DSPG/cholesterol (molar ratio=5:1:4) ethanol solution was then added into PEAD/heparin complex coacervate suspension to achieve a final weight ratio of 5% (lipid: coacervate). The LipCo suspension was then gently shaken on an orbital shaker at 50 rpm for 1 hour. The LipCo suspension was then centrifuged at 300 g for 5 minutes. The resultant supernatant was discarded to remove the excessive ethanol. Then the LipCo pellet was resuspended with 200 μl of 0.9% saline. As for VEGF-C loaded LipCo, 500 ng of VEGF-C was complexed with 40 μl of heparin solution for 5 minutes prior to adding 160 μl of PEAD solution, and all other procedures were as described above. To prepare heated DPPC LipCo, the vial of LipCo suspension was heated in a hybridization oven at 45° C. for 1 hour. The heated DPPC LipCo was then cooled to room temperature, and all other procedures were as described above. As for the retro-orbital injection, PEAD and heparin solution were filtered with a 0.22 μm filter. All other procedures were performed in a biosafety cabinet to keep the sterility.

Small angle X-ray scattering (SAXS). DPPC/1,2-dipalmitoyl-sn-glycerol-3-phospho-(1'-rac-glycerol) (DPPG) vesicle was kindly provided by Professor Mu-Ping Nieh at University of Connecticut, Storrs Connecticut. DPPC/DPPG vesicle was used as a lipid bilayer vesicle standard. SAXS measurements were conducted as previously described.

Fluorescence recovery after photobleaching (FRAP). For FRAP measurement, both DOPC LipCo and DPPC LipCo were prepared with FITC-PE to achieve the final weight ratio of 1% (fluorescent lipids to total lipids). FRAP measurement was conducted utilizing a Zeiss LSM880 confocal multiphoton inverted microscopy with a 40× water immersion objective. A rectangular region of interest (ROI) was designated at the periphery of the LipCo. Photobleaching was performed using an argon 488 nm laser at a maximum of 20% intensity. Emission signals were collected within the range of 499-589 nm, with image acquisition performed laser intensity of 1%. Photobleaching was sustained for 50 frames across the designated ROI. Following photobleaching, the laser was reduced to an attenuated level, and the recovery images were recorded for 8 min. Images were recorded in the bidirectional scan mode. FRAP analysis was conducted using NIH ImageJ software.

Relative membrane fluidity test. Relative lipid membrane fluidity was tested via an Abcam membrane fluidity kit. Briefly, 100 μM of pyrene decanoic acid (PDA) stock solution was diluted with 0.9% saline to reach the final concentration of 5 μM. To prepare the labeling solution, 0.08% (v/v) of Pluronic F127 was supplemented with 5 μM of PDA in 0.9% saline. 200 μl of DOPC, DPPC, and heated DPPC LipCo suspension were prepared as described above. 200 μl of labeling solution was then added and incubated with LipCo for 1 hour at 25° C. in the dark. For the heated DPPC LipCo, the labeling solution was incubated with LipCo for 1 hour at 45° C. in the dark. The fluorescence readings at 400 nm as PDA monomer and 460 nm as PDA excimer were immediately measured via a microplate reader. A ratio of excimer to monomer fluorescence represents the relative membrane fluidity.

Confocal microscopy. Confocal microscopic images were obtained using a Leica SP8 microscope with a 60× oil immersion objective. The Lecia confocal microscope was kindly provided by Professor Esak Lee at Cornell University, Ithaca New York.

Growth factors loading and in vitro release. VEGF-C loaded LipCo was prepared as described above. Each sample contained 500 ng of VEGF-C. 1% bovine serum albumin in 0.9% normal saline was used as a release buffer solution. After initial formation, protein-loaded LipCo was immediately centrifuged at 12100 g for 10 minutes, and the supernatant was collected and analyzed via ELISA to indirectly access growth factor loading efficiency. LipCo pellets were gently resuspended with release buffer solution and incubated at 37° C. for subsequent time points. For each time point, samples were spun down and supernatants were collected and stored at −20° C. until analysis via ELISA.

Cranial window implantation. Three weeks prior to in vivo two-photon excitation fluorescence imaging mice were implanted with a cranial window centered over the sagittal sinus using a sterile technique. Mice were anesthetized with 3% isoflurane mixed with 100% $O_2$, injected with glycopyrrolate (0.5 mg/100 g i.m.), 200 μl glucose (5% in 0.9% saline, s.c.), ketoprofen (0.5 mg/100 g, s.c.), and dexamethasone (0.025 mg/100 g, s.c.), the latter two were administered for an additional two days after surgery. During the procedure mice were maintained on 1.5-2% isoflurane. Six alternating swabs of povidone and 70% ethanol were used to create a sterile field prior to providing a local anesthetic (bupivacaine 0.125%, 100 μl, s.c.), after which an incision was made to expose the skull, and meninges and skin pushed to the edges of the skull. Vetbond® was applied to the edge of skin and exposed skull to facilitate a 6-mm craniotomy using a manual dental drill (0.5 mm drill bit). Once the skull fragment was removed using forceps, a piece of surgifoam was applied to stop any bleeding prior to placing an 8-mm diameter round glass coverslip (1.5 mm thickness, Electron Microscopy Sciences #72296-08), which was affixed to the remaining skull using cyanoacrylate (Loctite 406). The coverslip was allowed to adhere for 6 minutes before surrounding it with dental cement to cover any remaining exposed skull and create a small well for water immersion objectives during imaging.

In vivo two-photon excitation fluorescence (2PEF) imaging. During two-photon imaging sessions, mice were kept under 1-1.5% isoflurane mixed with medical air (21% 02, 78% $N_2$), placed on a custom-made stereotactic frame, and injected with glycopyrrolate (0.5 mg/100 g i.m.), 5% glucose (100 μl/h of imaging, s.c.), 50 μl of Texas Red 70 kDa dextran (2.5% diluted in 0.9% saline, r.o.) to visualize the cerebral vasculature, in some mice, leukocytes and blood platelets were labeled by injecting Rhodamine 6G (50 μL, 1 mg/mL in 0.9% saline), and Hoescht 33342 (50 μL, 4.8 mg/mL in 0.9% saline). 40 μl of 10 mg/ml FITC-BSA was loaded in coacervate, DOPC LipCo, and DPPC LipCo to visualize vesicles, and all the preparation steps are as described in the LipCo preparation section. 200 μl of vesicle in 0.9% saline was injected via a retro-orbital sinus. Breathing rate was maintained at 1 Hz by adjusting isoflurane levels, and body temperature was monitored and kept at 37° C. throughout imaging sessions. Laser scanning and data acquisition were controlled by ScanImage software through MATLAB. Images from up to 5 locations (1-3 capillary beds, one vein, and one artery) were acquired with a 25× water immersion objective (Olympus, NA of 1.05) by resonant scanning (1000 frames, 33 Hz, 512×512 pixels/line) every 20 min up to 2 h after injections. Imaging was performed using an excitation wavelength of 830 nm, 100-fs pulses from a Ti: Sapphire laser oscillator (Chameleon, Coherent). Emitted fluorescence was detected on a four-channel detection system: For capillary stalling analysis, a 488 nm dichroic was used to split channels 1/2 from 3/4, 560 nm dichroic for separating channels 1 and 2, and 801 nm dichroic for channels 3 and 4. For 4-channel imaging in veins and arteries, a 532 nm dichroic was used to split channels 1/2 from 3/4, 488 nm dichroic for separating channels 1 and 2, and 593 nm dichroic for channels 3 and 4. Additional band-pass filters were used to visualize Hoescht in channel 1 (439/154), Rhodamine 6G in channel 2 (494/41, FITC in channel 3 (579/34), and blood vessels in channel 4 (645/55).

In vivo event analysis. The captured LipCo images in the mice's brain capillaries were analyzed to identify vesicle behavioral events in vivo. There were three identified events: flowing, slow-moving, and non-following. For the flowing LipCo vesicles, the images were analyzed via NIH Image J script FindPeaks within the regions of interest. When a flowing vesicle passed through the region of interest, a single event would be recorded via the script. As for the slow-moving and non-flowing events, images were examined manually. The slow-moving events will be recorded as a single vesicle moved and remained in the same observation window for up to 5 seconds. Non-flowing events were recorded when a single vesicle became stocked and remained in the same observation window for more than 20 seconds.

Statistics. Data were presented as mean±standard deviation. The statistical significance was determined by Student's t-test.

Figure 11:
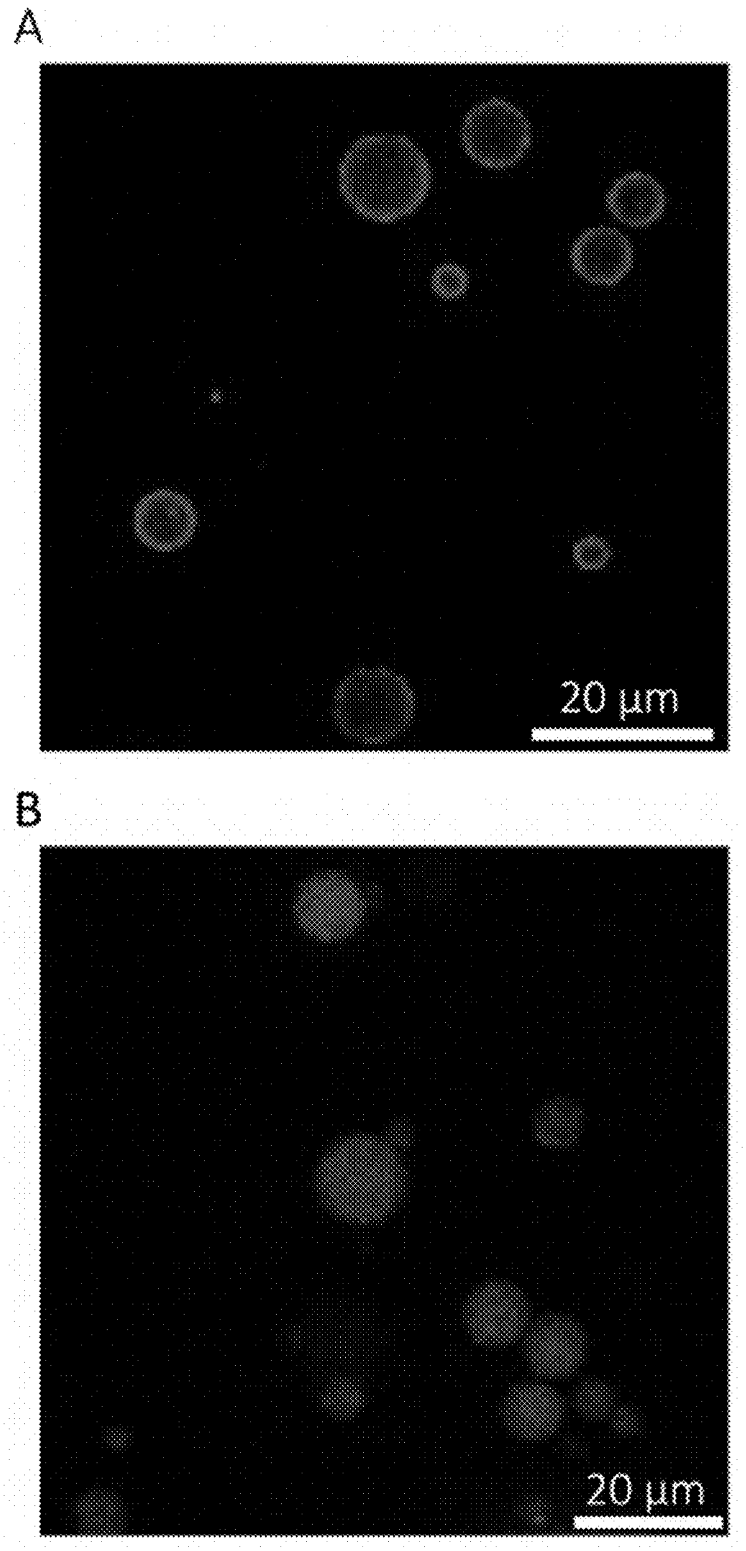
FIG. 11 shows confocal microscopic images of LipCo. A-LipCo prepared with red fluorescent DOPC/DSPG/cholesterol lipid mixtures possesses an outer shell structure. Red: Rhodamine-PE. Scale bar: 20 μm. B-LipCo prepared with red fluorescent DPPC/DSPG/cholesterol lipid mixtures showed lipids distributed across each individual LipCo. Red: Rhodamine-PE. Scale bar: 20 μm.

Results. LipCo preparation and characterization. DOPC LipCo and DPPC LipCo formed through PEAD and heparin coacervation, followed by lipid assembly. In FIG. 11A, DOPC LipCo displayed discrete spherical vesicles with a vivid red fluorescent outer shell (Liss Rhod-PE), consistent with the previously reported[21]. In the case of DPPC LipCo, it was also noted individually separated spherical structures. Interestingly, DPPC LipCo exhibited a compact vesicular morphology with abundant red fluorescence puncta distributed throughout the entire structure (FIG. 11B).

Figure 12:
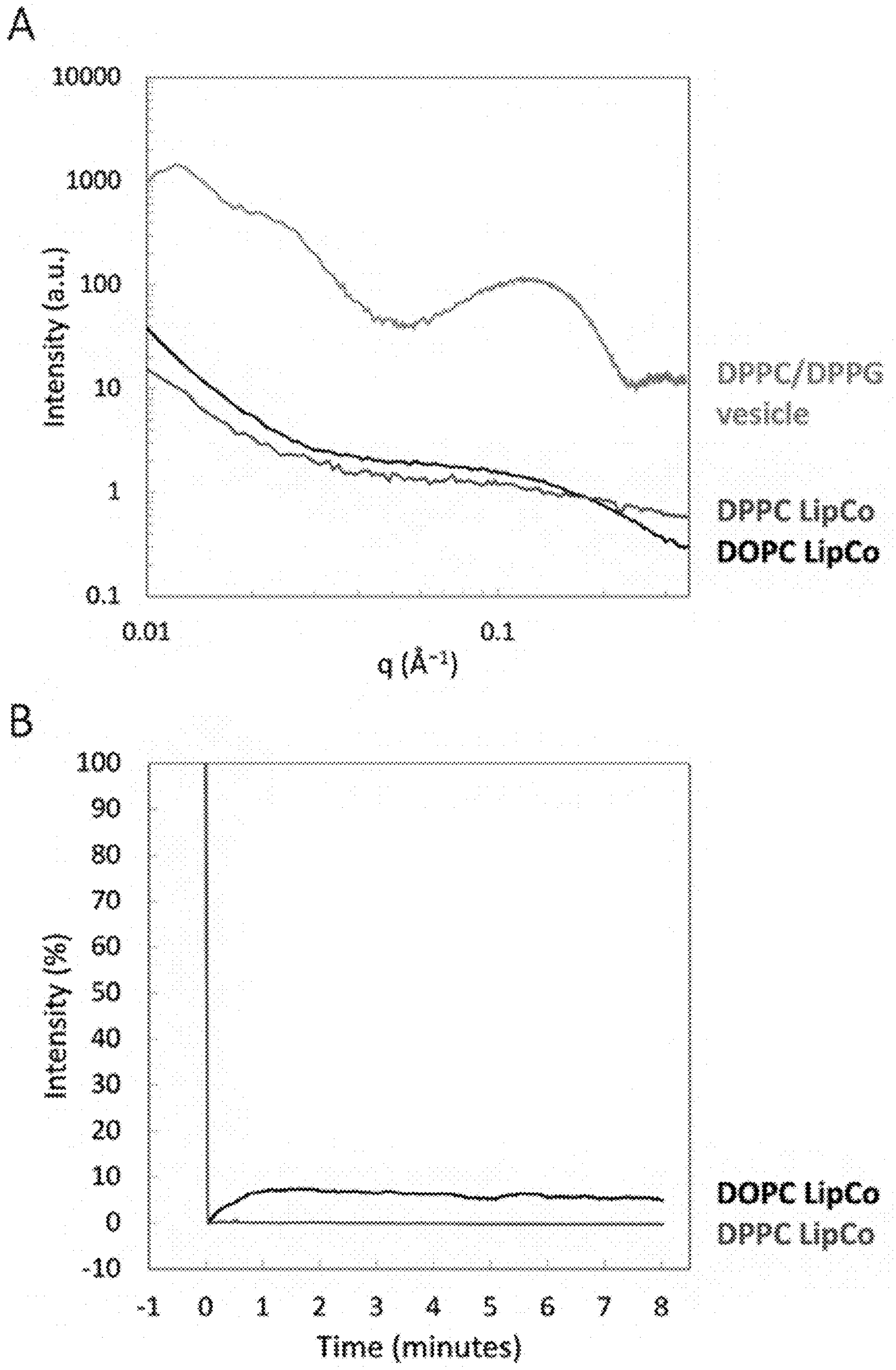
FIG. 12 shows surface characterization of LipCo. A—SAXS profiles of DPPC/DPPG vesicle (grey line), DOPC LipCo (black line), and DPPC LipCo (red line). The first and second-order Bragg reflections were present at q=0.1 and 0.3 Å-1 in DPPC/DPPG vesicle as an indication of lipid bilayer structure. B—FRAP measurement of membrane fluidity of DOPC LipCo (black line) and DPPC LipCo (red line), showing relatively slow and zero fluorescence intensity recovery.

To investigate the distinct LipCo morphology, small-angle X-ray scattering (SXAS) and fluorescence recovery were examined after photobleaching (FRAP) on both LipCo formulations. In the SAXS studies, DPPC/DPPG vesicle was used as a reference for the lipid bilayer structure. The first and second-order Bragg reflection peaks were observed at 0.1 and 0.3 $Å^{-1}$, indicating the presence of a lamellar phase in the DPPC/DPPG vesicle (FIG. 12A, gray line). In both DOPC LipCo (FIG. 12A, black line) and DPPC LipCo (FIG. 12A, red line) SAXS profiles, no evidence of the two Bragg reflection peaks was found, suggesting that the lipid assembly was in a monolayer configuration.

Both DOPC LipCo and DPPC LipCo demonstrated limited fluorescence intensity recovery in FRAP experiments (FIG. 12B), indicating reduced membrane fluidity. Pyrene decanoic acid (PDA) was used as a lipophilic pyrene probe to assess relative membrane fluidity. PDA undergoes dimerization and forms excimers from PDA monomer through lateral diffusion in the fluid membrane. The fluorescence emission ratio between excimer and monomer is proportional and indicative of the relative membrane fluidity. Both DOPC LipCo and DPPC LipCo demonstrated relatively low membrane fluidity (FIG. 13), with DPPC LipCo showing comparatively lower membrane fluidity than DOPC LipCo. This was attributed to DPPC's high transition temperature of 41.3° C., causing DPPC to be in a solid-like gel state at room temperature. In contrast, DOPC's low transition temperature of −16° C. allows DOPC to exist in a fluid-like liquid crystalline state at room temperature.

Figure 14:
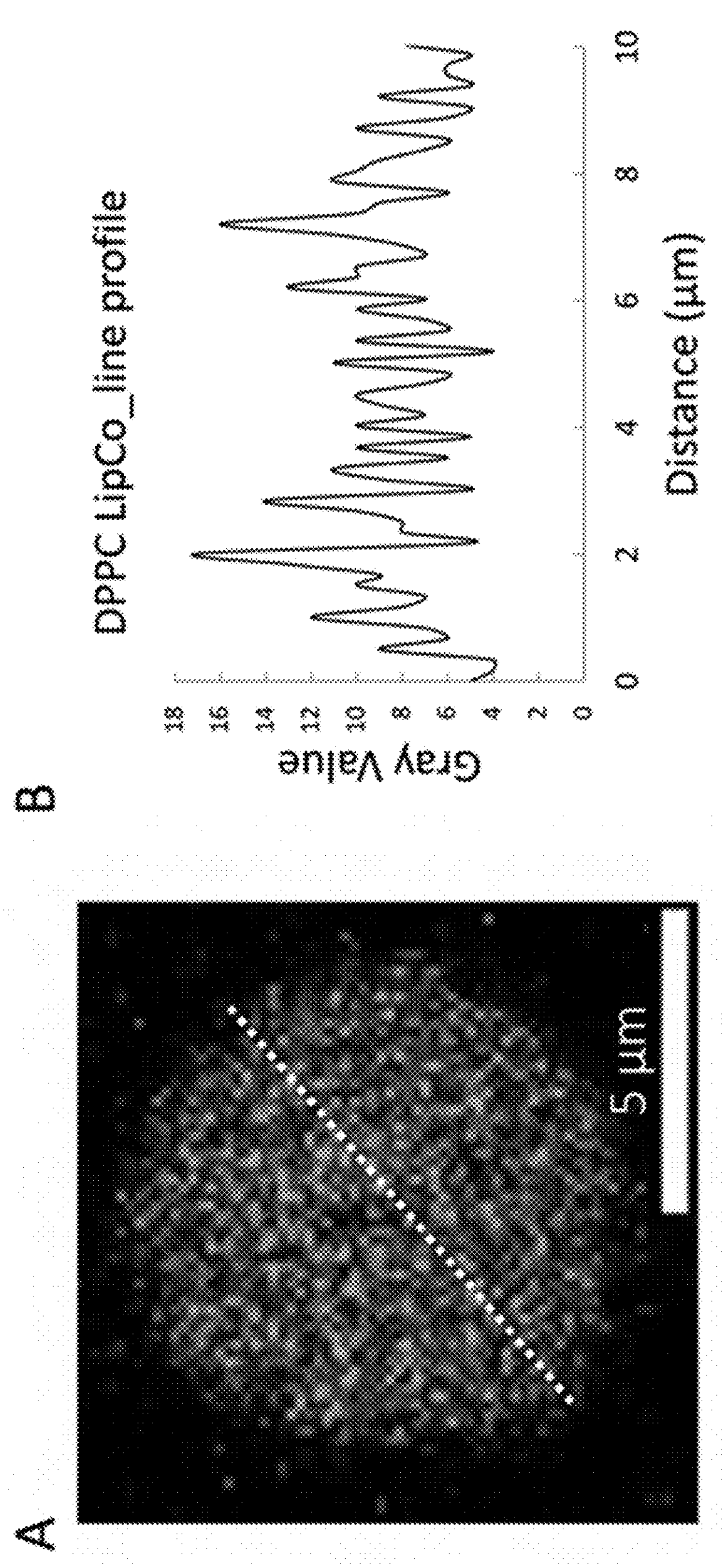
FIG. 14 shows confocal microscopic images of DPPC LipCo and fluorescence intensity measurement. A-Confocal microscopic image of DPPC LipCo. Green: FITC-PE. Scale bar: 5 μm. B—The corresponding fluorescence intensity measurement of DPPC LipCo from the dashed line in A. C-Confocal microscopic image of heated DPPC LipCo. Green: FITC-PE. Scale bar: 5 μm. D—The corresponding fluorescence intensity measurement of heated DPPC LipCo from the dashed line in C.
Figure 14:
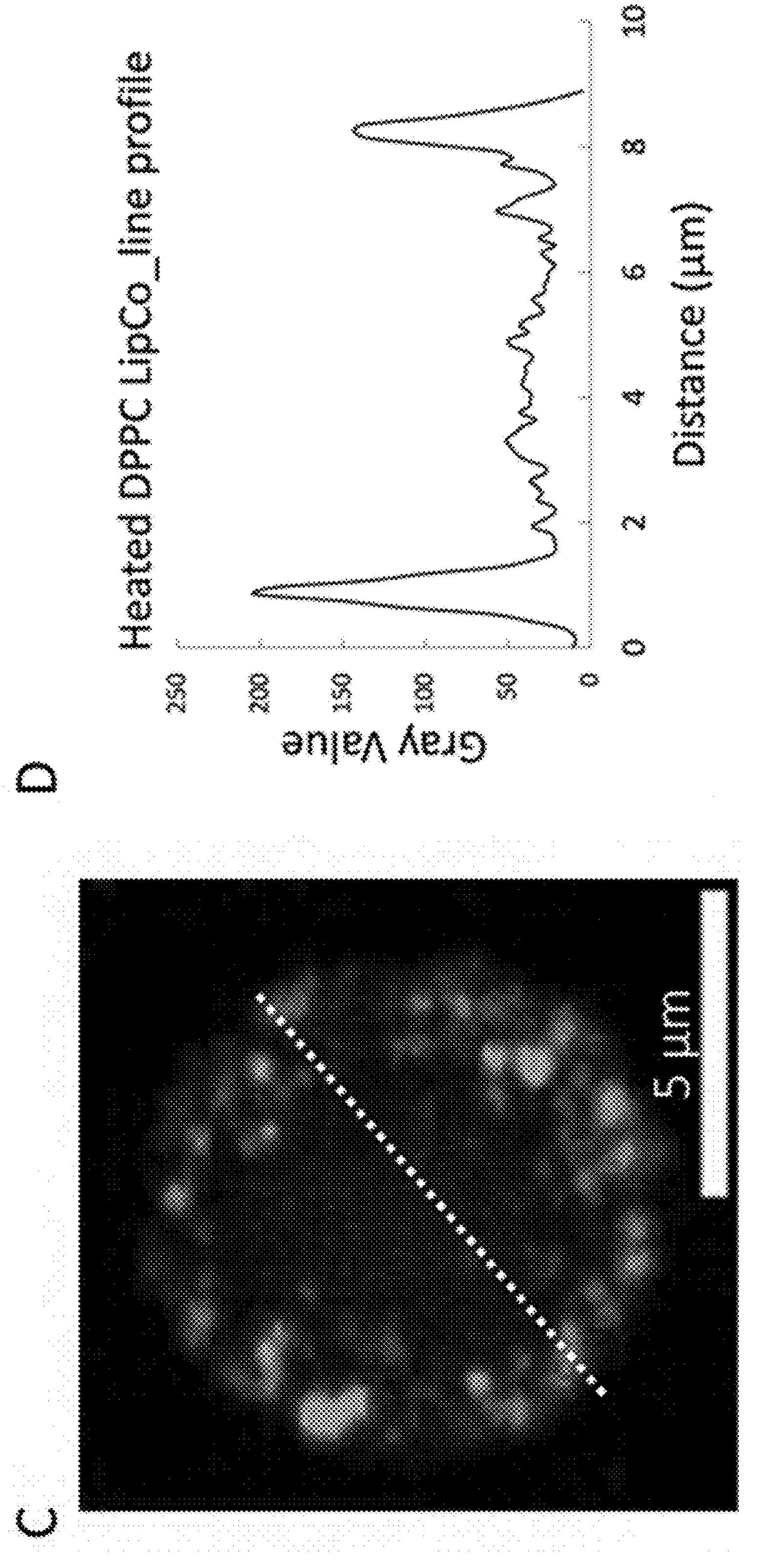

Given the fact that DPPC possesses high transition temperature with a solid-like gel state at room temperature, the surrounding temperature is a key factor in controlling lipid assembly. When DPPC LipCo was prepared at 45° C. (heated DPPC LipCo), the green fluorescence puncta (FITC-PE) distributed toward the edge of vesicle (FIG. 14C), compared to DPPC LipCo prepared at 25° C. with the fluorescent lipids distributed throughout the entire structure (FIG. 14A). The line profile measurement confirmed the fluorescent lipids distribution was evenly distributed across DPPC LipCo at 25° C. (FIG. 14B), and there were two peaks at the edge of DPPC LipCo at 45° C. (FIG. 14D).

Figure 15:
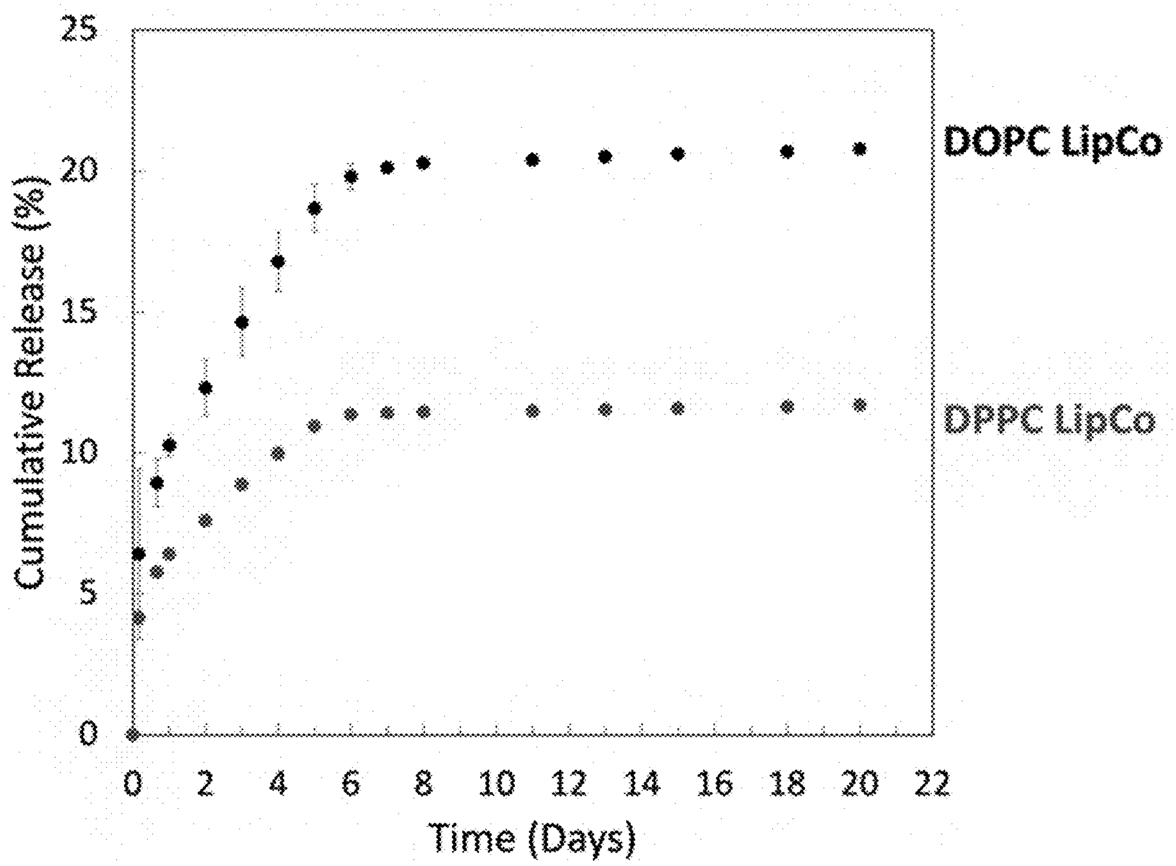
FIG. 15 shows in vitro cumulative release profiles of growth factors. VEGF-C was released from both DOPC LipCo (black square) and DPPC LipCo (red square) in 0.9% normal saline with 1% BSA (v/v). Data are presented as mean±standard deviation (n=3).

In vitro protein release. Considering the different lipid membrane mobility observed in FIG. 12B and FIG. 13, different protein release kinetics from DOPC LipCo and DPPC LipCo were expected. The loading efficiency of VEGF-C was 92% in DOPC LipCo and 93% in DPPC LipCo. For DOPC LipCo, 20% of VEGF-C were released after one week (FIG. 15, black spheres), which is consistent with what was previously observed. On the other hand, 10% of VEGF-C was released from DPPC LipCo (FIG. 15, red spheres) after one week. This difference was attributed to the rigid lipid membrane and reduced lipid membrane mobility on DPPC LipCo to slow down the release. This finding provides a design criterion to formulate LipCo with different phospholipid mixtures and tune the protein release rate for various applications.

Figure 16:
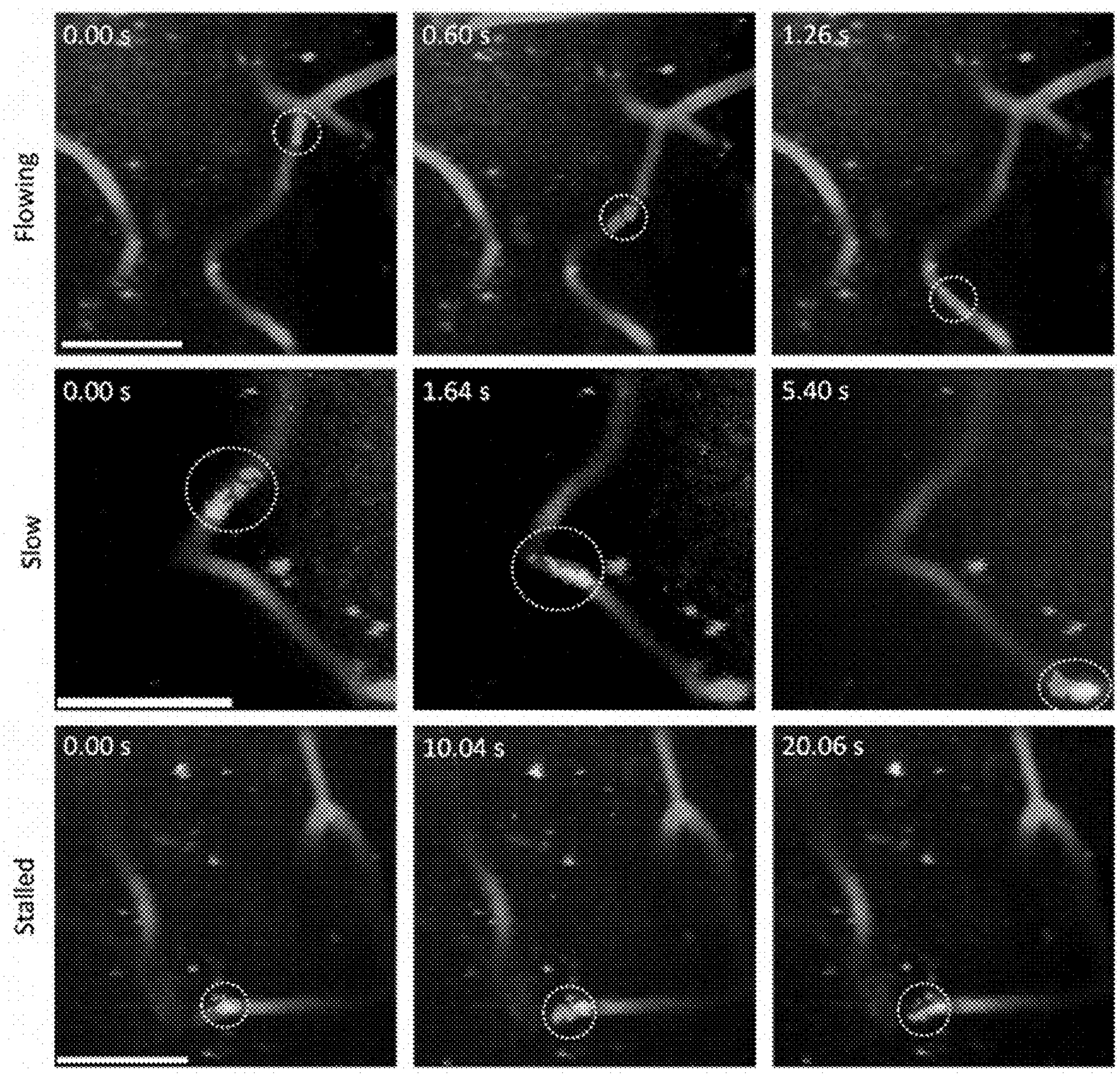
FIG. 16 shows a sequence of two-photon microscopic images of vesicles in mouse brain capillaries as flowing, slow, or stalled. Blood plasma was labeled Texas-Red (green), and the vesicle was labeled with FITC-BSA (red). White dashed circles represent vesicles flowing, slow-moving, or stalled in the brain capillaries. Scale bar: 50 μm.
Figure 17:
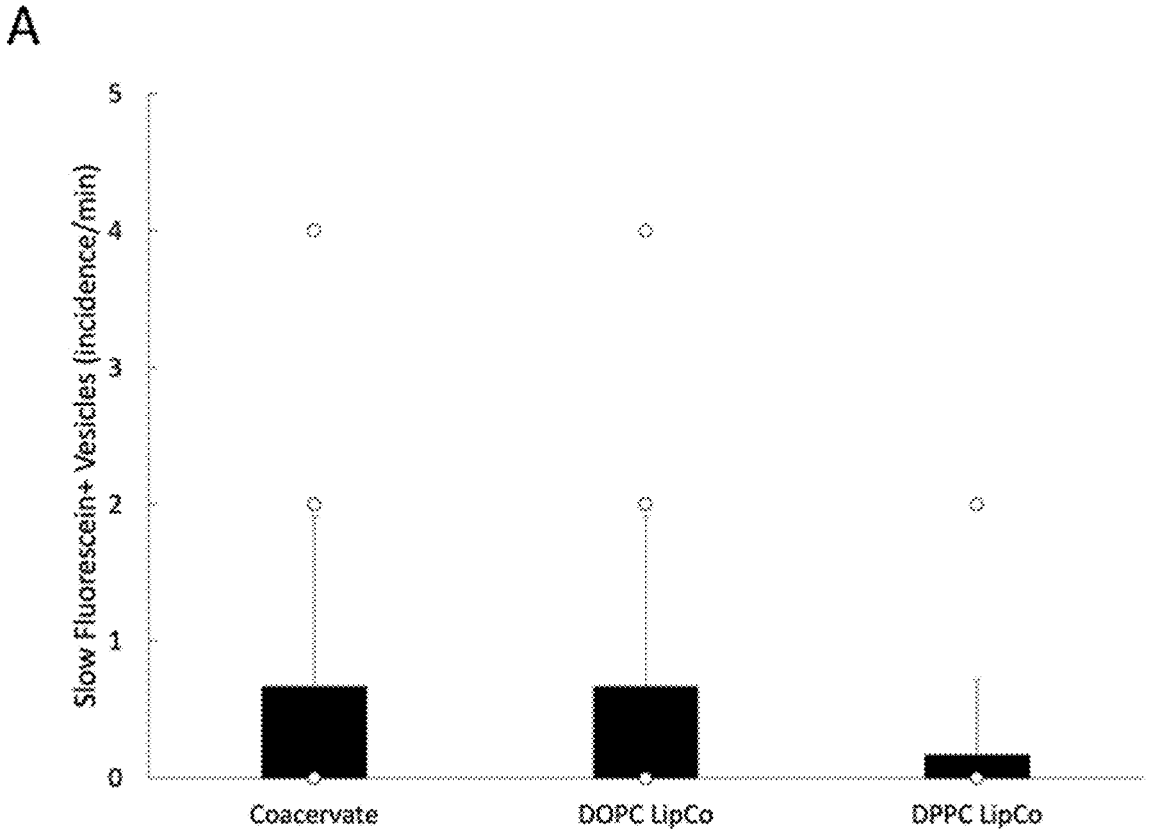
FIG. 17 shows vesicle circulation event analysis. A-Slow fluorescein-positive vesicles. There was no significant difference observed among coacervate, DOPC LipCo, and DPPC LipCo. B-Stalled fluorescein-positive vesicles. Data are presented as mean±standard (n=3). The open circles represent the actual data point. ***: p<0.001. N.S.: non-significant.
Figure 17:
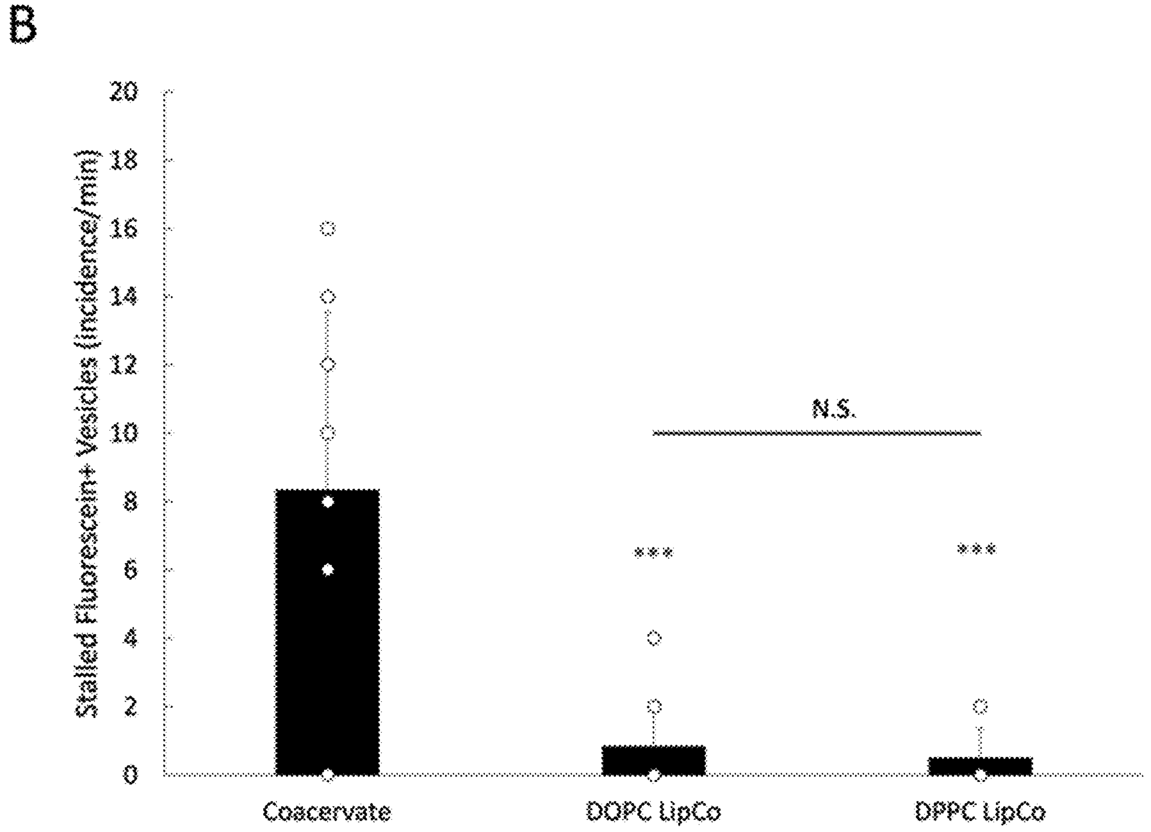

In vivo circulation behavior of DOPC LipCo and DPPC LipCo. To examine the feasibility of utilizing LipCo to deliver therapeutic proteins in vivo, the circulation behavior of both LipCo formulations was investigated in mice brain capillaries using 2PEF microscopy and intravital imaging techniques. The cerebral vasculatures were labeled with Texas Red dextran, leukocytes was labeled by injecting rhodamine 6G and Hoechst. Coacervate, DOPC LipCo, and DPPC LipCo were loaded and labeled with FITC-BSA and injected via a retro-orbital sinus. Three distinct events were recorded flowing vesicles, slow-moving vesicles, and stalled vesicles (FIG. 16). As a protein delivery vehicle aims to be systemically administered, there is particular interested in a vesicle with slow-moving and stalled events in capillaries. As shown in FIG. 17A, no significant difference in slow-moving events was observed among coacervate, DOPC LipCo, and DPPC LipCo. However, the frequency of stalled events decreased with the incorporation of lipids in both DOPC LipCo and DPPC LipCo compared to coacervate (FIG. 17B). Both LipCo formulations exhibited a low number of stalled events, with no significant difference observed between DOPC LipCo and DPPC LipCo. It is worth mentioning that, both coacervate and LipCo squeeze through the narrowed capillaries with some extent of deform (Observed in 2PEF video, data not shown here), suggesting PEAD/heparin complex coacervate possess the ability to minimize flow resistance and enable passage through capillaries. These findings suggest the promising potential for LipCo as an effective carrier for therapeutic protein delivery in vivo, emphasizing the ability to navigate capillary circulation efficiently and prevent clot formation.

Figure 13:
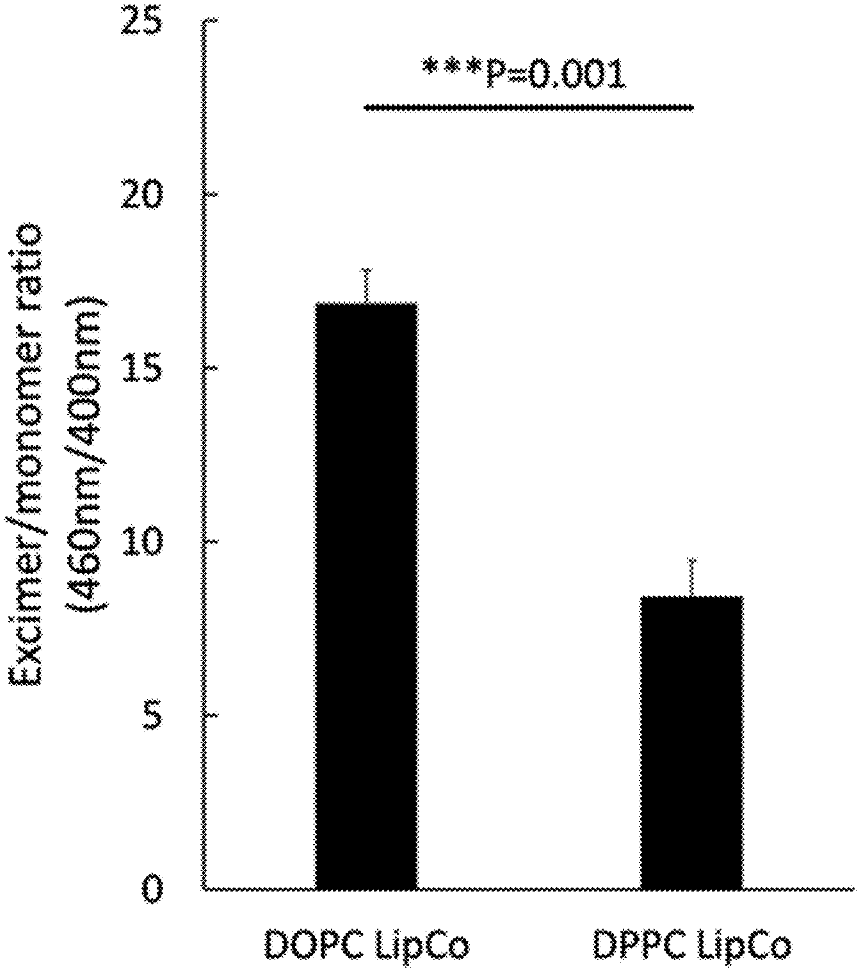
FIG. 13 shows the relative membrane fluidity of LipCo. Both DOPC LipCo and DPPC LipCo were incubated with 5 μM PDA and 0.08% (v/v) Pluronic F-127. PDA fluorescence was measured at 400 nm (monomer) and 460 nm (excimer). Relative membrane fluidity is determined as the ratio of excimer to monomer fluorescence. ***: p<0.001.
Figure 18:
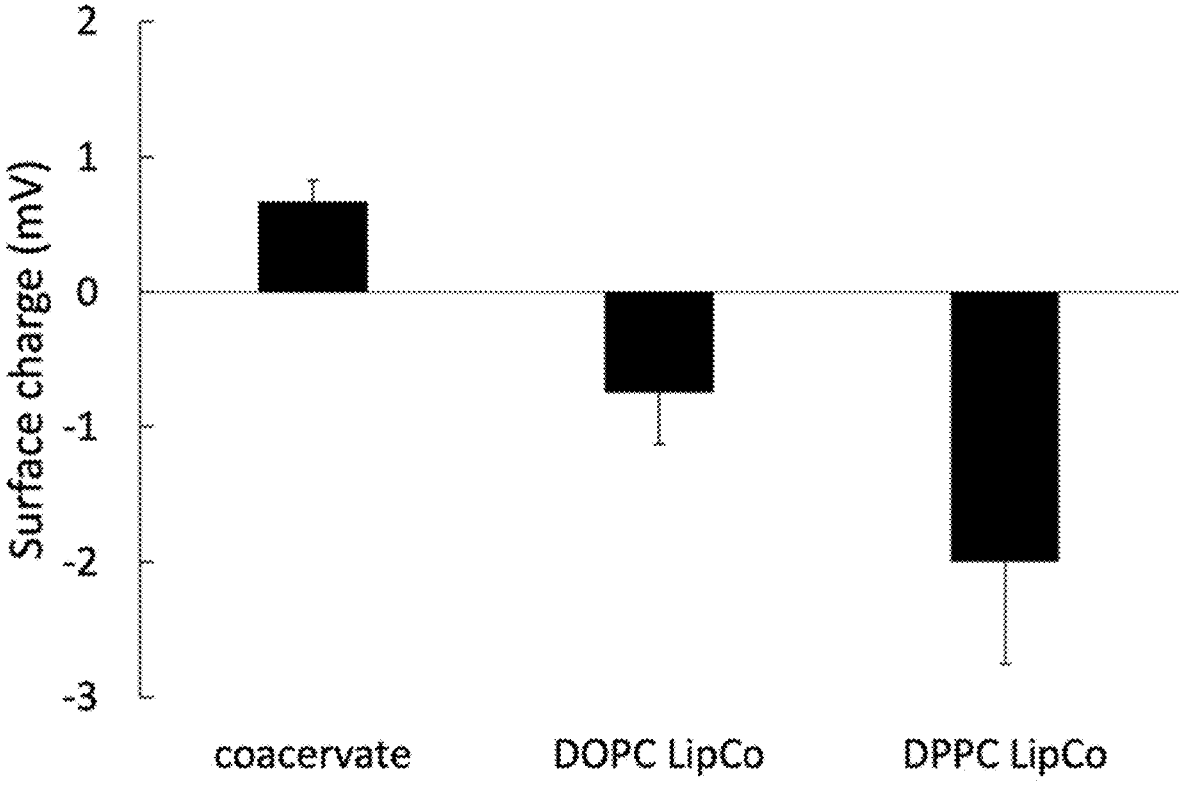
FIG. 18 shows surface charge measurement of the vesicle. PEAD/heparin complex coacervate, DOPC LipCo, and DPPC LipCo were prepared with a PEAD to heparin mass ratio of 4, showing the charge reduction after the addition of lipids mixture. No significant difference was observed between DOPC LiPCo and DPPC LipCo.

Discussion Electrostatically mediated lipid assembly on coacervate surfaces drives surface absorption. In this study, PEAD/heparin complex coacervate (at a mass ratio of 4) produced slightly positively charged vesicles (+0.673±0.15 mV). Upon addition of negatively charged DOPC/DSPG/cholesterol and DPPC/DSPG/cholesterol, LipCo surface charge decreased to −0.74±0.38 mV and −1.99±0.76 mV, respectively (FIG. 18). The weak electrostatic interaction between PEAD/heparin complex coacervate and the negatively charged lipid mixture may result in lipid monolayer formation on the coacervate surface dominated by hydrophobic interaction (FIG. 12A) and relatively low membrane fluidity (FIG. 12B and FIG. 13). These diverse lipid membrane properties offer opportunities for tailored design of coacervate-based lipid vesicles for various applications.

Complex coacervates, as electrostatically bound liquid-liquid phase separations, are highly influenced by environmental factors. Upon injection into the bloodstream, various ionic species such as sodium, magnesium, chloride, calcium, phosphate, and potassium can disrupt the charge interaction between the polycation and polyanion, leading to the breakdown of complex coacervates. Additionally, free proteins such as albumin and fibrinogen may adsorb onto the coacervate surface, forming protein corona and aggregation that significantly influences the vesicle's biological behavior.

Using 2PEF imaging, circulation of complex coacervates and LipCo in the mouse bloodstream was observed for the first time. Both coacervate and LipCo retained their structural integrity after injection during a 2-hour observation period. Analysis of 2PEF imaging data revealed a relatively high number of stalled events in complex coacervates (FIG. 17B), indicating potential interactions with endothelial cells on vessel walls or coagulation with blood components. Both LipCo formulations with negatively charged DSPG provided electrostatic repulsion and reduced the occurrence of stalled events (FIG. 17B). Further studies are needed to investigate how complex coacervates and LipCo interact with blood cells to better understand their in vivo behavior.

Conclusions. This study's key findings reveal significant insights into LipCo as a tunable protein delivery vehicle. LipCo formulations with diverse lipid compositions displayed distinct characteristics in terms of morphology, membrane mobility, and protein release kinetics. The 2PEF imaging observation in mouse brain vasculature unveiled three circulating events: flowing, slow-moving, and stalled, shedding light on LipCo's behavior in vivo. Notably, both DOPC LipCo and DPPC LipCo formulations exhibited reduced stalled events compared to coacervate, without a significant difference between the two LipCo types. These findings underscore the promising utility of LipCo for the intravenous administration of therapeutic agents, emphasizing its potential as a versatile protein delivery system.

Example 4

This example describes lipocoacervates of the present disclosure, and methods of making and using same.

The circulation dynamics and biodistribution of colloidal drug carriers play pivotal roles in their therapeutic efficacy. In this study, in vivo circulation of PEAD/heparin complex coacervate and DOPC LipCo vesicles were investigated using two-photon excited fluorescence (2PEF) microscopy and intravital imaging techniques. The coacervate vesicles demonstrate interactions with white blood cells, slower movement, and a higher incidence of stalling along vessel walls. Conversely, DOPC LipCo exhibits minimal interaction with white blood cells and higher overall flowing events, indicating a stealthier circulation pattern. Biodistribution analysis reveals rapid hepatic accumulation and renal clearance for coacervate vesicles, while DOPC LipCo shows gradual liver accumulation, suggestive of the potential for extended circulation. Furthermore, LipCo formulations mimicking erythrocyte membrane composition exhibit prolonged fluorescence decay in the liver, indicating prolonged circulation, with an initial elimination half-life of 17 hours. These findings underscore the potential of LipCo with glycolipid to evade rapid clearance and enhance therapeutic delivery.

Described is a lipid encapsulated liquid condensate (LLC) that circulates an order of magnitude longer than PEGylated nanoliposome. A single layer of lipid surrounds these LLC. Two-photon excited fluorescence (2PEF) microscopy and in vivo imaging system (IVIS) are utilized to examine the vesicle circulation and biodistribution. Furthermore, LipCo was formulated with 34:1 PC/ganglioside/cholesterol to mimic the erythrocyte outer membrane leaflet. Data indicate that LipCo with glycolipid possesses an extended initial elimination half-life of 17 h in mice plasma.

Materials and Methods. Materials. PEAD was synthesized as previously described. Clinical-grade sodium heparin was a gift from Scientific Protein Labs. Cyanine 5-heparin (Cy-5 heparin) was purchased from Ruixibio. DOPC, 1,2-distearoyl-sn-glycero-3-phospho-(1'-rac-glycerol) (sodium salt) (DSPG), 1-palmitoyl-2-oleoyl-glycero-3-phosphocholine (34:1 PC), total ganglioside extract (brain, porcine-ammonium salt), and cholesterol were purchased from Avanti Polar Lipids. Fluorescein conjugated bovine serum albumin (FITC-BSA) was purchased from Thermo Fisher Scientific. 0.9% normal saline was purchased from Growcells. Phosphate buffer saline (PBS) was purchased from VWR. All reagents were purchased and used without further purification.

Vesicle preparation. LipCo was prepared as previously described. Briefly, 10 mg/ml of PEAD and heparin solution were dissolved in 0.9% normal saline and filtered with a 0.22 μm filter. 40 μl of heparin was complexed 40 μl of 10 mg/ml of FITC-BSA for 5 minutes prior to adding 160 μl of PEAD to form coacervate with PEAD to heparin mass ratio of 4 (P/H=4). 10 μl of DOPC/DSPG/cholesterol (molar ratio=5:1:4) ethanol solution was then added into PEAD/heparin complex coacervate suspension to achieve a final weight ratio of 5% (lipid: coacervate). The LipCo suspension was then gently shaken on an orbital shaker at 50 rpm for 1 hour in the dark. The LipCo suspension was then centrifuged at 300 g for 5 minutes. The resultant supernatant was discarded to remove the excessive ethanol. Then the LipCo pellet was resuspended with 200 μl of sterilized 0.9% saline. All procedures were performed in a biosafety cabinet to keep the sterility. For the Cy-5 heparin-loaded coacervate and DOPC LipCo, 25% (v/v) of Cy-5 heparin was prepared in 0.9% saline solution. 40 μl of 25% Cy-5 heparin was then complex with 160 μl of PEAD solution. Other procedures were as described above. For LipCo with glycoprotein, PEAD/heparin complex coacervate vesicles were incubated with 34:1 PC/ganglioside/cholesterol (molar ratio=2:2:1). Other procedures were as described above.

Cranial window implantation. Three weeks prior to in vivo two-photon excitation fluorescence imaging mice were implanted with a cranial window centered over the sagittal sinus using a sterile technique. Mice were anesthetized with 3% isoflurane mixed with 100% $O_2$, injected with glycopyrrolate (0.5 mg/100 g i.m.), 200 μl glucose (5% in 0.9% saline, s.c.), ketoprofen (0.5 mg/100 g, s.c.), and dexamethasone (0.025 mg/100 g, s.c.), the latter two were administered for an additional two days after surgery. During the procedure mice were maintained on 1.5-2% isoflurane. Six alternating swabs of povidone and 70% ethanol were used to create a sterile field prior to providing a local anesthetic (bupivacaine 0.125%, 100 μl, s.c.), after which an incision was made to expose the skull, and meninges and skin pushed to the edges of the skull. Vetbond® was applied to the edge of skin and exposed skull to facilitate a 6-mm craniotomy using a manual dental drill (0.5 mm drill bit). Once the skull fragment was removed using forceps, a piece of surgifoam was applied to stop any bleeding prior to placing an 8-mm diameter round glass coverslip (1.5 mm thickness, Electron Microscopy Sciences #72296-08), which was affixed to the remaining skull using cyanoacrylate (Loctite 406). The coverslip was allowed to adhere for 6 minutes before surrounding it with dental cement to cover any remaining exposed skull and create a small well for water immersion objectives during imaging.

In vivo two-photon excitation fluorescence (2PEF) imaging. During two-photon imaging sessions, mice were kept under 1-1.5% isoflurane mixed with medical air (21% 02, 78% $N_2$), placed on a custom-made stereotactic frame, and injected with glycopyrrolate (0.5 mg/100 g i.m.), 5% glucose (100 μl/h of imaging, s.c.), 50 μl of Texas Red 70 kDa dextran (2.5% diluted in 0.9% saline, r.o.) to visualize the cerebral vasculature, in some mice, leukocytes and blood platelets were labeled by injecting Rhodamine 6G (50 μL, 1 mg/mL in 0.9% saline), and Hoescht 33342 (50 μL, 4.8 mg/mL in 0.9% saline). 40 μl of 10 mg/ml FITC-BSA was loaded in coacervate, DOPC LipCo to visualize vesicles, and all the preparation steps are as described in the LipCo preparation section. 200 μl of vesicle in 0.9% saline was injected via a retro-orbital sinus. Breathing rate was maintained at 1 Hz by adjusting isoflurane levels, and body temperature was monitored and kept at 37° C. throughout imaging sessions. Laser scanning and data acquisition were controlled by ScanImage software through MATLAB. Images from up to 5 locations (1-3 capillary beds, one vein, and one artery) were acquired with a 25× water immersion objective (Olympus, NA of 1.05) by resonant scanning (1000 frames, 33 Hz, 512×512 pixels/line) every 20 min up to 2 h after injections. Imaging was performed using an excitation wavelength of 830 nm, 100-fs pulses from a Ti: Sapphire laser oscillator (Chameleon, Coherent). Emitted fluorescence was detected on a four-channel detection system: For capillary stalling analysis, a 488 nm dichroic was used to split channels 1/2 from 3/4, 560 nm dichroic for separating channels 1 and 2, and 801 nm dichroic for channels 3 and 4. For 4-channel imaging in veins and arteries, a 532 nm dichroic was used to split channels 1/2 from 3/4, 488 nm dichroic for separating channels 1 and 2, and 593 nm dichroic for channels 3 and 4. Additional band-pass filters were used to visualize Hoescht in channel 1 (439/154), Rhodamine 6G in channel 2 (494/41, FITC in channel 3 (579/34), and blood vessels in channel 4 (645/55).

In vivo circulation events analysis. The captured LipCo images in the mice's brain veins were analyzed to identify vesicle behavioral events in vivo. There were three identified events: flowing, slow-moving, and non-following. For the flowing LipCo vesicles, the images were analyzed via NIH Image J script FindPeaks within the regions of interest. When a flowing vesicle passed through the region of interest, a single event would be recorded via the script. As for the slow-moving and non-flowing events, images were examined manually. The slow-moving events will be recorded as a single vesicle moved and remained in the same observation window for up to 5 seconds. Non-flowing events were recorded when a single vesicle became stocked and remained in the same observation window for more than 20 seconds.

In vivo biodistribution. 6-8 weeks-old female BALB/c mice were purchased from Charles River Laboratories. Upon arrival, alfalfa-free chow and omega/alpha-dry bedding were immediately used to minimize potential fluorescence interference from the diet. After at least three days of acclimation, mice received a subcutaneous injection of 200 μl of coacervate or DOPC LipCo with 25% Cy-5 heparin into the flank. Mice were euthanized 4 h, 24 h, 48 h, and 1 week after injection. The major organs (liver, lung, kidney, heart, spleen) were harvested and resined with PBS. The average fluorescence intensity of each organ was determined using an in vivo imaging system (IVIS) spectrum. For LipCo with glycolipid, 200 μl of vesicle suspension was injected through the tail vein. Mice were euthanized 4 h, 24 h, 48 h, and 1 week after injection. All other procedures were as described above.

Vesicle blood clearance profile. A vesicle blood clearance profile was performed as previously reported. Briefly, 200 μl of LipCo with glycolipid suspension was injected through the tail vein in mice. At 0.5, 6-, 24-, 48-, and 72-hours post-injection, 20 μl of whole blood was collected through a saphenous vein on the leg. 2 μl of heparin sodium was mixed with whole blood as an anticoagulant. The blood samples were then analyzed with a microplate reader, with the excitation at 640 nm and emission measurement at 647 nm.

Statistics. Data are presented as mean±standard deviation (S.D.). The statistical significance was determined by Student's 1-test.

Figure 19:
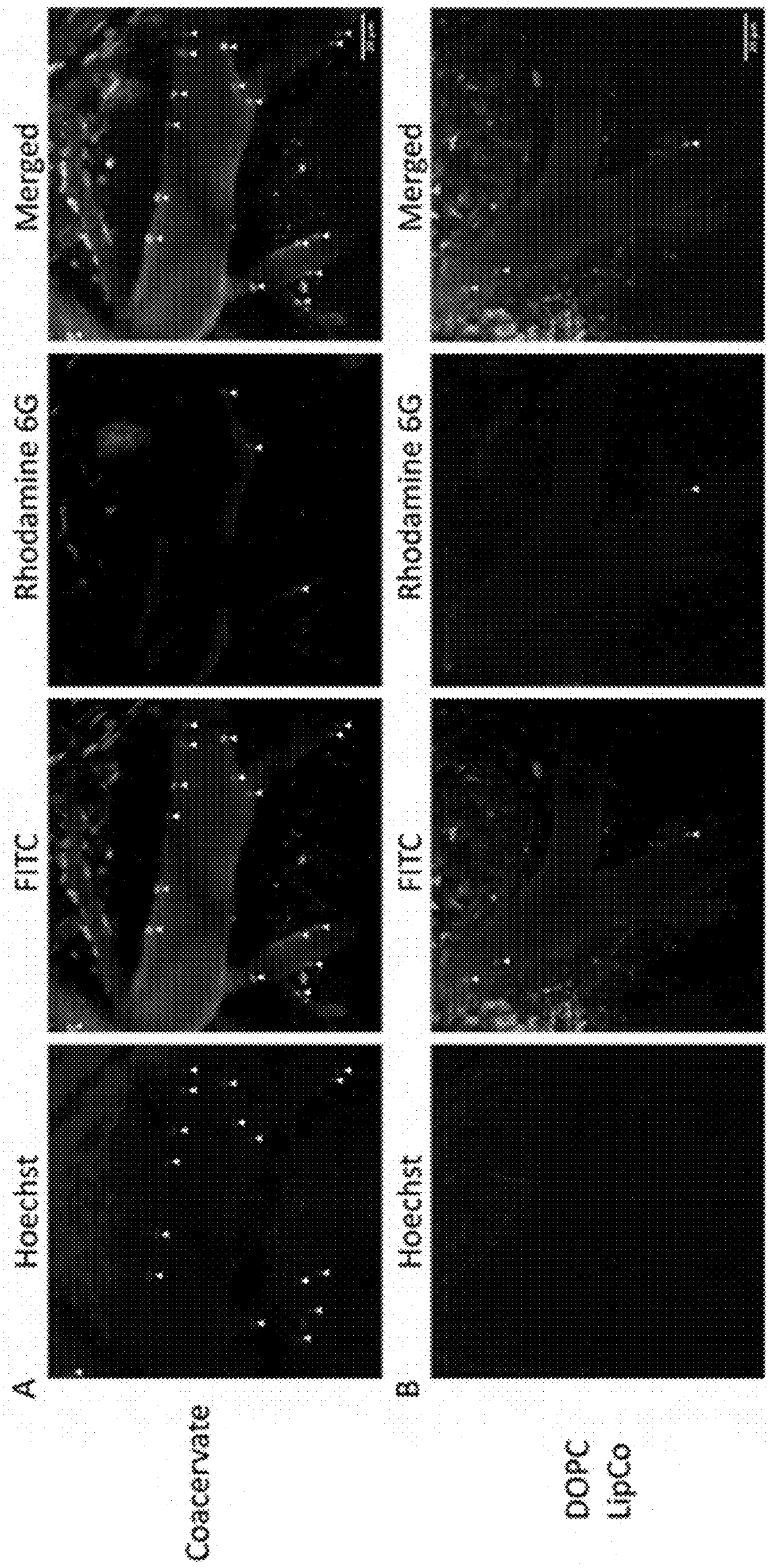
FIG. 19 shows two-photon excited fluorescence (2PEF) microscopic images of vesicles in mouse brain veins. A-Co-localization of white blood cells (Hoechst, blue) and coacervate vesicles (FITC, green) adhered to the mouse brain vein wall was observed. B-Few DOPC LipCo (FITC, green) vesicles were observed adhering. Blue: Hoechst. Green: FITC. Red: Rhodamine 6G. White triangles highlight the co-localization of blood cells and vesicles. Scale bar: 20 μm.
Figure 20:
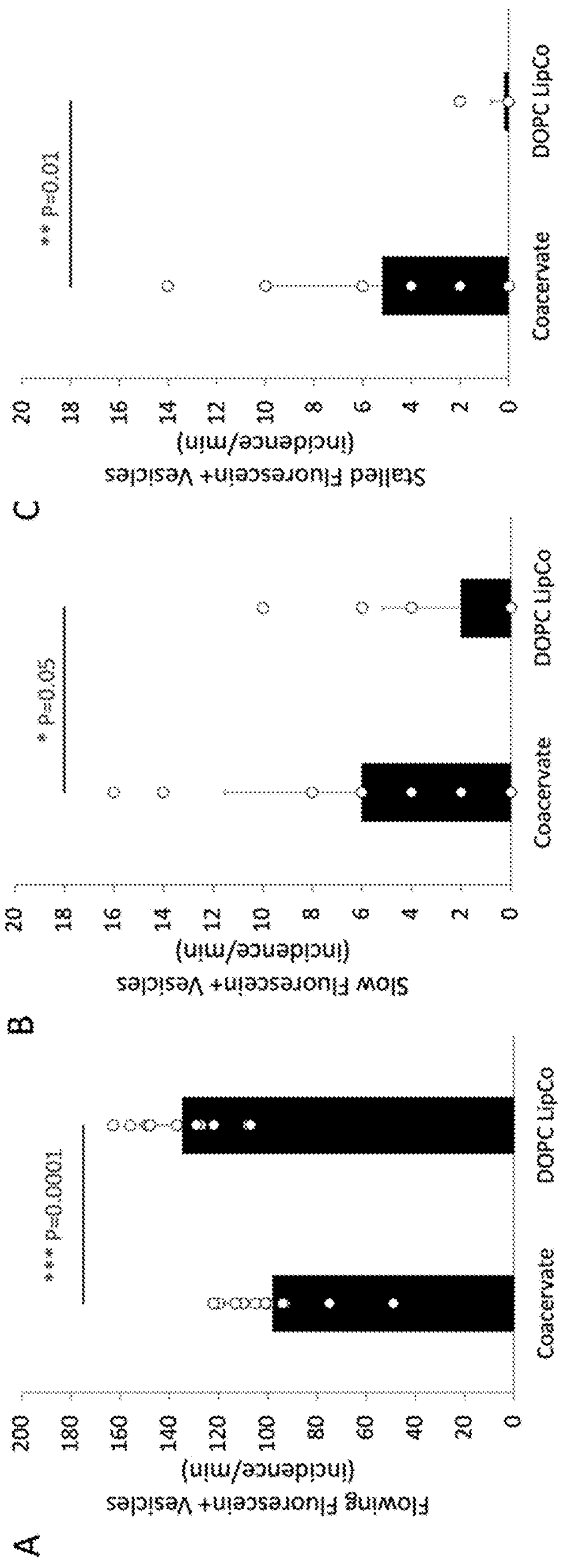
FIG. 20 shows vesicle circulation event analysis. A-Flowing fluorescein-positive vesicles. B-Slow fluorescein-positive vesicles. C-Stalled fluorescence-positive vesicles. Data are presented as mean±standard (n=3). The open circles represent the actual data point. *: p<0.05. : p<0.01. *: p<0.001.

Results. Vesicle in vivo circulation. To understand the circulation dynamics of coacervate and DOPC LipCo in the bloodstream, 2PEF microscopy and intravital imaging techniques were utilized to observe the real-time vesicle circulation within mouse brain vasculature. Coacervate (green) vesicles were observed to co-localize with white blood cells stained with Hoechst (blue) (FIG. 19A). Slow-moving coacervate vesicles were identified, remaining within the observation area for up to 5 seconds, with some observed rolling along the vein wall. This was contributed to the slightly positive charged surface when prepared coacervate with PEAD to heparin mass ratios of 4. The number of stalled coacervate vesicles stuck on the vein wall was found to be significantly higher (FIG. 20C). Conversely, DOPC LipCo, with a lipid membrane providing a stealth surface, showed no obvious co-localization with white blood cells (FIG. 19B). Consequently, the overall flowing events from DOPC LipCo were significantly higher compared to coacervate, with reduced slow-moving and stalled events (FIG. 20). Similar circulation patterns were identified in mouse brain capillaries as previously reported in EXAMPLE 3. Taken together, Coacervate vesicles exhibited co-localization with white blood cells, slower movement, and a higher incidence of stalling along vein walls, while DOPC LipCo showed minimal interaction with white blood cells and higher overall flowing events.

Figure 21:
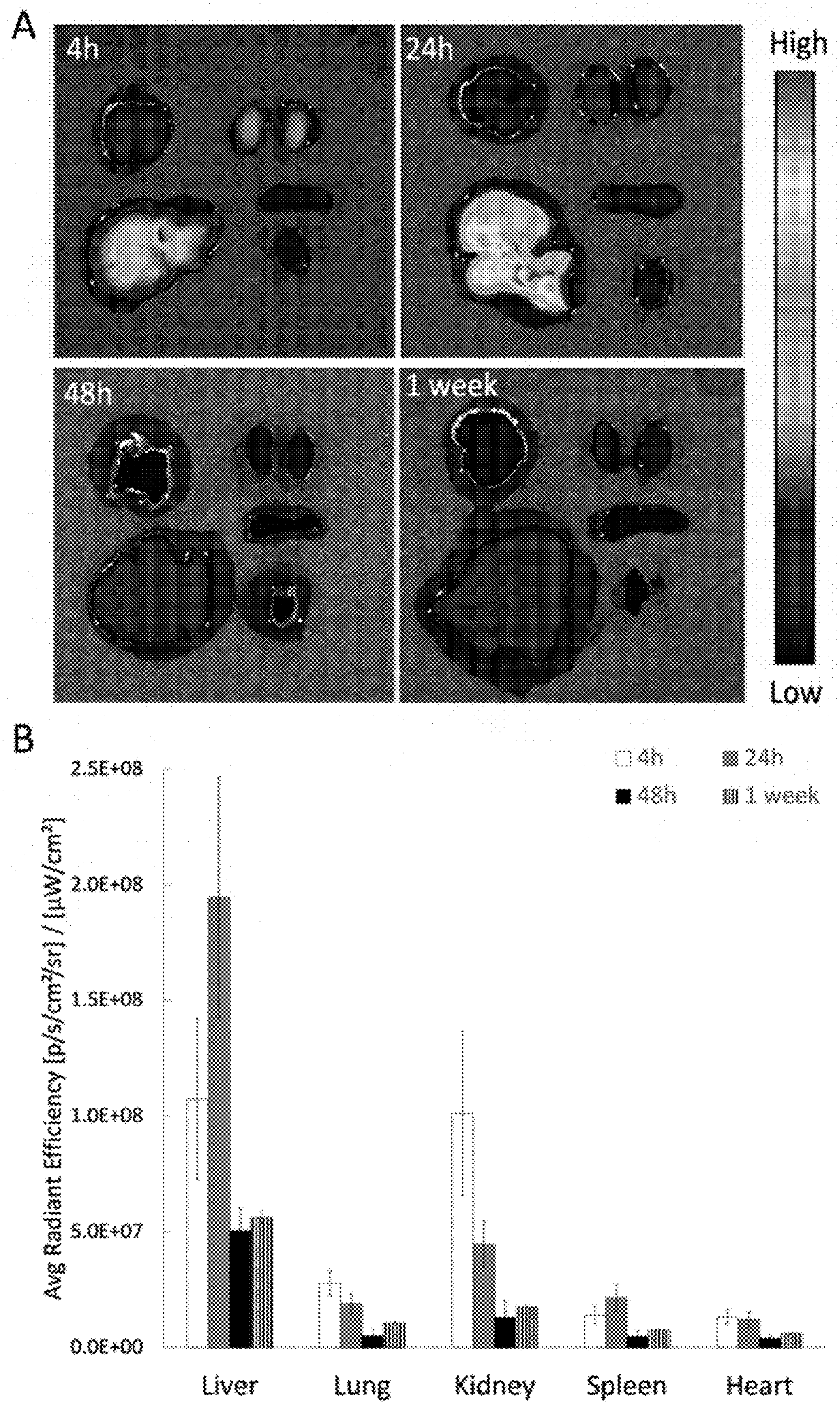
FIG. 21 shows coacervate in vivo biodistribution. A-shows fluorescent images of Cy-5 heparin-loaded coacervate in major organs (Left column: lung and liver. Right column: kidneys, spleen, and heart) at 4 h, 24 h, 48 h, and 1-week post-injection. The color scale represents fluorescence levels in different tissues. B-A quantitative assessment of average radiant efficiency per cm2 is presented with Cy-5 heparin-loaded coacervate. White bar: 4 h. Gray bar: 24 h. Black bar: 48 h. Black patterned bar: 1 week. Data are shown as mean±standard deviation (n=3).
Figure 22:
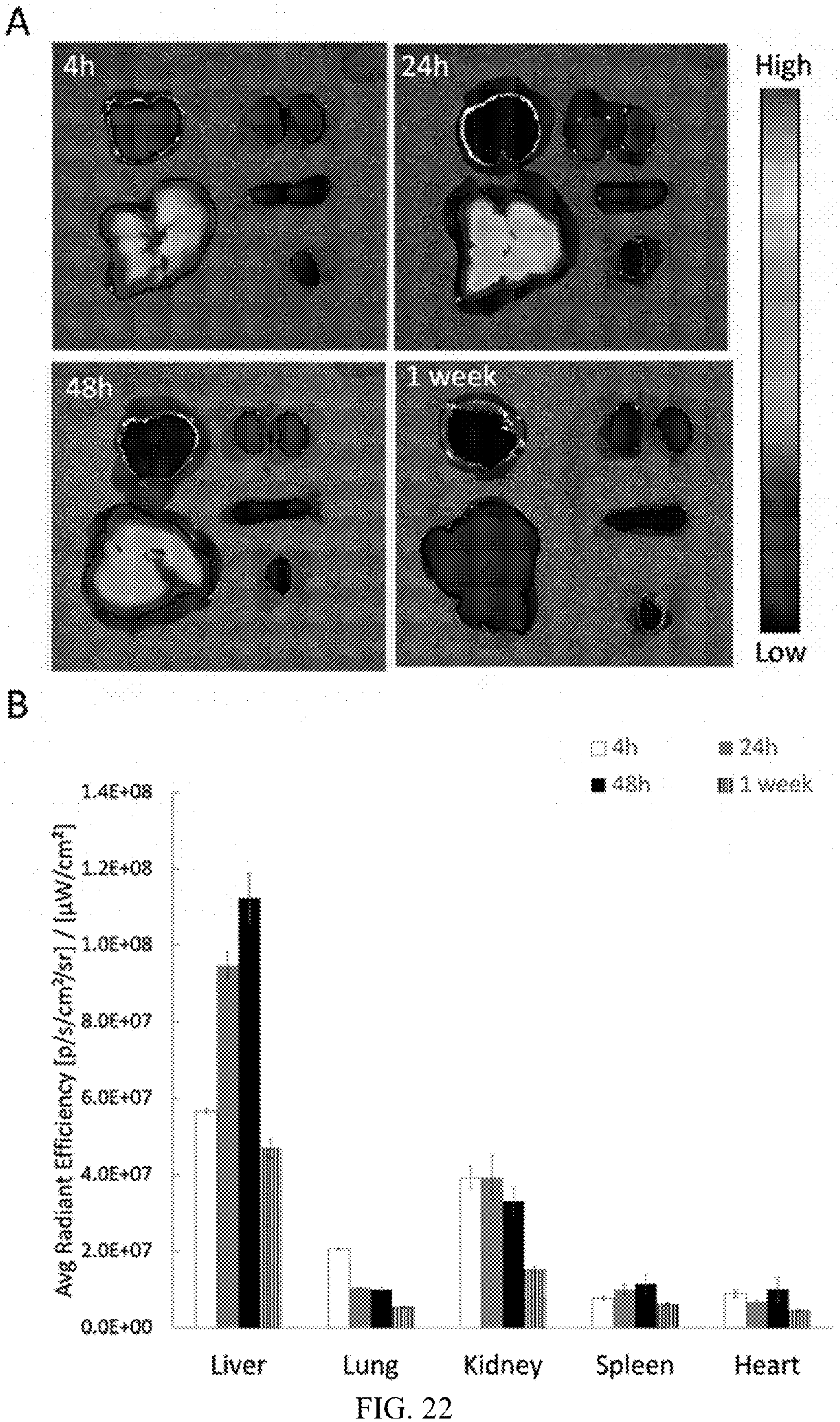
FIG. 22 shows LipCo in vivo biodistribution. A-shows fluorescent images of Cy-5 heparin-loaded DOPC LipCo in major organs (Left column: lung and liver. Right column: kidneys, spleen, and heart) at 4 h, 24 h, 48 h, and 1-week post-injection. The color scale represents fluorescence levels in different tissues. B-A quantitative assessment of average radiant efficiency per cm2 is presented with Cy-5 heparin-loaded DOPC LipCo. White bar: 4 h. Gray bar: 24 h. Black bar: 48 h. Black patterned bar: 1 week. Data are shown as mean±standard deviation (n=3).

Vesicle in vivo biodistribution. In vivo imaging system (IVIS) and fluorescence imaging were utilized to assess the biodistribution of Cy-5 heparin-loaded coacervate and DOPC LipCo in major organs at 4 h, 24 h, 48 h, and 1-week post-injection. Both vesicles exhibited high fluorescence intensities in the liver and kidneys at 4 h post-injection (FIGS. 21A and 22A). Quantitative analysis revealed rapid hepatic accumulation and renal clearance of coacervate within 48 hours (FIG. 21B). In contrast, DOPC LipCo showed gradual liver accumulation, peaking at 48 h post-injection (FIG. 22B). After 1 week, both coacervate and DOPC LipCo exhibited similar fluorescence levels in the liver, indicating a comparable level of accumulation and degradation of vehicles via hepatic metabolic pathway. Based on the analysis of in vivo events, coacervate vesicles exhibited a propensity to aggregate and adhere within vessels, potentially leading to clot formation and rapid clearance from the body. Conversely, DOPC LipCo demonstrated a smoother circulation pattern, undergoing gradual degradation within the body over time. The prolonged fluorescence intensity decay observed in the livers of mice administered with DOPC LipCo suggests an extended circulation time compared to the rapid accumulation of coacervate in the liver, which subsequently diminished rapidly.

Figure 23:
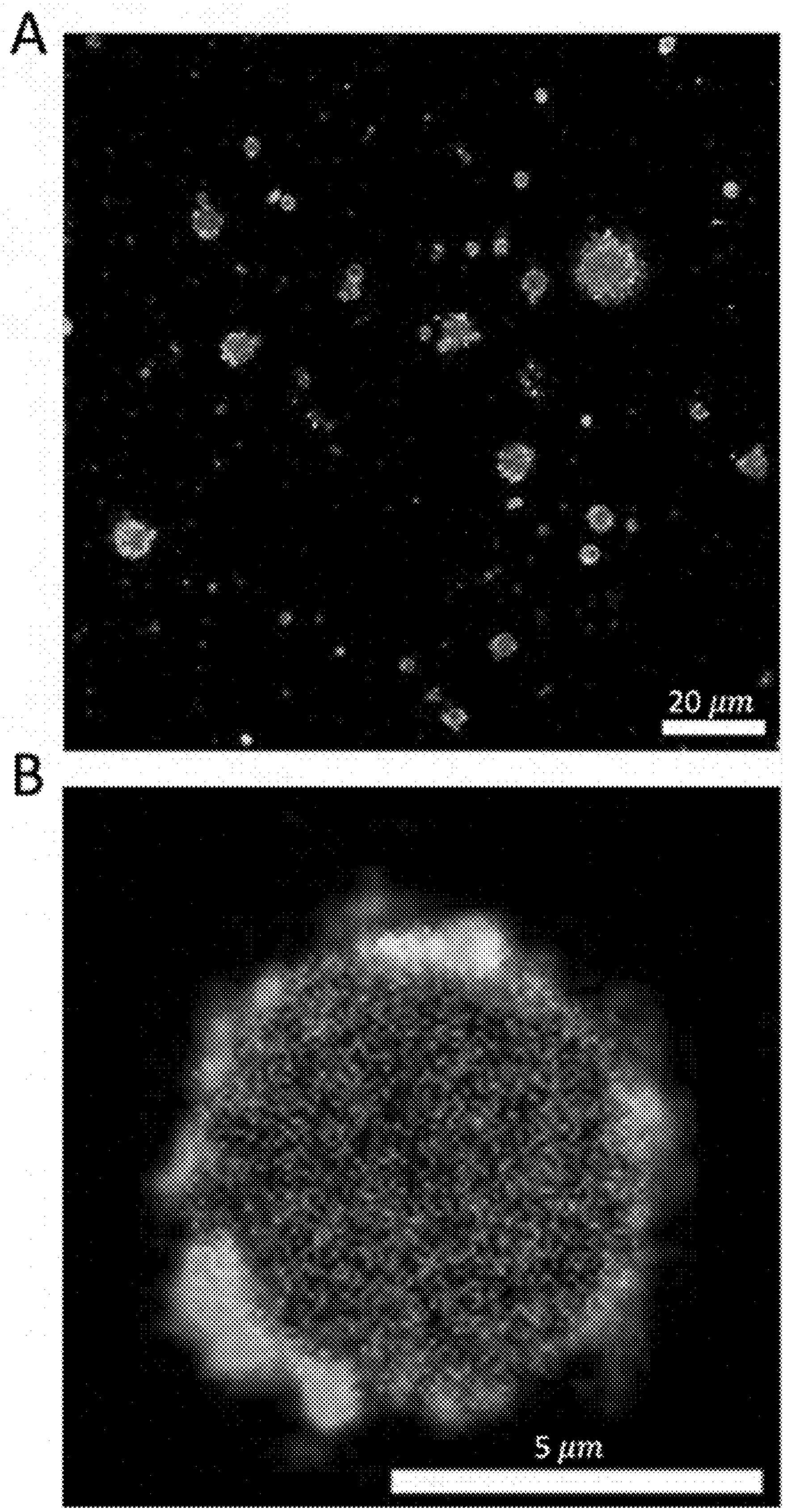
FIG. 23 shows confocal microscopy images of LipCo with glycolipid. A-Confocal microscopy image depicting LipCo formulation showing the formed LipCo were discrete spheres. Scale bar: 20 μm. B-A high magnification image of LipCo with glycoprotein. The red fluorescent interior of Cy-5 heparin-loaded PEAD/heparin coacervate was enclosed via a green, fluorescent 34:1 PC/ganglioside/cholesterol lipid layer. Scale bar: 5 μm.

Long-circulating LipCo with glycolipid. Given the potential of prolonged circulation in the bloodstream resulting from lipid assembly, LipCo formulations were prepared using lipid mixtures intended to mimic the composition of the erythrocyte membrane outer leaflet. Notably, phosphocholine (PC) represents the most abundant lipid found in the outer leaflet of the red blood cell membrane, with 34:1 PC and sphingomyelin being particularly prevalent. In this study, a lipid formulation consisting of 34:1 PC/ganglioside/cholesterol in a molar ratio of 2:2:1 was selected, as it embodies characteristics reminiscent of the erythrocyte membrane. Confocal microscopy images (FIG. 23) illustrate a green fluorescent lipid outer layer encapsulating a red fluorescent Cy-5 heparin coacervate core, similar to the DOPC LipCo structure previously reported.

Figure 24:
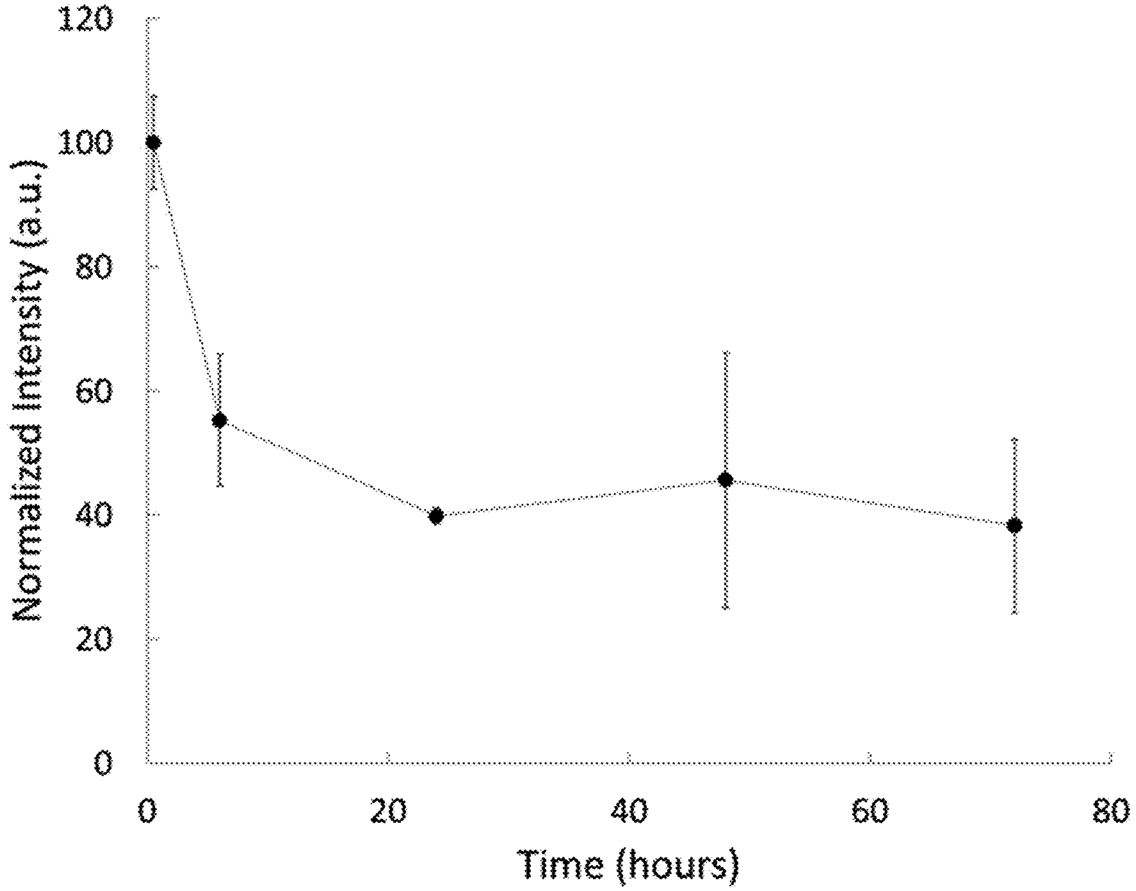
FIG. 24 shows the blood clearance profile of LipCo with glycolipid. The plot shows changes in normalized fluorescence intensity for blood samples taken at various times after injection of Cy5-loaded LipCo with glycolipid. Data are shown as mean±standard deviation (n=3 independent mice).

To analyze the biodistribution and blood elimination half-live of LipCo with glycolipid, in vivo experiments were conducted by administering LipCo with glycolipid suspension via tail vein injection in mice. Similar to coacervate and DOPC LipCo, LipCo with glycolipid predominately accumulated in the liver and kidneys at 4 h post-injection. Notably, LipCo with glycolipid possessed prolonged fluorescence intensity decay observed in the livers of mice, similar to DOPC LipCo (FIG. 21D). The blood clearance profile indicated that approximately 40% of LipCo with glycolipid vesicles injected were retained in the blood after 24 hours (FIG. 24). Based on the pharmacokinetics profiles, the initial elimination half-life was 17 hours for the LipCo with glycolipid. The pseudo-equilibrium state was observed after 24 h post-injection, resulting from the equal number of vesicles moving into tissues and moving back into the plasma.

Discussion. In this study, the naked PEAD/heparin complex coacervate with a positively charged surface (+1 mV) shows more slow-moving, rolling, and stalled events, compared to DOPC LipCo with a negatively charged surface (−1.2 mV) demonstrates more flowing events in mice brain vasculature. Positively charged nanoparticles may interact with negatively charged platelets, increase platelet-platelet interaction, and facilitate platelet aggregation. This may explain that the naked PEAD/heparin complex coacervate exhibits an increased number of slow-moving and stalled events and rolling on the vessel wall in mice brain vasculature (FIG. 19). Furthermore, the positively charged surface may facilitate the phagocytosis by macrophages, possibly due to the positively charged surface associated with the negatively charged sialic acid group on macrophages. Thus, the naked PEAD/heparin complex coacervates are observed colocalized with Hoechst-stained white blood cells, while it is not awarded in DOPC LipCo (FIG. 19).

The biodistribution results suggest coacervates possessed rapid liver accumulation and renal clearance (FIG. 21), while DOPC LipCo shows gradual liver accumulation (FIG. 22), suggesting the potential of DOPC LipCo could escape from MPS and possess long circulation properties. LipCo with glycolipid exhibits a similar biodistribution pattern to DOPC LipCo. The blood clearance profile suggests an initial elimination half-life of 17 h (FIG. 24). Compared to known erythrocyte membrane enclosed DEAE-dextran/DNA coacervate with initial elimination half-live of 31 minutes in rabbit, the LipCo with glycolipid shows extended circulation possibly due to the ganglioside to prevent macromolecule association on the LipCo surface and deformability of LipCo to facilitate extravasation and prevent capillaries blockage.

The dogma of liposome literature is that long circulating liposome should be in the nanometer range and should employ PEGylated lipids. Meanwhile, lipid with high transition temperature and high rigidity such as saturated DPPC is chosen as the components to provide stability and prevent the leakage of loaded therapeutic drug. By using PEGylated lipid, one should be aware that PEG may block and interfere with receptor-mediated endocytosis, hinder endosomal escape, bind the released drug, and accelerate blood clearance with repeated injection of PEGylated liposome due to anti-PEG immune responses. A micro-sized LipCo with glycolipid is described. The micro-sized vesicle possesses a high loading capacity. Gangliosides provide a hydrophilic layer on the LipCo surface to exclude macromolecules from this space, preventing aggregation and enhancing long circulation. This novel LipCo formulations circumvent existing limitations and optimize therapeutic delivery systems for enhanced efficacy and safety. Vesicle-cell interaction, specifically how LipCo with glycolipid interacts with macrophages, and application of LipCo with glycolipid on disease model are warranted to further assess the LipCo utility to systemically deliver therapeutic agents.

To understand the circulation dynamics of coacervate and DOPC LipCo in the bloodstream, 2PEF microscopy and intravital imaging techniques were utilized to observe the real-time vesicle circulation within mouse brain vasculature. Coacervate (green) vesicles were observed to co-localize with white blood cells stained with Hoechst (blue) (FIG. 19A). Slow-moving coacervate vesicles were identified, remaining within the observation area for up to 5 seconds, with some observed rolling along the vein wall. We contributed this to the slightly positive charged surface when prepared coacervate with PEAD to heparin mass ratios of 4. The number of stalled coacervate vesicles stuck on the vein wall was found to be significantly higher (FIG. 20C). Conversely, DOPC LipCo, with a lipid membrane providing a stealth surface, showed no obvious co-localization with white blood cells (FIG. 19B). Consequently, the overall flowing events from DOPC LipCo were significantly higher compared to coacervate, with reduced slow-moving and stalled events (FIG. 20). Similar circulation patterns were identified in mouse brain capillaries as previously reported in EXAMPLE 3. Taken together, Coacervate vesicles exhibited co-localization with white blood cells, slower movement, and a higher incidence of stalling along vein walls, while DOPC LipCo showed minimal interaction with white blood cells and higher overall flowing events.

The in vivo circulation and biodistribution of vesicles are examined here. Naked PEAD/heparin complex coacervates exhibit increased numbers of slow-moving and stalled events with rapid hepatic accumulation and renal clearance. While DOPC LipCo demonstrates increased numbers of flowing events and gradual liver accumulation. LipCo with erythrocyte membrane mimicking lipid composition shows prolonged fluorescence decay in the liver, suggesting prolonged circulation. The blood clearance profile reveals an initial elimination half-life of 17 h. All data suggest the micro-sized LipCo with glycolipid possesses long circulation properties. Future studies on LipCo vesicle-cell interaction and the application of LipCo on disease models are warranted to assess its therapeutic potential for protein delivery.

Although the present disclosure has been described with respect to one or more particular example(s), it will be understood that other examples of the present disclosure may be made without departing from the scope of the present disclosure.

The invention claimed is:

1. A lipocoacervate (LipCo) comprising:

a coacervate phase; and one or more lipid(s), wherein the lipid(s) is/are disposed on at least a portion of an exterior surface of the coacervate phase;

wherein the coacervate phase comprises: one or more cationic component(s) and one or more anionic component(s); and wherein the one or more cationic component(s) are chosen from poly (ethylene argininylaspartate diglyceride), spermine, spermidine, and any combination thereof.

2. A LipCo of claim 1, wherein the LipCo comprises a coacervate to lipid(s) mass ratio of about 95:5 to about 99.9997:0.0003.

3. The LipCo of claim 1, wherein the coacervate phase comprises a multidomain polymer comprising two or more oppositely charged domains.

4. The LipCo of claim 1, wherein the one or more cationic component(s) is/are independently a non-naturally-occurring polycation or a naturally-occurring polycation and/or the one or more anionic component(s) is/are independently a naturally-occurring polyanion.

5. The LipCo of claim 1, wherein the one or more anionic component(s) is a biomolecule.

6. The LipCo of claim 1, wherein the one or more anionic component(s) is/are chosen from polyanions.

7. The LipCo of claim 1, wherein the polyanions is/are chosen from glycosaminoglycans, nucleic acids, negatively-charged proteins, and any combination thereof.

8. A LipCo according to claim 1, wherein a mass ratio of the one or more cationic component(s) to the one or more anionic component(s) is about 4 to about 1.

9. The LipCo of claim 1, wherein the one or more lipid(s) is/are chosen from fats, oils, waxes, vitamins, hormones, phospholipids, glycerolipids, glycerophospholipids, sphingolipids, glycolipids, sterols, and any combination thereof.

10. The LipCo of claim 1, wherein in the one or more lipid(s) comprise(s) dioleoylphosphatidylcholine (DOPC), 1,2-Distearoyl-sn-glycero-3-phospho-rac-glycerol (DSPG), dipalmitoylphosphatidylcholine (DPPC), 1-palmitoyl-2-oleoyl-glycero-3-phosphocholine (POPC), ganglioside, sphingomyelin, or a salt thereof, or any combination thereof.

11. The LipCo of claim 1, wherein the LipCo further comprises one or more biomolecule(s).

12. The LipCo of claim 11, wherein the one or more biomolecule(s) is/are independently a therapeutic agent, a bioactive agent, a biofunctional agent, or any combination thereof.

13. The LipCo of claim 11, wherein the one or more biomolecule(s) is/are present at about 1 weight percent (wt. %) to about 60 wt. %.

14. The LipCo of claim 11, wherein the one or more biomolecule(s) is/are independently chosen from proteins.

15. The LipCo of claim 14, wherein the proteins are chosen from growth factors, interleukins, and any combination thereof.

16. The LipCo of claim 1, wherein the LipCo further comprises a localization tag.

17. The LipCo of claim 1, wherein the LipCo comprises a longest linear dimension of about 100 nanometers to about 20 micrometers.

18. A composition comprising a plurality of LipCos of claim 1.

19. The LipCo of claim 18, wherein the LipCos further comprise one or more biomolecule(s) and the one or more biomolecule(s) is/are present at about 1 wt. % to about 80 wt. %.

20. The composition of claim 18, wherein the LipCos comprise an average longest linear dimension of about 100 nanometers to about 20 microns.

21. The composition of claim 18, wherein the LipCos exhibit an average zeta potential of about −5 mV to about +5 mV.

22. The composition of claim 18, wherein the composition comprises one or more pharmaceutical excipient(s).

23. The composition of claim 18, wherein at least a portion, substantially all, or all the LipCos independently further comprise(s) one or more biomolecule(s).

24. The composition of claim 18, wherein the composition does not exhibit observable LipCo aggregation or greater than about 5% observable change in LipCo average longest linear dimension for at least one week or more at a temperature of about 4 degrees Celsius, or both.

25. A method of making lipocoacervates (LipCos) or a LipCo composition, where the LipCo(s) comprise a LipCo of claim 1, the method comprising:

contacting a coacervate composition with a lipid composition, wherein the LipCos are or the LipCo composition is formed.

26. The method of claim 25, wherein the coacervate composition is formed by contacting an aqueous solution of one or more cationic component(s) and one or more anionic component(s).

27. The method of claim 26, wherein the one or more anionic component(s) is a biomolecule.

28. The method of claim 26, wherein the one or more cationic component(s) and the one or more anionic component(s) are present in a mass ratio of about 4 to about 1.

29. The method of claim 25, the method further comprising isolating the LipCos.

30. A method of biomolecule delivery comprising:

contacting a population of cells or an individual with one or more LipCo(s) of claim 1, wherein at least a portion or all of the LipCos independently further comprise one or more biomolecule(s), wherein at least a portion of or all of the LipCo(s) is/are delivered to the population of cells, or the individual.

31. The method of claim 30, wherein the contacting comprises administration of the LipCo(s) to the individual.

32. The method of claim 30, wherein the LipCo(s) is/are taken up by a cell or cells of the population of cells or the individual, and the biomolecule(s) is/are is released within the cell or cells.

33. The method of claim 30, wherein the biomolecule(s) retain/retains after delivery substantially all biological activity compared with native biomolecule(s) or biomolecule(s) delivered without use of a LipCo(s).

34. The method of claim 30, wherein the individual is diagnosed with and/or is in need of treatment for a disease or a disease state, and the disease or the disease state is treatable or preventable by the biomolecule(s).

35. The method of claim 30, wherein the LipCos are present in one or more composition(s), each composition comprising a plurality of LipCos.

* * * * *